US 7,037,503 B2

(12) United States Patent
Collier et al.

(10) Patent No.: US 7,037,503 B2
(45) Date of Patent: May 2, 2006

(54) COMPOUNDS AND METHODS FOR THE TREATMENT AND PREVENTION OF BACTERIAL INFECTION

(75) Inventors: R. John Collier, Wellesley, MA (US); Bret R. Sellman, Rochester, NY (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/848,909

(22) Filed: May 4, 2001

(65) Prior Publication Data

US 2002/0039588 A1 Apr. 4, 2002

Related U.S. Application Data

(60) Provisional application No. 60/201,800, filed on May 4, 2000.

(51) Int. Cl.
*A61K 39/07* (2006.01)
*C12N 9/54* (2006.01)

(52) U.S. Cl. .............................. 424/190.1; 424/184.1; 424/236.1; 424/246.1; 530/350; 435/221

(58) Field of Classification Search .................. 514/2, 514/26, 12; 435/252.3, 7.21, 69.1, 252.31, 435/320.1, 480, 69.7, 221; 530/350, 402; 536/23.7, 23.4; 424/234.1, 183.1, 184.1, 424/185.1, 203.1, 236.1, 245.1, 239.1, 136.1, 424/143.1, 238.1, 178.1, 150.1, 93.21, 200.1, 424/246.1, 93.46, 235.1, 94.63, 190.1, 134.1
See application file for complete search history.

(56) References Cited

U.S. PATENT DOCUMENTS

| 5,591,631 | A | | 1/1997 | Leppla et al. ............. 435/252.3 |
| 5,677,274 | A | | 10/1997 | Leppla et al. .................. 514/2 |
| 5,792,458 | A | * | 8/1998 | Johnson et al. ........... 424/183.1 |
| 5,917,017 | A | * | 6/1999 | Collier et al. ............... 530/350 |
| 6,267,966 | B1 | * | 7/2001 | Baillie ...................... 424/200.1 |
| 6,329,156 | B1 | * | 12/2001 | Cirino et al. .............. 435/7.21 |
| 6,413,768 | B1 | * | 7/2002 | Galen ...................... 435/320.1 |
| 6,426,231 | B1 | * | 7/2002 | Bayley et al. .............. 436/518 |
| 6,455,673 | B1 | * | 9/2002 | Collier et al. ............... 530/350 |

FOREIGN PATENT DOCUMENTS

| WO | WO 94/18332 | | 8/1994 |
| WO | WO 97/23236 | | 7/1997 |
| WO | 99/42473 | * | 8/1999 |
| WO | WO 99/42473 | | 8/1999 |

OTHER PUBLICATIONS

Bossier, F et al, Infection and Immunity, vol. 68(4), Apr. 2000, pp. 1781-1786.*
Moayeri, M et al, Infection and Immunity, vol. 65(6), pp. 2233-2239, Jun. 1997.*
Price, Lance B. et al, Journal of Bacteriology, vol. 181(8), pp. 2358-2362, Apr. 1999, Genetic Diversity in the Protective antigen gene of *Bacillus anthracis*.*

(Continued)

*Primary Examiner*—Lynette R. F. Smith
*Assistant Examiner*—Ginny Allen Portner
(74) *Attorney, Agent, or Firm*—Clark & Elbing LLP

(57) ABSTRACT

The invention provides mutant forms of pore-forming toxins. These mutant toxins may be used in vaccines for the prevention of bacterial infection. Additionally, dominant negative mutants may be administered as therapeutics for the treatment of bacterial infection.

10 Claims, 22 Drawing Sheets

OTHER PUBLICATIONS

Sellmam, BR et al, Journal of Biological Chemistry, vol. 276(11), Mar. 16, 2001, pp. 8371-8376.*
Cherry, J.D., Clinical infectious diseases:an official publication of the Infectious Diseases Society of America, Mar. 1999, vol. 28(3), pp. 560-561, (abstract only).*
Guttman, Cheryl, Ophthalmology Times, vol. 27, No. 10, p. 17.*
Varughese, M et al, Apr. 1999, vol. 67(4), pp. 1860-1865.*
Boslego, J. W. et al, Chapter 17, pp. 211-233, Vaccines and Immunotherapies, Pergamon Press, 1991.*
Ellis, RW. Chapter 29, New Technologies for Making Vaccines, In : Vaccines, Sunders Company, 1988, pp. 568-574.*
Miller, C et al, Protein Science, Voo. 7(1), p. 175, abstract 712-M, 1998.*
Miller, CJ et al, Biochemistry, vol. 38, pp. 10432-10441, 1999.*
Leppla, SH et al, Journal of Applied Microbiology, vol. 87, p. 284, 1999.*
Steinthorsdottir, V et al, Microbial Pathogenesis, Jan. 2000, vol. 28(1), pp. 45-50.*
Cabiaux, V et al, Biophys, Journal, Voo. 61 (2 part 2), p. A211, 1992, abstract 1211.*
Anderluh, G et al, European Journal of Biochemistry, vol. 263(1), pp. 128-136, Jul. 1999 (germany).*
Singh, Y et al, Infection and Immunity, vol. 67(4), pp. 1853-1859, Apr. 1999.*
Papageorgiou, AC et al, Protein Science, a publication of the Protein Society, Aug. 1996, Voo. 5(8), pp. 1737-1741.*
Tiedemann, RE etal, PNAS, vol. 92(26), pp. 12156-12159, Dec. 19, 1995.*
Singh, Y et al, J. Biol. Chem., vol. 269(46), pp. 29039-29046, Nov. 1994.*
Yamaoka, J et al, Microbial pathogenesis, Nov. 1997, pp. 297-302, Nov. 1997.*
Jobling, MG et al, Mol. Microbiology, vol. 5(7), pp. 1755-1767, 1991.*
Singh, Y et al, Journal of Biological Chemistry, vol. 276(25), pp. 22090-22094, Jun. 22, 2001.*
Welch, RA, Current Topics in Microbiology and Immunology-Pore-forming toxins, pp. 85-111, vol. 257, 2001.*
DeWolf, MJ et al, Biochimica et biophysica acta, Sep. 8, 1994, vol. 1223(3), pp. 285-295.*
Anu, D et al, Pesticide Biochemistry and Physiology, May 2001, pp. 7-18, vol. 70(1).*
Shatursky, O et al, Cell, Oct. 29, 1999, vol. 99(3), pp. 293-299.*
Wesche, J et al, Biochemistry, vol. 37(45) pp. 15737-15746, 1998.*
Blaustein, Robert O et al, PNAS (USA), vol. 86, pp. 2209-2213, Apr. 1989.*
Kim, Myung-Hee et al, Journal of Biological Chemistry, vol. 275(9), Mar. 3, pp. 6175-6180, 2000.*
Sellman, Bret R. et al, The Journal of Biological Chemistry, vol. 276(11), pp. 8371-8376, Mar. 16, 2001.*
Sellman, Bret R. et al, Science, vol. 292, Apr. 27, 2001, pp. 695-697.*
Wesche, J et al, Biochemistry, vol. 37, pp. 15737-15746, 1998.*

Benson et al., "Identification of residues lining the anthrax protective antigen channel," *Biochemistry* 37:3941-3948 (1998).
Blaustein et al., "Anthrax toxin: channel-forming activity of protective antigen in planar phospholipid bilayers," *Proc. Natl. Acad. Sci. U.S.A.* 86:2209-2213 (1989).
Braha et al., "Designed protein pores as components for biosensors," *Chemistry & Biology* 4(7):497-505 (1997).
Elliot et al., "A Quantitative Study of the Interactions of *Bacillus anthracis* Edema Factor and Lethal Factor with Activated Protective Antigen," *Biochemistry* 39:6706-6713 (2000).
Huynh et al., "Probing the structure of the diphtheria toxin channel. Reactivity in planar lipid bilayer membranes of cysteine-substituted mutant channels with methanethiosulfonate derivatives," *J. Gen. Physiol.* 110: 229-242 (1997).
Miller et al., "Anthrax Protective Antigen: Prepore-to Pore Conversion," *Biochemistry* 38(32):10432-10441 (1999).
Miller et al., "Prepore-to Pore Conversion by Activated Anthrax Toxin Protective Antigen," Protein Science 7(1): 175, abstract No. 712-M, (1998).
Milne et al., "Anthrax protective antigen forms oligomers during intoxication of mammalian cells," *J. Biol. Chem.* 269(32):20607-20612 (1994).
Milne et al., "Protective antigen-binding domain of anthrax lethal factor mediates translocation of a heterologous protein fused to its amino- or carboxy-terminus," *Mol. Microbiol.* 15(4):661-666 (1995).
Petosa et al., "Crystal structure of the anthrax toxin protective antigen," *Nature* 385:833-838 (1997).
Sellman et al., "Point Mutations in Anthrax Protective Antigen That Block Translocation," *J. Biol. Chem.* 276:8371 (2001).
Sellman et al., "Dominant-negative mutants of a toxin subunit: an approach to therapy of anthrax," *Science* 292: 695-697 (2001).
Song et al., "Structure of *Staphylococcal* α-hemolysin, a heptameric transmembrane pore," *Science* 274(13):1859-1866 (1996).
Valeva et al., "Transmembrane β-barrel of *Staphylococcal* α-toxin forms in sensitive but not in resistant cells," *Proc. Natl. Acad. Sci. U.S.A.* 94:11607-11611 (1997).
Vinion-Dubiel et al., "A Dominant Negative Mutant of *Heliocobacter pylori* Vacuolating Toxin (VacA) Inhibits VacA-induced Cell Vacuolation," The Journal of Biological Chemistry, 274:37736-37742 (1999).
Vodkin et al., "Cloning of the Protective Antigen Gene of *Bacillus anthracis,*" *Cell* 34:693-697 (1983).
Walker et al., "A pore-forming protein with a protease-activated trigger," *Protein Engineering* 7(1):91-97 (1994).
Wesche et al., "Characterization of Membrane Translocation by Anthrax Protective Antigen," *Biochemistry* 37:15737-15746 (1998).
Klimpel et al., "Anthrax toxin protective antigen is activated by a cell surface protease with the sequence specificity and catalytic properties of furin," *Proc. Natl. Acad. Sci. U.S.A.* 89:10277-10281 (1992).

* cited by examiner

FIG. 13

Figure 13: SEQ ID No.: 21

EVKQENRLLNESESSSQGLLGYYFSDLNFQAPMVTSSTGDLSIPSSELENIPSEN
QYFQSAIWSGFIKVKKSDEYTFA
TSADNHVTMWVDDQEVINKASNSNKIRLEKGRLYQIKIQYQRENPTEKGLDFKL
YWTDSQNKKEVISSDNLQLPELKQKS
SNSRKKRSTSAGPTVPDRDNDGIPDSLEVEGYTVDVKNKRTFLSPWISNIHEKKG
LTKYKSSPEKWSTASDPYSDFEKVT
GRIDKNVSPEARHPLVAAYPIVHVDMENIILSKNEDQSTQNTDSETRTISKNTSTS
RTHTSEVHGNAEVHASFFDIGGSV
SAGFSNSNSSTVAIDHSLSLAGERTWAETMGLNTADTARLNANIRYVNTGTAPIY
NVLPTTSLVLGKNQTLATIKAKENQ
LSQILAPNNYYPSKNLAPIALNAQDDFSSTPITMNYNQFLELEKTKQLRLDTDQV
YGNIATYNFENGRVRVDTGSNWSEV
LPQQETTARIIFNGKDLNLVERRIAAVNPSDPLETTKPDMTLKEALKIAFGFNEPN
GNLQYQGKDITEFDFNFDQQTSQ
NIKNQLAELNATNIYTVLDKIKLNAKMNILIRDKRFHYDRNNIAVGADESVVKEA
HREVINSSTEGLLLNIDKDIRKILS
GYTVEIEDTEGLKEVINDRYDMLNISSLRQDGKTFIDFKKYNDKLPLYISNPNYKV
NVYAVTKENTIINPSENGDTSTNG
IKKILIFSKKGYEJGZ

FIG. 14

Figure 14: SEQ ID No.: 22

```
GAAGTTAAACAGGAGAACCGGTTATTAAATGAATCAGAATCAAGTTCCCAGG
GGTTACTAGGATACTATTTTAGTGATTT
GAATTTTCAAGCACCCATGGTGGTTACCTCTTCTACTACAGGGGATTTATCTA
TTCCTAGTTCTGAGTTAGAAAATATTC
CATCGGAAAACCAATATTTTCAATCTGCTATTTGGTCAGGATTTATCAAAGTT
AAGAAGAGTGATGAATATACATTTGCT
ACTTCCGCTGATAATCATGTAACAATGTGGGTAGATGACCAAGAAGTGATTA
ATAAAGCTTCTAATTCTAACAAAATCAG
ATTAGAAAAAGGAAGATTATATCAAATAAAAATTCAATATCAACGAGAAAAT
CCTACTGAAAAAGGATTGGATTTCAAGT
TGTACTGGACCGATTCTCAAAATAAAAAGAAGTGATTTCTAGTGATAACTT
ACAATTGCCAGAATTAAAACAAAAATCT
TCGAACTCAAGAAAAAAGCGAAGTACAAGTGCTGGACCTACGGTTCCAGACC
GTGACAATGATGGAATCCCTGATTCATT
AGAGGTAGAAGGATATACGGTTGATGTCAAAAATAAAAGAACTTTTCTTTCA
CCATGGATTTCTAATATTCATGAAAAGA
AAGGATTAACCAAATATAAATCATCTCCTGAAAAATGGAGCACGGCTTCTGA
TCCGTACAGTGATTTCGAAAAGGTTACA
GGACGGATTGATAAGAATGTATCACCAGAGGCAAGACACCCCCTTGTGGCAG
CTTATCCGATTGTACATGTAGATATGGA
GAATATTATTCTCTCAAAAAATGAGGATCAATCCACACAGAATACTGATAGT
GAAACGAGAACAATAAGTAAAAATACTT
CTACAAGTAGGACACATACTAGTGAAGTACATGGAAATGCAGAAGTGCATGC
GTCGTTCTTTGATATTGGTGGGAGTGTA
TCTGCAGGATTTAGTAATTCGAATTCAAGTACGGTCGCAATTGATCATTCACT
ATCTCTAGCAGGGGAAAGAACTTGGGC
TGAAACAATGGGTTTAAATACCGCTGATACAGCAAGATTAAATGCCAATATT
AGATATGTAAATACTGGGACGGCTCCAA
TCTACAACGTGTTACCAACGACTTCGTTAGTGTTAGGAAAAAATCAAACACT
CGCGACAATTAAAGCTAAGGAAAACCAA
TTAAGTCAAATACTTGCACCTAATAATTATTATCCTTCTAAAAACTTGGCGCC
AATCGCATTAAATGCACAAGACGATTT
CAGTTCTACTCCAATTACAATGAATTACAATCAATTTCTTGAGTTAGAAAAAA
CGAAACAATTAAGATTAGATACGGATC
AAGTATATGGGAATATAGCAACATACAATTTTGAAAATGGAAGAGTGAGGGT
GGATACAGGCTCGAACTGGAGTGAAGTG
TTACCGCAAATTCAAGAAACAACTGCACGTATCATTTTTAATGGAAAAGATTT
AAATCTGGTAGAAAGGCGGATAGCGGC
GGTTAATCCTAGTGATCCATTAGAAACGACTAAACCGGATATGACATTAAAA
GAAGCCCTTAAAATAGCATTTGGATTTA
ACGAACCGAATGGAAACTTACAATATCAAGGGAAAGACATAACCGAATTTG
ATTTTAATTTCGATCAACAAACATCTCAA
AATATCAAGAATCAGTTAGCGGAATTAAACGCAACTAACATATATACTGTAT
TAGATAAAATCAAATTAAATGCAAAAAT
```

FIG. 14 (CONTINUED)

```
GAATATTTTAATAAGAGAGATAAACGTTTCATTTATGATAGAAATAACATAGCA
GTTGGGGCGGATGAGTCAGTAGTTAAGG
AGGCTCATAGAGAAGTAATTAATTCGTCAACAGAGGGATTATTGTTAAATAT
TGATAAGGATATAAGAAAAATATTATCA
GGTTATATTGTAGAAGATACTGAAGGGCTTAAAGAAGTTATAAATG
ACAGATATGATATGTTGAATATTTCTAG
TTTACGCAAGATGGAAAAACATTTATAGATTTTAAAATATAATGATAAA
TTACCGTTATATAAGTAATCCCAATT
ATAAGGTAAATGTATATGCTGTTACTAAAGAAAAACACTATTATTAATCCTAGT
GAGAATGGGGATACTAGTACCAACGGG
ATCAAGAAAATTTTAATCTTTTCTAAAAAAGGCTATGAGATAGGATAA
```

COMPOUNDS AND METHODS FOR THE TREATMENT AND PREVENTION OF BACTERIAL INFECTION

CROSS REFERENCE TO RELATED APPLICATIONS

This application claims priority from U.S. Provisional Application No. 60/201,800, filed May 4, 2000.

STATEMENT AS TO FEDERALLY SPONSORED RESEARCH

This invention was funded by grants R37-AI22021 and 2T32-AI07410 from the National Institute of Health. The government may have certain rights in the invention.

BACKGROUND OF THE INVENTION

In general, the invention features compounds and methods for the treatment of bacterial infections, such as anthrax infection.

The etiologic agent of anthrax (*Bacillus anthracis*) is a potential threat as an agent of biowarfare or bioterrorism because exposure to aerosolized *B. anthracis* spores can be lethal to mammals, such as humans. The major virulence factors produced by this organism are the poly-D-glutamic acid capsule and anthrax toxin (ATx). Both the capsule and the toxin assist in colonization and immune evasion by the bacterium. ATx alone can cause death of the host. Vaccination against the toxin protects the host against infection.

Anthrax toxin is a member of the class of bacterial toxins termed A-B toxins. A-B toxins are composed of two moieties; the A moiety is the enzymic portion of the toxin that catalyzes the toxic effect upon a cytoplasmic target within a target cell. The B moiety binds to a cellular receptor and facilitates the translocation of the A moiety across the cell membrane into the cytoplasm of the cell.

The B moieties of A-B toxins from tetanus, botulinum, diphtheria and anthrax all form channels in membranes. It has been hypothesized that these channels might act as the conduit for the membrane translocation of the A moiety. The A and B moieities of anthrax toxin are secreted from the bacterial cell as distinct polypeptides. The A and B subunits of other A-B toxins are produced as single chain polypeptides or as separate chains that are assembled into oligomeric toxins before release from the bacteria. There are two alternative A subunits of anthrax toxin called edema factor (EF) and lethal factor (LF). Noncovalent complexes of EF or LF and the B subunit, protective antigen (PA), are called edema toxin and lethal toxin, respectively. PA facilitates the translocation of both EF and LF across membranes.

PA is secreted as an 83 kDa monomeric polypeptide. Monomeric PA binds to a mammalian cell surface receptor and is proteolytically cleaved. The C-terminal 63 kDa fragment (PA63) remains bound to the cell and the N-terminal 20 kDa (PA20) dissociates from PA63. This proteolytic cleavage and subsequent dissociation of PA20 confer two new properties on PA63: (1) the ability to oligomerize into a ring-shaped heptameric SDS-dissociable structure termed prepore and (2) the ability to bind EF and LF. Oligomers containing PA63-EF, PA63-LF, or a combination of PA63-EF and PA63-LF are endocytosed and trafficked to an acidic compartment, where the PA63 prepore inserts into the membrane and forms a pore. During or after pore formation, EF and LF are translocated across the endosomal membrane into the cytoplasm. EF is a calmodulin-dependent adenylate cyclase which may protect the bacteria from destruction by phagocytes. LF is a metalloprotease that can kill macrophages or, at lower concentrations, induce macrophages to overproduce cytokines, possibly resulting in death of the host.

A crucial step in this intoxication pathway is pore formation by PA. Low pH serves as the trigger for conversion of the PA63 prepore to the pore. This conversion is accompanied by a transformation of the oligomer from an SDS-dissociable to an SDS-resistant state and formation of a transmembrane 14-strand β-barrel. These steps are believed to be necessary for translocation of EF and LF across the endosomal membrane and, thus, toxin action.

SUMMARY OF THE INVENTION

In a first aspect, the invention provides a B moiety of a pore-forming binary A-B toxin. The B moiety has a mutation that results in inhibition of its pore-forming ability. In one desirable embodiment, this mutation results in inhibition of the pore-forming ability of the protein in vivo. In another desirable embodiment, the mutant B moiety lacks pore-forming ability in vitro and/or in vivo. In yet another desirable embodiment, the B moiety is anthrax protective antigen (PA). In yet another desirable embodiment, the PA mutant has an amino acid sequence that is at least 80%, 90%, 95% or 98% identical to a naturally-occurring PA protein (such as SEQ ID No.: 21; FIG. 13) and that has one of the following alterations: K397A, K397D, K397C, K397Q, D425A, D425N, D425E, D425K, F427A, K397+D425K double mutation, K395D+K397D+D425K+D426K quadruple mutation, ΔD2L2 PA (deletion of residues 302–325), K397D+D425K+F427A triple mutation, F427A+ΔD2L2 double mutation, K397D+F427A+ΔD2L2 triple mutation, K397D+D425K+F427A+ΔD2L2 quadruple mutation, F427D, or F427K. In another desirable embodiment, the PA mutant has a sequence identical to any of SEQ ID Nos.: 1–18 (Table 1). Other desirable PA mutants include PA mutants in which residue 397 is any amino acid except lysine (SEQ ID No.: 19), PA mutants in which residue 425 is any amino acid except aspartic acid (SEQ ID No.: 20), PA mutants in which residue 427 is any amino acid except phenylalanine (SEQ ID No.: 23), and PA mutants that have a mutation in domain 2 (residues 259–487). Still other desirable mutant B moieties include *Clostridium difficile, C. perfringens, C. spiroforme, C. botulinum, Bacillus cereus*, or *B. thuringiensis* toxins that have one or more of the alterations listed in Table 6 or that have a mutation in the region that corresponds to domain 2 of PA. Fragments of the above mutant B moieties, in which the fragment has a reduced pore-forming ability compared to a naturally-occurring B moiety of the corresponding toxin, are also included in the invention. Fusion proteins having a mutant B moiety of the invention or a fragment of such a mutant B moiety covalently bound to another polypeptide or protein are also included. In one embodiment, specifically excluded from this aspect is the deletion of amino acids 302–325 (D2L2 loop) of PA.

In a second aspect, the invention features a vaccine composition having a mutant B moiety of the first aspect, or a fragment thereof, in a pharmaceutically acceptable carrier. In a desirable embodiment, the vaccine can be inactivated by chemical or physical means. In one embodiment, specifically excluded from this aspect is a vaccine having ΔD2L2 PA as its sole mutant B moiety.

In a third aspect, the invention features a method of preventing or treating bacterial infection in a mammal, such as a human. This method includes administering the vaccine of the second aspect to the mammal. In one desirable embodiment, the vaccine is administered with a pharmaceutically suitable carrier or an adjuvant. The vaccine can be administered orally, intramuscularly, intravenously, subcutaneously, by inhalation, or by any other route sufficient to provide a dose adequate to prevent or treat a bacterial infection. In another desirable embodiment, a vaccine that includes a mutant anthrax protective antigen is administered for the prevention or treatment of anthrax infection. In one embodiment, specifically excluded from this aspect is a method that involves administration of a vaccine having ΔD2L2 PA as its sole mutant B moiety and that does not involve administration of another vaccine having another mutant B moiety.

In a fourth aspect, the invention provides a mutant B moiety of a pore-forming binary A-B toxin. The mutant B moiety has a mutation that results in inhibition of its pore-forming ability. The mutant B moiety also inhibits the pore-forming ability of a naturally-occurring B moiety of the corresponding toxin in vitro and/or in vivo. In one desirable embodiment, this mutation results in inhibition of the pore-forming ability of the protein in vivo. In another desirable embodiment, the mutant B moiety lacks pore-forming ability in vitro and/or in vivo. In yet another desirable embodiment, the B moiety is anthrax protective antigen (PA). The mutant B moiety may bind the A moiety of the corresponding toxin. For example, a PA mutant may bind the lethal factor or edema factor A moieties. The mutant B moiety may compete with a naturally-occurring B moiety for binding to a receptor on the surface of a mammalian cell. The mutant B moiety may also bind a naturally-occurring B moiety of the corresponding toxin. Such a mutant may oligomerize with a naturally-occurring B moiety to form a complex that has reduced ability to form a pore. In one desirable embodiment, the complex lacks the ability to form a pore and to translocate an A moiety (e.g., EF or LF) across the membrane into the host cell cytoplasm.

In one desirable embodiment of the fourth aspect, the mutant PA has an amino acid sequence that is at least 80%, 90%, 95%, or 98% identical to a naturally-occurring PA protein (such as SEQ ID No. 21; FIG. 13) and that has one of the following alterations: K397D+D425K double mutation, ΔD2L2 (in which residues 302–325 of PA are deleted), K395D+K397D+D425K+D426K quadruple mutation, D425K, F427A, K397D+D425K+F427A triple mutation, F427A+ΔD2L2 double mutation, K397D+F427A+ΔD2L2 triple mutation, K397D+D425K+F427A+ΔD2L2 quadruple mutation, F427D, or F427K In another desirable embodiment, the PA mutant has a sequence identical to any of SEQ ID Nos.: 8–18 (Table 1). In another embodiment, amino acid 395, 397, 425, 426, or a combination thereof, in naturally-occurring PA is mutated. In yet another embodiment, a residue in domain 2 of PA is mutated. In another desirable embodiment, the mutant has a deletion of at least 5, at least 10, or at least 20 amino acids of the residues in the D2L2 loop of PA or in the corresponding region of a B moiety of another pore-forming binary A-B toxin. The mutant can have a deletion of all or part of the D2L2 loop and a deletion of amino acids that are N- or C-terminal to the loop. Still other desirable mutant B moieties include *Clostridium difficile, C. perfringens, C. spiroforme, C. botulinum, Bacillus cereus,* or *B. thuringiensis* toxins that have one or more of the alterations listed in Table 6 or that have a mutation in the region that corresponds to domain 2 of PA. Fragments of the above mutant B moieties, in which the fragment has a reduced pore-forming ability compared to a naturally-occurring B moiety and inhibits the pore-forming ability of a naturally-occurring B moiety, are included in the invention. Fusion proteins having a mutant B moiety or a fragment of a mutant B moiety covalently bound to another polypeptide or protein are included.

In a fifth aspect, the invention features a method of preventing or treating bacterial infection in a mammal, such as a human. This method includes administering a mutant B moiety of the fourth aspect, or a fragment thereof, that inhibits the pore-forming ability of a naturally-occurring B moiety to the mammal. In one embodiment, a PA mutant of the fourth aspect or a fragment thereof is administered to prevent or treat anthrax infection in mammals that have been exposed to *B. anthracis* spores. In another embodiment, the protein is administered prophylactically. In one desirable embodiment, the mutant B moiety is administered with a pharmaceutically suitable carrier. The mutant may be administered orally, intramuscularly, intravenously, subcutaneously, by inhalation, or by any other route sufficient to provide a dose adequate to prevent or treat an anthrax infection. In one embodiment, the method also includes administering an anti-B moiety antibody, such as an antibody that binds a naturally-occurring B moiety but not the dominant negative mutant B moiety, to the mammal. In one particular embodiment, the antibody binds a naturally-occurring PA but not the dominant negative PA mutant.

In a sixth aspect, the invention features a nucleic acid encoding a mutant B moiety (e.g., a PA mutant) of the first or fourth aspects.

In a seventh aspect, the invention features a vector having the nucleic acid of the sixth aspect.

In an eighth aspect, the invention features a purified antibody that specifically binds a naturally-occurring PA or a PA mutant protein listed in Table 1. In one embodiment, the antibody binds to the D2L2 loop, K397, D425, D426, or F427 of a PA protein. The antibody may be a monoclonal or polyclonal antibody. In a related aspect, the invention features a purified antibody that specifically binds a naturally-occurring B moiety of a pore-forming binary A-B toxin with greater affinity than it binds a B moiety of the present invention from the corresponding toxin. In another related aspect, the invention features a purified antibody that specifically binds a B moiety of the present invention with greater affinity than it binds a naturally-occurring B moiety of the corresponding toxin.

In one embodiment of the first or fourth aspects, specifically excluded are those PA molecules having as their sole alteration, a mutation to cysteine of a residue located in the hydrophilic face of a transmembrane pore. In another embodiment of these aspects, PA molecules having as their sole alteration a mutation in an amino acid in the hydrophilic face of a transmembrane pore are specifically excluded. In a embodiment, specifically excluded from the first or fourth aspects are those PA molecules having as their sole alteration, a mutation in Glu302, His304, Asn306, Glu308, His310, Ser312, Phe313, Phe314, Asp315, Gly317, Ser319, Ser321, Gly323, or Ser325 in naturally-occurring PA. In one embodiment of these aspects, PA molecules having as their sole alteration, a mutation in the amino acid sequence of the D2L2 loop are specifically excluded. In another embodiment, PA molecules having as their sole alteration a mutation or deletion in an amino acid that forms the transmembrane pore are specifically excluded. In yet another embodiment, specifically excluded from one of these aspects are PA molecules having the C-terminal 63 kDA tryptic fragment (PA63) and having as their sole alteration a mutation in an amino acid that forms the transmembrane pore. In still another embodiment, specifically excluded is ΔD2L2

PA. In various other embodiments, specifically excluded from one of these aspects are other pore-forming binary A-B toxins that have a mutation that corresponds to a specifically excluded PA mutation. In various embodiments of these aspects, the mutant B moiety binds a naturally-occurring B moiety from the same A-B toxin with a higher equilibrium constant (i.e., with greater affinity) than the naturally-occurring B-moiety binds other naturally-occurring molecules from the same A-B toxin. In desirable embodiments, the mutant PA protein binds naturally-occurring PA with at least 2, 5, 10, or 20 fold greater affinity than naturally-occurring PA binds other naturally-occurring PA molecules.

It should be understood that other pore-forming toxins, in addition to anthrax toxin, may be used in the compounds and methods of the invention. For example, pore-forming toxins, such as other A-B toxins, having mutations (e.g., point mutations or deletion mutations) that inhibit the pore-forming ability of the toxin or that inhibit the pore-forming ability of the naturally-occurring toxin are included in the invention. The pore-forming toxins with these mutants can be used in the vaccine compositions or methods of the invention to prevent or treat infection by the etiologic agent of the toxin. While not meant to limit the invention in any way, other A-B binary toxins; hetero-oligomeric toxins (AB5 toxins), such as cholera toxin; or single polypeptide A-B toxins, such as tetanus, botulinum, or diphtheria toxin can be used. Other toxins that can be used include α-hemolysin from *Staphylococcus aureus*, aerolysin from *Aeromonas hydrophila*, α-toxin from *Clostridium septicum*, and cytotoxin from *Pseudomonas aeruginosa*. The invention is also relevant to any other pore-forming toxin such as cholesterol dependent cytolysins, hexameric toxins, or heptameric toxins. Examples of hexameric and heptameric toxins include toxins that are related to the Staphylococcal α-toxin. In one embodiment, a deletion mutant of the VacA toxin from *Helicobacter pylori* is specifically excluded.

"Mutation" means an alteration in the nucleic acid sequence such that the amino acid sequence encoded by the nucleic acid sequence has at least one amino acid alteration from a naturally-occurring sequence. The mutation may, without limitation, be an insertion, deletion, frameshift mutation, or missense mutation.

"Pore-forming toxin" means a toxin which forms a transmembrane aqueous pore.

"Pore-forming A-B toxin" means a pore-forming toxin with two functional moieties; one moiety (B) which forms a pore in a host cell barrier membrane, and the other (A) traverses the membrane barrier and enzymatically modifies specific intracellular substrates of a host cell.

"Pore-forming binary A-B toxin" means a pore-forming A-B toxin in which the A and B moieties of the pore-forming toxin inhabit separate proteins, and interact during the intoxication of host cells. An example of a binary toxin is anthrax toxin.

"B moiety" means the component of a pore-forming A-B toxin which binds a specific host cell-surface receptor, interacts with the A moiety of the toxin, and aids in internalization of the A moiety into the cell. Many B moieties, such as PA, also form transmembrane pores.

"Protective antigen (PA)" means a polypeptide having at least 60%, 70%, 80%, or 90%, of at least one of the biological activities of the anthrax PA polypeptide described herein. The polypeptide may be encoded by the PA gene that was reported by Vodkin et al. (Cell 34:693–697, 1983). The polypeptide can be identical to wild-type PA characterized by Miller et al. (Biochemistry 38(32):10432–10441, 1999) (SEQ ID No.: 21) or any naturally-occurring PA polypeptide from a strain of *Bacillus anthracis*. The PA polypeptide may be cloned and expressed in a heterologous host, such as *Escherichia coli* or *Bacillus subtilis*. It is understood that homologs and analogs have the characteristics of the anthrax PA described herein and may be used in the methods of the invention.

"PA63" means the carboxy-terminal portion that results from proteolytic cleavage of a 20 kDa N-terminal segment from the PA polypeptide. PA63 forms a heptameric prepore and binds the two alternative A moieties, edema factor (EF) and lethal factor (LF). The entire complex is trafficked to the endosome, where PA63 inserts into the membrane, forms a transmembrane pore, and translocates EF and LF into the host cell cytoplasm.

"Transmembrane pore" means a transmembrane aqueous channel. For example, the transmembrane pore can be a β-barrel channel formed by alternating hydrophilic and hydrophobic residues of PA63 such that the hydrophobic residues form an exterior membrane-contiguous surface of the barrel, and the hydrophilic residues face an aqueous lumen of a pore that spans across the host cell membrane.

"Hydrophilic face of a transmembrane pore" means the amino acids of PA that face the aqueous lumen of a pore that spans across the host cell membrane.

"An amino acid that forms the transmembrane pore" means an amino acid of PA that is located in a β-barrel channel of a transmembrane pore.

"D2L2 loop" means the amphipathic loop which connects strands 2β2 and 2β3 of PA polypeptide and PA63 polypeptide as described herein.

"Inhibits the pore-forming ability" means reduces the amount of pores formed in membranes or reduces the rate or amount of an A moiety (e.g., EF or LF) that is translocated into the host cell cytoplasm. This decrease in pore formation or toxin translocation is positively correlated with, and could be predicted by, a decrease in activity in the cell surface translocation, LFnDTA toxicity, or rubidium release assays described herein. This decreased activity can be correlated with a decrease in the amount of a radiolabeled ligand that is translocated into cells in the cell surface translocation assay, a decrease in the inhibition of protein synthesis due to the translocation of a ligand into cells in the LFnDTA toxicity assay, or a decrease in the release of radiolabeled ions from cells in the rubidium release assay. Additionally, this decreased activity can be correlated with a decrease in toxicity due to the translocation of a toxic ligand into cells. In one desirable embodiment, the decrease in pore formation or translocation of an A moiety is at least 20%, more desirably at least 40%, and most desirably at least 80% relative to a naturally-occurring B moiety of the corresponding toxin. In another desirable embodiment, the decrease in pore formation or translocation of EF or LF by a PA mutant is at least 20%, more desirably at least 40%, and most desirably at least 80% relative to naturally-occurring PA63

"Lacks pore-forming ability" means does not form a significant amount of pores in membranes or does not transfer a significant amount of EF or LF into the host cell cytoplasm. This lack of significant pore-forming or toxin translocating activity is positively correlated with, and could be predicted by, a lack of significant activity in the cell surface translocation, LFnDTA toxicity, or rubidium release assays described herein. In one desirable embodiment, the amount of pores formed or the amount of toxin translocated is less than 5 times the amount detected in a control assay without PA. More desirably, the amount is less than 2 times the amount in a control assay without PA.

"Fragment" means polypeptide having a region of consecutive amino acids that is identical to the corresponding region in a PA mutant. The fragment has either a reduced ability to form pores or translocate toxins compared to naturally-occurring PA. The fragment may also inhibit the pore-forming ability of naturally-occurring PA. This decrease in pore formation or toxin translocation is positively correlated with, and could be predicted by, a decrease in activity in the cell surface translocation, LFnDTA toxicity, or rubidium release assays described herein. This decreased activity can be correlated with a decrease in the amount of a radiolabeled ligand that is translocated into cells in the cell surface translocation assay, a decrease in the inhibition of protein synthesis due to the translocation of a ligand into cells in the LFnDTA toxicity assay, or a decrease in the release of radiolabeled ions from cells in the rubidium release assay. In one desirable embodiment, the decrease in pore formation or translocation of EF or LF is at least 20% relative to naturally-occurring PA63. More desirably, the decrease is at least 40%, and most desirably, the decrease is at least 80%. The inhibition of the pore-forming ability of naturally-occurring PA is positively correlated with, and could be predicted by, a decrease in activity in an assay described above using an equimolar mixture of naturally-occurring PA and a PA fragment compared to using naturally-occurring PA alone. In one desirable embodiment, the decrease is at least 20, 40, 60, 80, or 99% compared to the activity using only naturally-occurring PA. Desirably, the fragment is immunogenic and induces the production of protective antibodies against naturally-occurring PA. In another desirable embodiment, the administration of the fragment to a mammal, as described in Example 9, prevents or diminishes an anthrax infection for a period of at least 1 month, more desirably 3 months, or most desirably 6 months. Examples of possible fragments include the C-terminal 63 kDA tryptic fragment of a PA mutant or a PA mutant having a deletion of amino acids that form the transmembrane pore.

By "purified antibody" is meant an antibody which is at least 60%, by weight, free from proteins and naturally-occurring organic molecules with which it is naturally associated. Desirably, the preparation is at least 75%, more desirably 90%, and most desirably at least 99%, by weight, antibody. A purified antibody may be obtained, for example, by affinity chromatography using recombinantly-produced protein or conserved motif peptides and standard techniques.

By "specifically binds" is meant an antibody that recognizes and binds to, for example, wild-type PA or a PA mutant but does not substantially recognize and bind to other non-PA molecules in a sample, e.g., a biological sample, that naturally includes protein. A desirable antibody specifically binds any of the PA mutants # 1–18 in Table 1. Other desirable antibodies bind wild-type PA with at least 2, 5, 10, or 20 fold greater affinity than they bind one or more of the PA mutants in Table 1.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

Other features and advantages of the invention will be apparent from the following detailed description.

BRIEF DESCRIPTION OF THE DRAWINGS

FIG. 13 is the amino acid sequence of wild-type PA protein used for the assays described herein (SEQ ID No.: 21). The PA mutant proteins described herein are based on this wild-type sequence.

FIG. 14 is the polynucleotide sequence encoding the wild-type PA protein used for the assays described herein (SEQ ID No.: 22).

FIG. 15 is an alignment of the amino acid sequence of PA (SEQ ID No.: 24) with other binary A-B toxins that have ADP ribosyltransferase activity. The amino acid sequences of toxins from *Clostridium difficile* ("cdADPRT"; SEQ ID No.: 25), *C. perfringens* ("cpiota"; SEQ ID No. :2 6), *C. spiroforme* ("csiota"; SEQ ID No.: 27), and *C. botulinum* ("cbc2"; SEQ ID No.: 28) are listed. The *C. Perfringens* and *C. Spiroforme* toxins are frequently referred to as iota toxins while the botulinum toxin is referred to as C2. Additionally, the alignment included the sequence of the toxin produced by *Bacillus cereus* ("VIP1"; SEQ ID No.: 29), which is frequently referred to as VIP for vegetative insecticide protein.

FIG. 16 is an alignment of the amino acid sequence of PA (SEQ ID No.: 30) with the amino acid sequences of toxins from *Clostridium difficile* ("cdADPRT"; SEQ ID No.: 31), *C. Perfringens* ("cpiota"; SEQ ID No.: 32), *C. Spiroforme* ("csiota"; SEQ ID No.: 33), *C. botulinum* ("cbc2"; SEQ ID No.: 34), and *Bacillus cereus* ("VIP1"; SEQ ID No.: 35). This alignment shows the complete sequences of the toxins.

DETAILED DESCRIPTION

Figure 1:
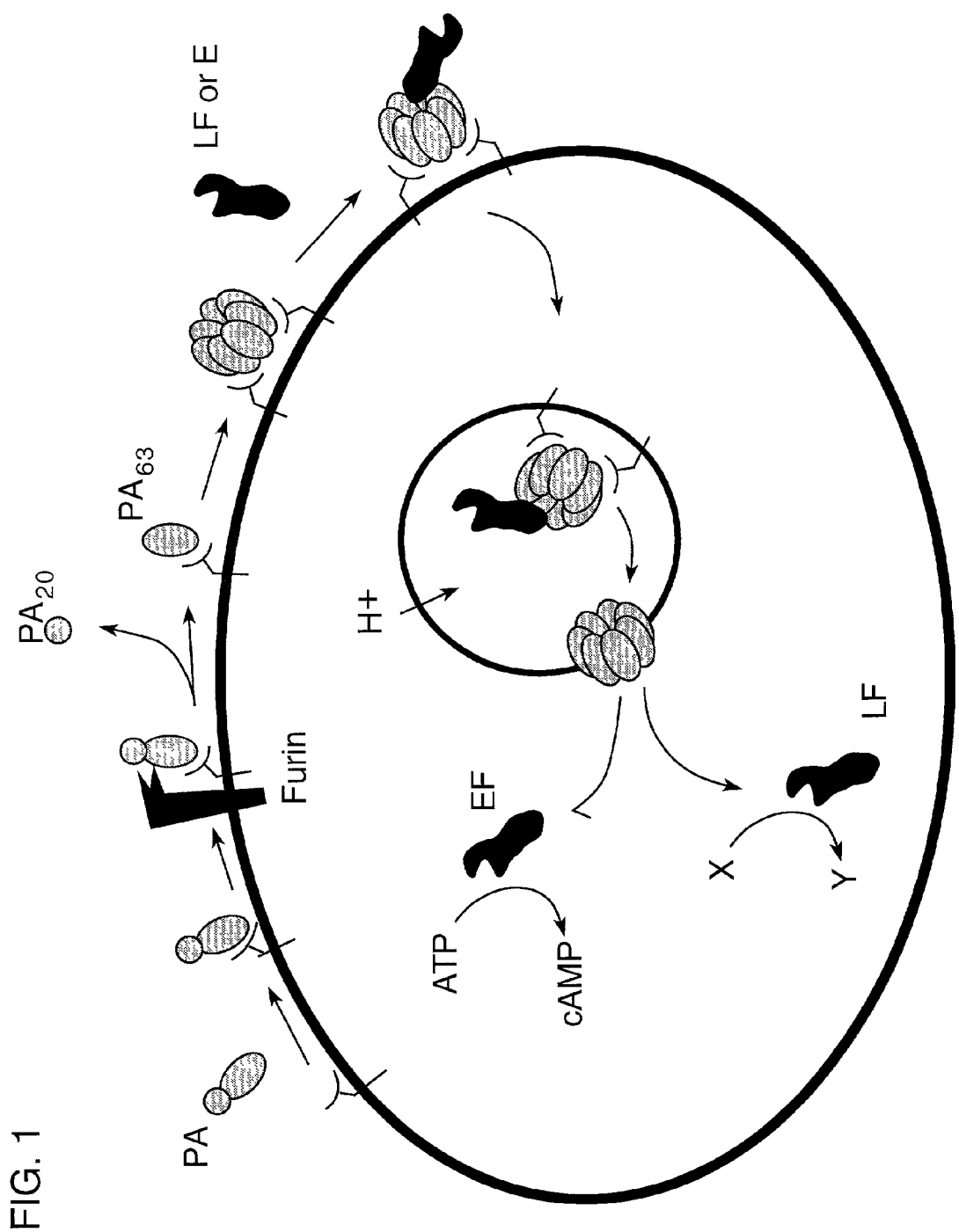
FIG. 1 is a schematic illustration of the intoxication pathway for ATx toxin. The PA component of ATx binds to a receptor on the surface of mammalian cells and delivers the enzymic A moieties of the toxin, edema factor (EF) and lethal factor (LF), to the cytosol, as described above.

We have found a means by which infection by A-B toxin producing bacteria can be halted. Thus, the invention provides a composition for use as an antidote to particular bacterial infections, including anthrax and gangrene. Because the composition is safe and immunogenic, it may also be used as a vaccine.

The multiple mutants of anthrax PA were constructed, expressed, purified, and assayed to determine whether they have reduced activity compared to wild-type PA. In particular, these mutants were assayed for the ability to bind PA ligands and receptors; to form prepores, SDS-resistant oligomers, and pores; and to translocate ligands across membranes. Based on the x-ray structure of PA, the mutated residues are predicted to project into the lumen of the PA prepore. PA mutants, or fragments thereof, with reduced or no detectable ability to form pores in membranes can be used as vaccines for the induction of protective antibodies to prevent anthrax infection. In addition, these mutants might be more effective than wild-type PA in treating anthrax infection because of their reduced ability to translocate EF and LF secreted by *Bacillus anthracis* in the infected mammal.

These point mutants and the previously reported deletion mutant lacking residues 302–325 of putative membrane spanning loop 2 of domain 2 (ΔD2L2) (Miller et al., Biochemistry 38:10432–10441, 1999) were further characterized to determine whether they could act as dominant negative inhibitors by reducing the pore formation of wild-type PA. This inhibition could result from the binding of ligands or receptors by the mutants so that fewer molecules were available for wild type PA to bind. The mutants could also form oligomers with wild-type PA that have reduced or no detectable ability to form pores and translocate ligands. Dominant negative PA mutants, and fragments thereof, could be used as vaccines to elicit protective antibodies for the prevention or treatment of anthrax infection, as described above. Additionally, mutants or fragments with dominant negative activity could be used as therapeutics to treat anthrax infection by inhibiting the activity of PA secreted by *Bacillus anthracis* in the infected mammal. Because dominant negative mutants can induce the production of protective antibodies and inhibit the activity of PA produced by the infecting bacteria, they can be used as a combination vaccine/therapeutic that is particularly effective in treating individuals suffering from, or at risk of developing, anthrax infection. Besides the need to abrogate toxin action as quickly as possible, it is also important to vaccinate individuals who have been exposed to aerosolized *B. anthracis* spores. This vaccination is essential to guard against delayed contraction of anthrax by germination of spores that can remain in the body for prolonged periods (at least a month).

In this study, several mutants of PA were identified that lack the ability to form pores in membranes and translocate ligands and, thus, are potential vaccines for the prevention or treatment of anthrax infection (Table 1). Mutants # 1–12 were able to be proteolytically activated, to form the SDS-dissociable PA63 prepore state, and to bind a cellular receptor, EF, and LF. Some of the mutations prevented the conversion of the prepore to an SDS-resistant state (Table 1). These mutants (K397A, K397C, K397D, D425A, D425N, D425K D425E, D425K, K397D+D425K, and K395D+ K397D+D425K+D426K) are also defective in pore formation and membrane translocation. The other class of mutants (ΔD2L2 PA, K397Q, and F427A) forms SDS-resistant oligomers but does not undergo membrane insertion and pore formation. These results were unexpected.

TABLE 1

Activity of Protective Antigen Mutants

| Mutant # | SEQ ID No. | Mutation | Forms SDS-resistant oligomer? | Forms channels? | Dominant negative? |
|---|---|---|---|---|---|
| 1 | 1 | K397A | No | No | No |
| 2 | 2 | K397D | No | No | No |
| 3 | 3 | K397C | No | No | No |
| 4 | 4 | K397Q | Yes | No | No |
| 5 | 5 | D425A | No | No | No |
| 6 | 6 | D425N | No | No | Not determined |
| 7 | 7 | D425E | No | No | No |
| 8 | 8 | D425K | No | No | Yes |
| 9 | 9 | F427A | Yes | No | Yes |
| 10 | 10 | K397D + D425K | No | No | Yes |
| 11 | 11 | K395D + K397D + D425K + D426K | No | No | Yes |
| 12 | 12 | ΔD2L2 | Yes | No | Yes |
| 13 | 13 | K397D + D425K + F427A | Not determined | Not determined | Yes |

TABLE 1-continued

Activity of Protective Antigen Mutants

| Mutant # | SEQ ID No. | Mutation | Forms SDS-resistant oligomer? | Forms channels? | Dominant negative? |
|---|---|---|---|---|---|
| 14 | 14 | F427A + ΔD2L2 | Not determined | Not determined | Yes |
| 15 | 15 | K397D + F427A + ΔD2L2 | Not determined | Not determined | Yes |
| 16 | 16 | K397D + D425K + F427A + ΔD2L2 | Not determined | Not determined | Yes |
| 17 | 17 | F427D | Not determined | Not determined | Yes |
| 18 | 18 | F427K | Not determined | Not determined | Yes |

These PA mutants were constructed as described in Example 1.

Several of the mutants (ΔD2L2, K397D+D425K double mutant, K395D+K397D+D425K+D426K quadruple mutant, D425K, F427A, K397D+D425K+F427A triple mutant, F427A+ΔD2L2 double mutant, K397D+F427A+ΔD2L2 triple mutant, K397D+D425K+F427A+ΔD2L2 quadruple mutant, F427D, and F427K) inhibit the wild-type PA-mediated translocation of ligands across membranes. The ΔD2L2 and K397D+D425K PA mutants were shown to form oligomers with wild-type PA that are unable to translocate ligands. These results were unexpected. The presence of a single molecule of these mutants within a heptameric prepore may be sufficient to block conversion to the pore. This ability to block the pore formation by wild-type PA, coupled with the ability to compete with wild-type PA for the binding of cellular receptors and to remove EF and LF from circulation, makes these mutants particularly attractive for use in the treatment and prevention of anthrax infection.

Mutation of other residues in PA could also inhibit pore formation or produce dominant negative activity. For example, residues that electrostatically interact with the charged side-chains of Lys397 or Asp425 may also be required for pore formation by PA, and the mutation of one or a combination of these residues may inhibit pore formation and result in dominant negative activity. Additionally, the deletion of smaller portions of the 302–325 D2L2 loop or the deletion of amino acids flanking the loop and part or all of the 302–325 region could produce these results.

The ability to obtain mutants of PA with no detectable ability to form pores or translocate ligands and mutants that serve as dominant negative inhibitors of wild-type PA suggests that similar mutants could be obtained in other toxins, such as α-hemolysin from *Staphylococcus aureus*, aerolysin from *Aeromonas hydrophila*, α-toxin from *Clostridium septicum*, cytotoxin from *Pseudomonas aeruginosa*, hetero-oligomeric toxins (AB5 toxins), or in the B moieties of tetanus, botulinum, or diphtheria toxins. Additionally, these results underscore the possibility of identifying dominant negative forms of a number of other oligomeric virulence factors, ranging from toxins to adhesins.

In anthrax toxin and other oligomeric systems in which the assembly process occurs in contact with the extracellular milieu, exogenously added mutant subunits can in principle be incorporated into the final structure, raising the possibility that such subunits could be used therapeutically. Systemic anthrax, although rare as a natural disease, is feared as an agent of biological warfare and terrorism, and dominant negative PA would seem to be a worthy candidate for a therapeutic. Assuming that administered dominant negative PA intermixes freely with wild-type PA produced in the body by *B. anthracis*, the proteins should co-assemble on cells to form inactive, dead-end complexes, thereby blocking the actions of both LF and EF. Besides preventing overt symptoms, dominant negative mutants may also protect professional phagocytes from destruction, thereby aiding the host in eradicating the infection. No significant side effects have been observed following injection of wild-type PA into humans, and thus a mutant inactive form of the protein should pose no hazard.

Dominant negative PA may also be useful as a basis for a new vaccine against anthrax. As its name connotes, PA induces protective antibodies against anthrax, and indeed is the major immunogen of the vaccine currently licensed in the United States. The ΔD2L2, K397D+D425K, and F427A mutants described herein exhibit little or no diminution in immunogenicity relative to wild-type PA in Fisher rats. We have also found mutants that are unexpectedly dominant negative, such that administration of a 0.25:1 ratio of mutant to wild-type PA did not result in any detectable symptoms of anthrax infection in a rat model. Purified wild-type PA is under consideration as a replacement for the currently licensed vaccine, and if a dominant negative form of PA proves efficacious therapeutically, it might fulfill this role as well, eliminating the need to develop two almost identical pharmaceuticals.

The following examples are to illustrate the invention. They are not meant to limit the invention in any way. Unless otherwise noted, the data for the K397A and D425A PA mutants is representative of the data obtained for PA mutants number 1–12 listed in Table 1.

EXAMPLE 1

General Methods

Cell Culture, Media and Chemicals

Chinese hamster ovary-K1 (CHO-K1) cells were obtained from American type culture collection. The cells were grown in HAM's F-12 supplemented with 10% calf serum, 500 units/mL penicillin G, 2 mM L-glutamine and 500 units/mL streptomycin sulfate and maintained at 5% $CO_2$ in a humidified atmosphere. Cells were seeded into 24- or 96-well microtiter plates (Costar, Cambridge, Mass.) 16–18 hours prior to the experiment. All media for cell culture was obtained from Gibco BRL unless noted otherwise. All chemicals were obtained from Sigma Chemical Co. unless specified.

Construction and Purification of PA Proteins

The ΔD2L2 PA mutant, which does not contain amino acids 302–325 of PA, was expressed and purified as described previously (Miller et al., Biochemistry 38:10432–10441, 1999). The point mutations # 1–11 from Table 1 were constructed using the QuickChange method of site directed mutagenesis, following the manufacturer's protocol (Stratagene, La Jolla, Calif.). The plasmid of Miller et al. (supra) encoding wild-type PA was used as the template. The point mutants were cloned into a pET22-b(+) (Novagen) expression vector and transformed into BL21 (DE3) (Novagen) for expression. The point mutants were expressed and purified as previously described (Miller, 1999). Briefly, cultures were grown in LB at 37° C. to an $A_{600}$ of 1.0. Expression of the recombinant protein was induced by the addition of β-D-isopropylthiogalactopyranoside to 1 mM. Following induction, the cells were grown for an additional 3 hours at 30° C. and harvested by centrifugation for 10 minutes at 8000×g.

The proteins were released from the periplasm by osmotic shock. The cells were resuspended in 20 mM Tris-HCl, pH 8.0, 30% glucose and 1 mM EDTA and incubated at room temperature for 10 minutes with continuous stirring. The cells were harvested again by centrifugation, resuspended in 5 mM $MgSO_4$ containing 20 mM Benzamidine. and incubated at 4° C. for 10 minutes with constant stirring. After the cells were again pelleted by centrifugation at 8000×g, the perplasmic extract was decanted. Tris-HCL pH 8.0 was added to a final concentration of 20 mM, and the entire sample was loaded onto a Q sepharose HP column. The unbound protein was washed off the column with buffer A (20 mM Tris, pH 8.0). The bound protein was eluted with a 0%–25% buffer B linear gradient (20 mM Tris, pH 8.0, 1 M NaCl). The PA containing fractions were concentrated, and the buffer was exchanged using a pd-10 column (Amersham-Pharmacia) containing buffer A. The PA-containing eluate was loaded onto a Mono-Q column and eluted with a 0–25% buffer B gradient. PA containing fractions were analyzed by SDS-PAGE and stored at −80° C. Proteins concentrations were determined using the Bio-Rad protein assay kit based on the manufacturer's protocol. All liquid chromatography was performed using an AKTA-purifier liquid chromatography system (Amersham-Pharmacia).

The other PA mutants (# 13–18 from Table 1) were constructed, expressed, and purified similarly.

Proteolytic Activation of PA

Trypsin was used to proteolytically cleave PA83 to nicked PA (nPA). PA was diluted to a concentration of 0.5 mg/ml for the prepore-forming assay or 0.2 mg/ml for the other assays. Trypsin was added to a final trypsin to PA ratio of 1:1,000 (w:w), and the mixture was incubated at room temperature for 20 minutes, followed by inhibition of the trypsin with a 10 molar excess of soybean trypsin inhibitor.

Cell Surface Translocation Assay

A cell surface translocation assay to measure the PA-mediated translocation of radiolabeled LFn (N-terminal 1–255 amino acid PA binding domain of LF) was performed as previously described (Wesche et al., Biochemistry 37:15737, 1998). Briefly, nPA ($2×10^{-8}$ M) was first bound to CHO cells, followed by $^{35}S$ LFn which binds to the PA63 on the cell surface. Excess LFn was removed, and the cells were washed and subjected to a pH 5.0 pulse at 37° C. The low pH pulse mimics the acidification of the endosome and results in the PA-mediated translocation of LFn across the plasma membrane and into the cell. The samples were treated with pronase which proteolytically degrades extracellular $^{35}S$-LFn, but not $^{35}S$-LFn that has been translocated into the cell. The cells were then washed and lysed. To determine the total amount of $^{35}S$-LFn that bound to the cells, some of the cells were not treated with pronase. Following lysis, the amount of $^{35}S$-LFn in the supernatant was determined using a scintillation counter. The percent translocation was calculated as follows: (DPM protected from pronase)/(DPM bound to cells)×100=% translocated.

To determine if mutant PA proteins inhibit the translocation of LFn by wild-type PA, this assay was also performed using equimolar amounts of mutant and wild-type PA that were combined prior to trypsinization and diluted to $2×10^{-8}$ M PA ($1×10^{-8}$ M of each protein) before being added to cells. When PA at a concentration of $1×10^{-8}$ M was used as a control, the translocation efficiency was only slightly affected by the drop in PA compared to the assay above with $2×10^{-8}$ M wild-type PA, suggesting that any decrease in translocation and binding was not the result of the drop in the concentration of wild-type PA.

Inhibition of Protein Synthesis

LFnDTA inhibition of protein synthesis was used as another method to measure PA-mediated translocation of ligands into cells (Milne et al., Mol. Microbiol. 15:66, 1995). For assaying PA mutants # 1–12 in Table 1, CHO-K1 cells were plated at $2.5×10^4$ cells/well in a 96 well plate 16 hours prior to the addition of PA protein. PA83 ($1×10^{-12}$ M to $1×10^{-7}$ M) was incubated with cells in the presence of $1×10^{-8}$ M LFnDTA for 4 hours. The media was then removed and replaced with leucine free HAM's F-12 media supplemented with $^3$H-Leu at 1 mCi/ml. After a one hour incubation, the cells were washed with ice cold PBS followed by ice-cold trichloro acetic acid (10%) to precipitate proteins. The quantity of $^3$H-leu incorporated into the TCA insoluble material was determined using a scintillation counter and was used as a measure of the amount of newly synthesized protein.

Mutant PA proteins were also tested in this assay to see if they relieved the wild-type PA-mediated inhibition of $^3$H-Leu uptake. Wild-type PA was added to CHO cells at a concentration of $1×10^{-9}$ M with $1×10^{-8}$ M LFnDTA. Increasing amounts of one of the mutants were also added. The cells were incubated with the toxin for 4 hours and the samples were processed as described above.

Figure 9:
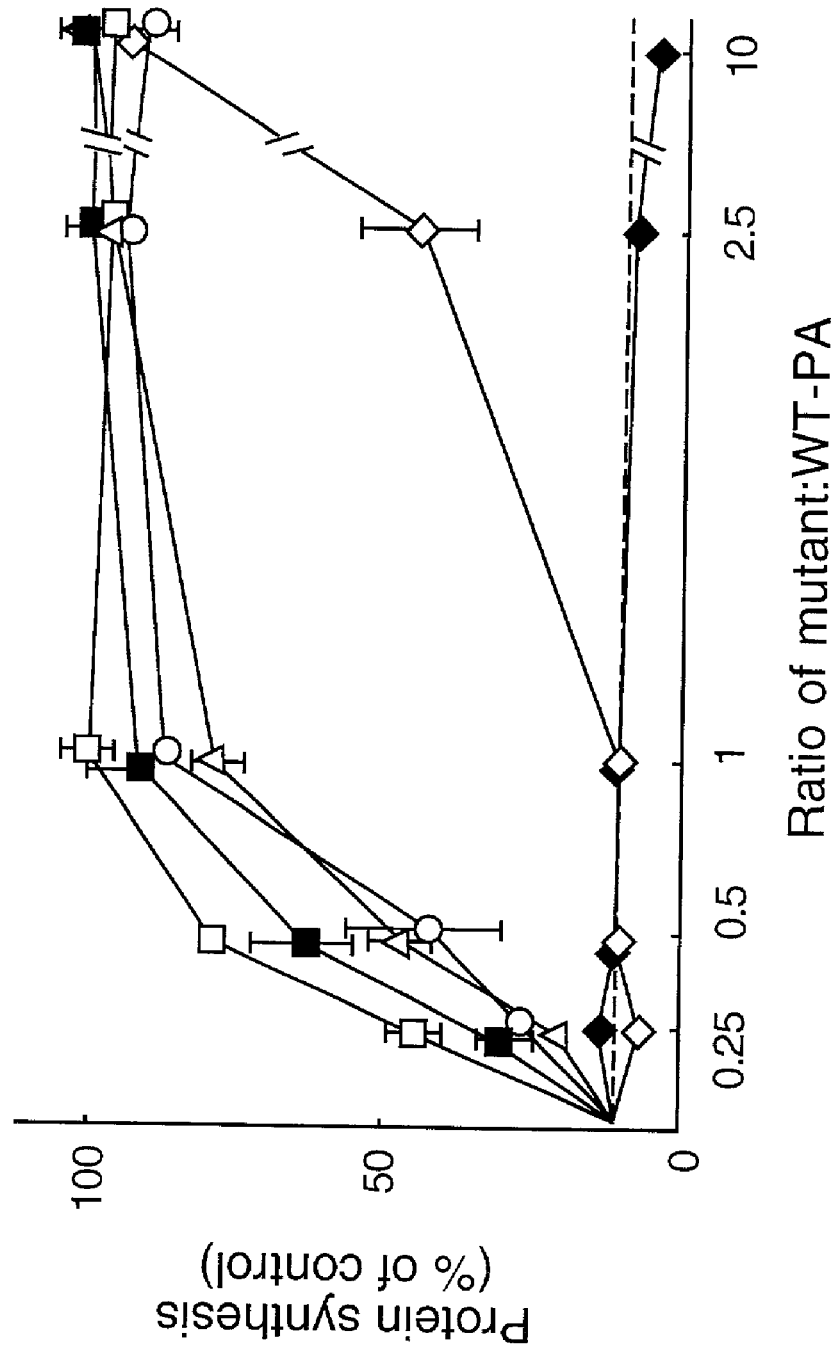
FIG. 9 is a graph showing the decrease in wild-type PA-mediated inhibition of protein synthesis in the LFnDTA toxicity assay due to the presence of increasing concentrations of a dominant negative PA mutant. The effect of the dominant negative mutants K397D+D425K (□), ΔD2L2 (■), F427A (○), D425K (Δ), and K397D (◊) and the control mutant SSSR (♦) are shown in this figure.
Figure 10:
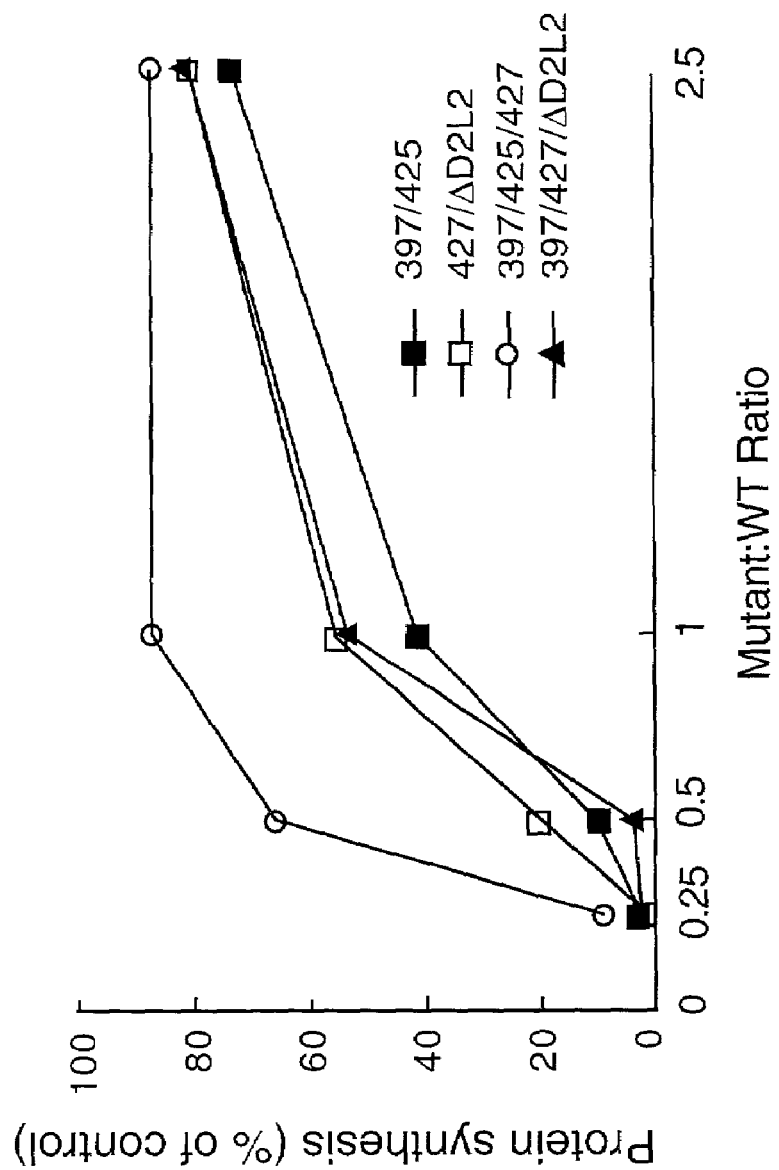
FIG. 10 is a graph showing the decrease in wild-type PA-mediated inhibition of protein synthesis in the LFnDTA toxicity assay due to the presence of increasing concentrations of one of the following dominant negative PA mutants: K397D+D425K (■), F427A+ΔD2L2 (□), K397D+D425K+F427A (○), and K397D+F427A+ΔD2L2 (▲).

The PA mutants listed in FIG. 9 were tested similarly. CHO-K1 cells ($2.5×10^4$ cells/well) in a 96-well plate were incubated for 18 hours at 37° C. with wild-type PA (100 pM) in the presence of LFN-DTA (100 pM) and various amounts of individual PA mutants (K397D+D425K, ΔD2L2, F427A, D425K, K397D, or SSSR). The medium was then removed and replaced with leucine-free HAM F-12 supplemented $^3$H-Leu at 1 μCi/ml. After incubation for one hour at 37° C., the cells were washed with ice-cold PBS followed by ice-cold 10% trichloroacetic acid (TCA). The quantity of $^3$H-Leu incorporated into the TCA-precipitable material was measured and is expressed as percent of that incorporated in the absence of PA. At the concentrations of wild-type PA and LFnDTA chosen, protein synthesis was inhibited by about 90% in the absence of mutant PA (dotted line). The mean of three experiments ±SEM is reported. Similar results were seen when the initial incubation was four hours, instead of 18 hours. The K397D+D425K+F427A, F427A+ΔD2L2, and K397D+F427A+ΔD2L2 PA mutants listed in FIG. 10 were tested similarly.

Figure 11:
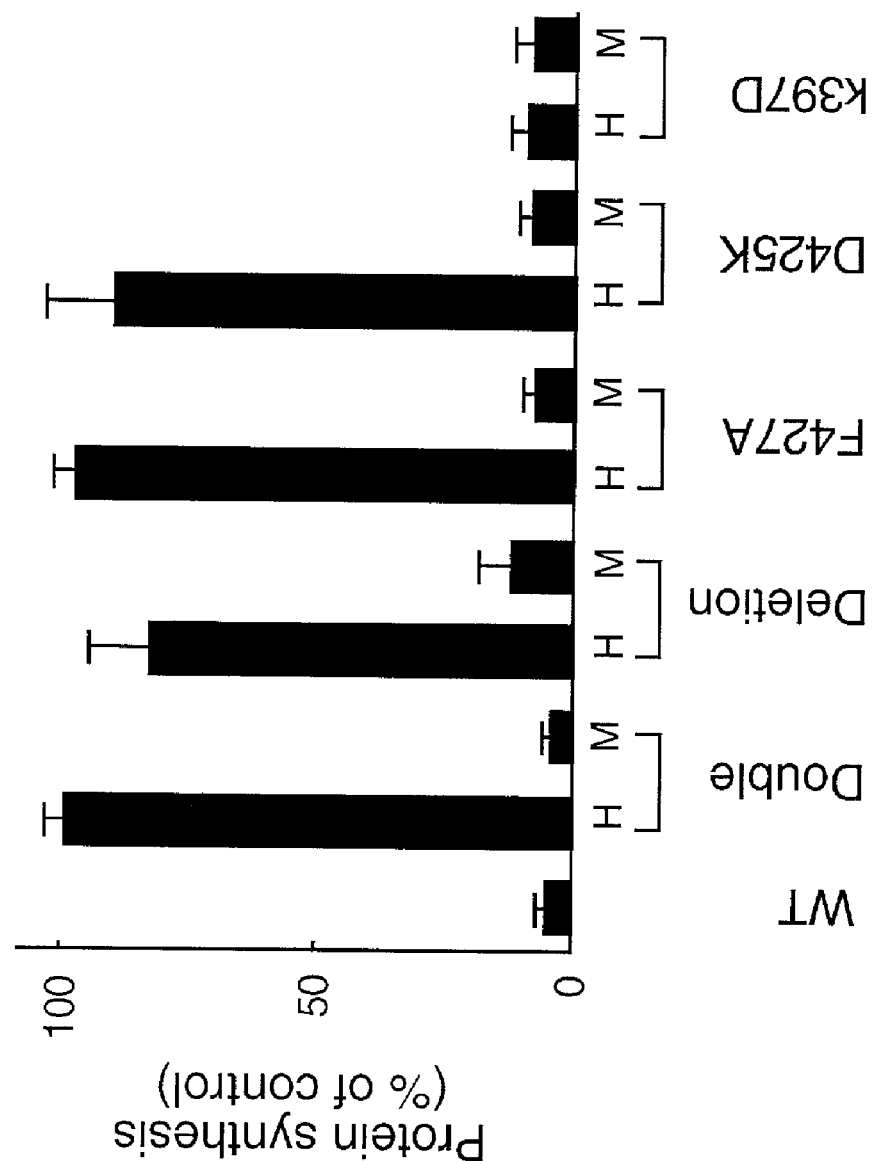
FIG. 11 is a bar graph showing the inhibition of protein synthesis by a hetero-heptamer formed by mixing wild-type PA with a mutant PA (K397D+D425K, ΔD2L2, F427A, or D425K) and then cleaving the PA molecules with trypsin. Inhibition of protein synthesis by an equivalent amount of a 1:1 mixture of the corresponding mutant and wild-type homo-heptamers was also measured.

The PA-mediated inhibition of protein synthesis by hetero-heptamers of wild-type and mutant PA was compared to that of mixtures of the corresponding homo-heptamers. Homo-heptamers of wild-type PA63 and K397D+D425K, ΔD2L2, F427A, K397D, and D425K mutants, were prepared as described above. Putative hetero-heptamers were prepared by mixing each mutant PA with wild-type PA in a 1:1 ratio before trypsinization and column chromatography (FIG. 11). Wild-type PA (1 nM), hetero-heptamer (H) (final concentration 2 nM), or an equimolar mixture (M) (1 nM each) of the corresponding mutant homo-heptamer and wild-type-heptamer, was incubated with CHO-K1 cells in the presence of LFnDTA (100 pM) for 18 hours, and inhibition of protein synthesis was measured as described above for FIG. 9. Heptamer concentrations are expressed in terms of monomeric PA63 sub units. Protein synthesis is expressed as the percent of a control without PA. The mean of three experiments ±SEM is reported. Similar results were seen after a four hour incubation.

Prepore and SDS-resistant Oligomer Formation

The formation of prepores and SDS-resistant oligomers was measured by incubating nPA with an equimolar amount of LFn for 30 minutes at room temperature. To determine whether prepores had formed, the samples were subjected to electrophoresis in a 4–12% native gradient gel (FMC) using 50 mM CHES, pH 9.0, 2 mg/ml CHAPS as the running buffer. To determine whether low pH induced the formation of SDS-resistant heptamers, 100 mM sodium acetate, pH 4.5 was added until the pH of the solution reached 5.0, and then the sample was incubated at room temperature for 30 minutes. The sample was then dissolved in SDS-PAGE sample buffer and run on a 4–12% SDS-PAGE gradient gel. Proteins in the gels were visualized with coomassie brilliant blue.

Rubidium Release

CHO-K1 cells were plated at a density of $2 \times 10^5$ cells/well and incubated at 37° C. for 24 hours. The media was then aspirated and replaced with media containing 1 µCi/ml $^6$RbCl and incubated for 16 hours. The cells were chilled on ice for 20 minutes, and the media was removed. The cells were washed, and nPA ($2 \times 10^{-8}$ M) in HEPES buffered media was added. The cells were incubated with nPA for 2 hours on ice, followed by the addition of ice cold pH 5.0 buffer. After 30 minutes, samples from the supernatant were collected and counted in a scintillation counter to determine the amount of released $^{86}$Rb.

This standard assay may also be used to determine the effect of other pore-forming toxins on the amount of released $^{86}$Rb. Thus, other mutant toxins of the present invention may be tested in this assay to determine whether they have a reduced ability to form transmembrane pores.

EXAMPLE 2

Failure of Most Mutants to Form SDS-resistant Oligomers

Figure 2A:
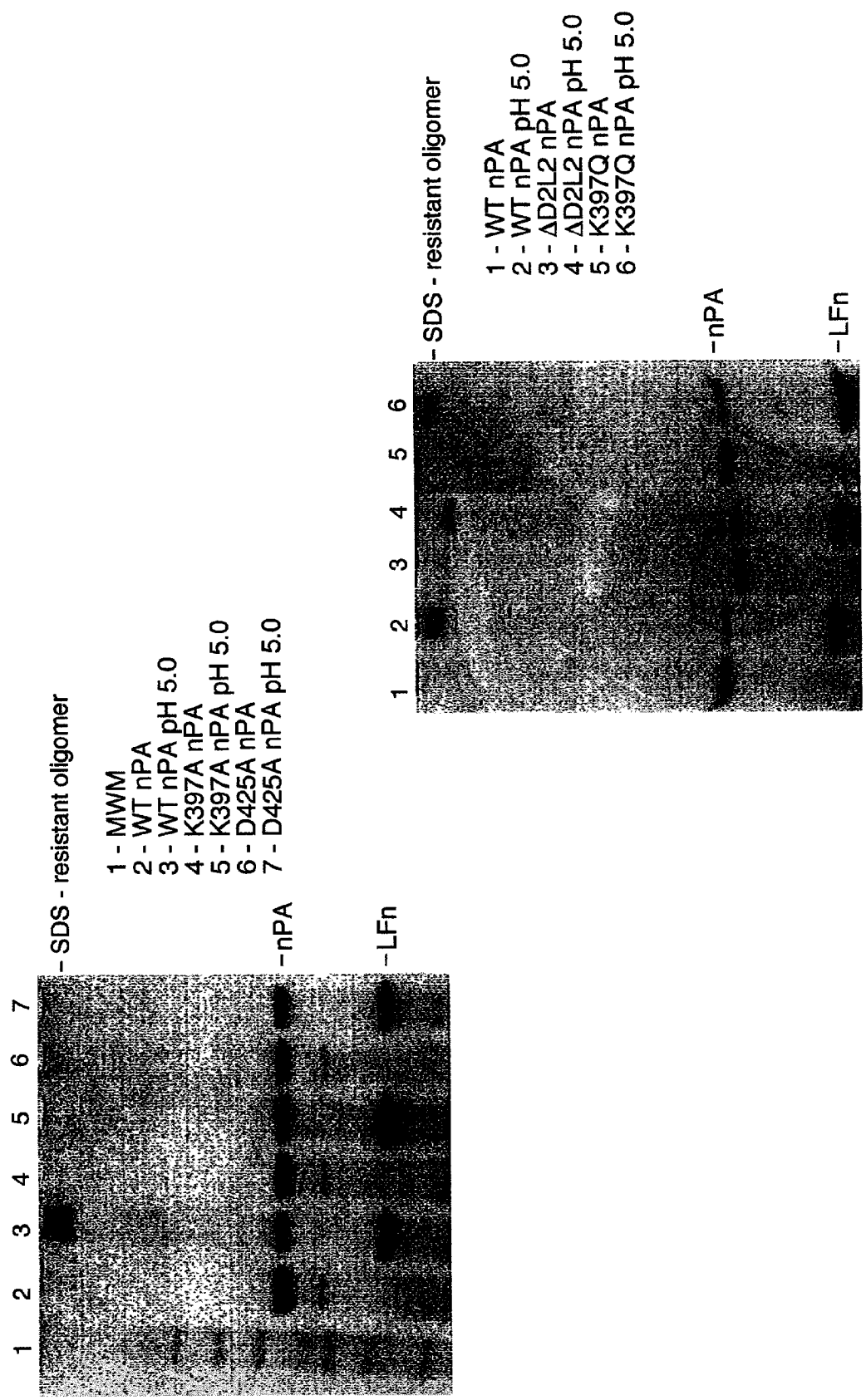
FIG. 2A is a picture of SDS-PAGE gels showing the formation of nicked PA mutant proteins and the formation of SDS-resistant oligomers by wild-type, K397Q, and ΔD2L2 PA.
Figure 2B:
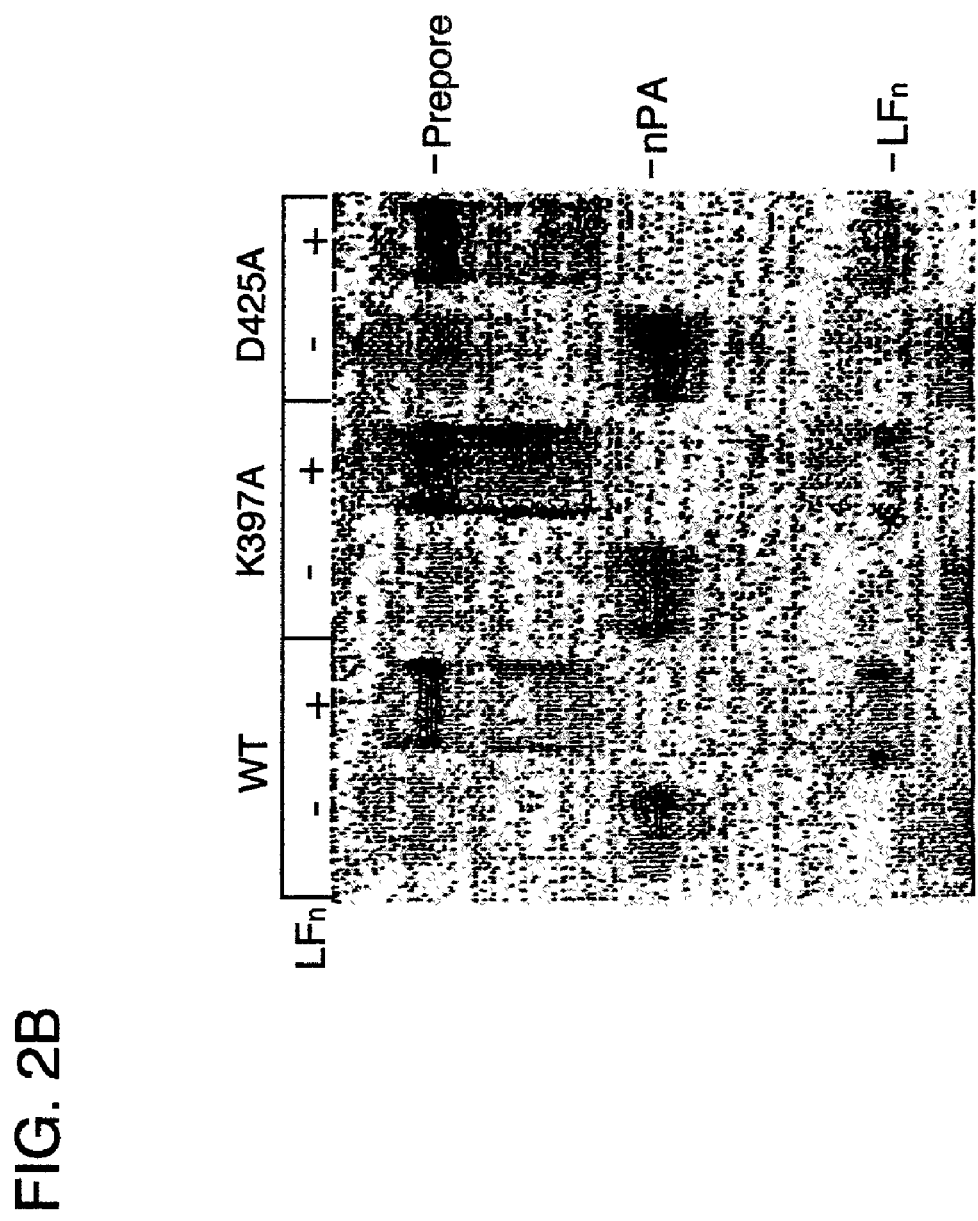
FIG. 2B is a picture of a native gel showing the formation of prepores by wild-type, K397A, and D425A PA.

All PA mutants # 1–12 in Table 1 and wild type PA proteins were proteolytically nicked with trypsin as described above, forming nicked PA (nPA) proteins that migrated as lower molecular species when analyzed by SDS-PAGE (FIG. 2A). Formation of SDS-dissociable prepores by PA mutants # 1–12 in Table 1 was detected by the decreased mobility in native gels of heptameric PA63 complexed with LFn compared to monomeric nPA (FIG. 2B). The formation of prepores by the K397A and D425A PA mutants was further supported by the elution of the prepores from a MonoQ column at a higher salt concentration than that which elutes monomeric PA. The nPA mutants were also analyzed for the formation of SDS-resistant oligomers. As a positive control, wild-type PA was treated with LFn. The low pH pulse converted wild-type PA into SDS-resistant oligomers, which migrated as high molecular weight complexes when analyzed by SDS-PAGE. ΔD2L2 (PA lacking residues 302–325) and K397Q (FIG. 2B). Wild-type, K397Q, F427A, and ΔD2L2 PA formed SDS-resistant oligomers when treated with low pH (FIG. 2A and Table 1).

EXAMPLE 3

Failure of PA Mutants to Form Pores in Membranes

Figure 3:
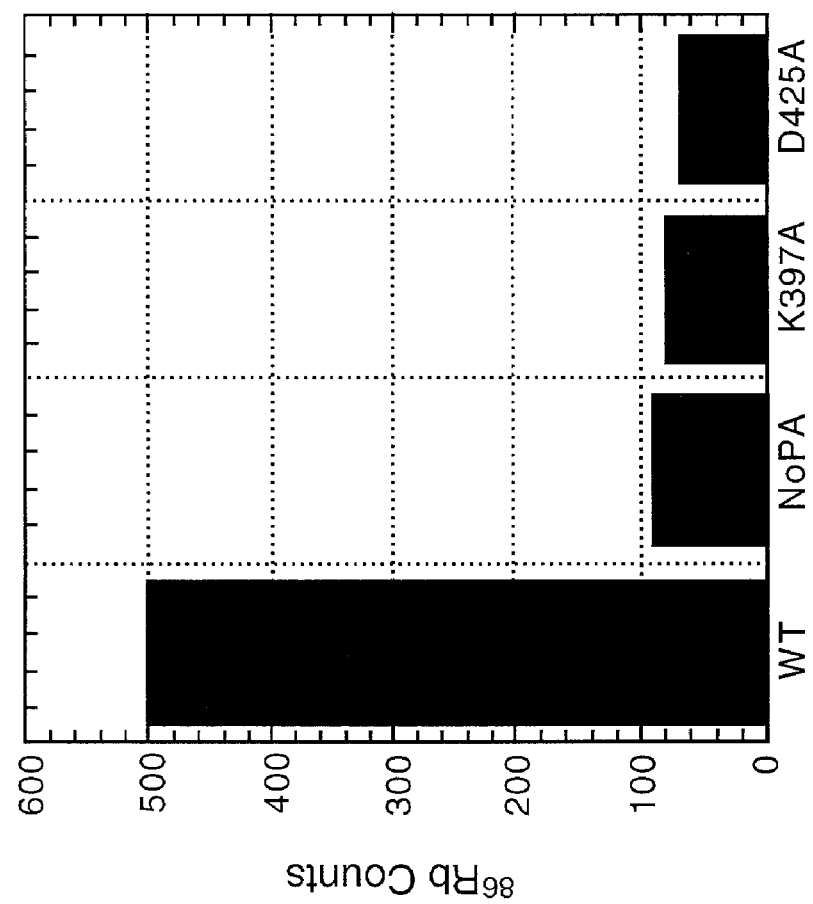
FIG. 3 is a bar graph showing the amount of $^{86}$Rb released from $^{86}$RB loaded cells after incubation with wild-type, K397A, or D425A PA compared to the no PA control.

The failure of most of the PA mutants to form SDS-resistant oligomers suggested that pore formation in cell membranes would also be inhibited. Pore formation was assayed by binding nPA proteins to cells loaded with the radioactive potassium analogue, $^{86}$Rb, pulsing with low pH, and measuring the release of $^{86}$Rb into the surrounding media, as described in Example 1. Wild-type nPA induced the release of $^{86}$Rb due to the insertion of nPA into the membrane forming ion permeable pores. In contrast, none of the mutants # 1–12 in Table 1 induced $^{86}$Rb release (FIG. 3 and Table 1). Thus, the inability of most PA mutants to form SDS-resistant oligomers (Example 2) correlates with an inability of these mutants to form pores in cell membranes.

EXAMPLE 4

Failure of PA Mutants to Translocate LFn Across Membranes

Figure 4:
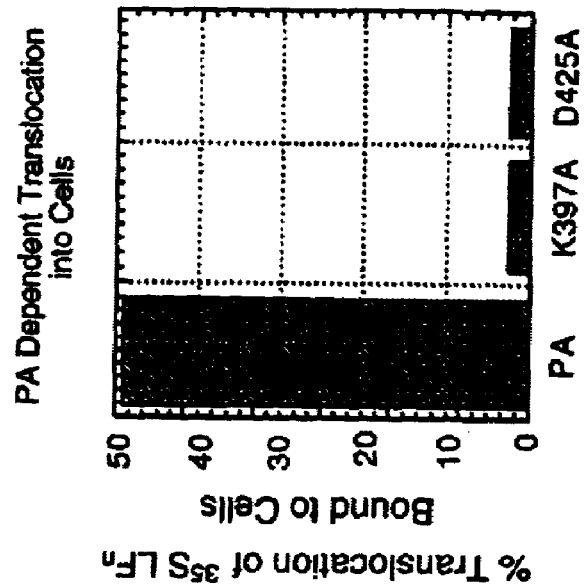
FIG. 4A is a bar graph showing the similar level of $^{35}$S-LFn (N-terminal 1–255 amino acid PA binding domain of LF) binding by cells that have been incubated with wild-type, K397A, or D425A PA.
FIG. 4B is a graph showing the reduction in translocation of $^{35}$S-LFn into cells that is mediated by K397A or D425A PA compared to wild-type PA.
Figure 4:
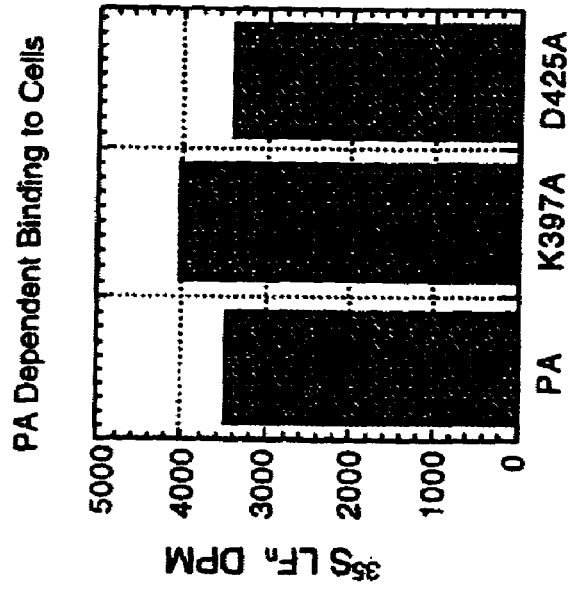
Figure 12:
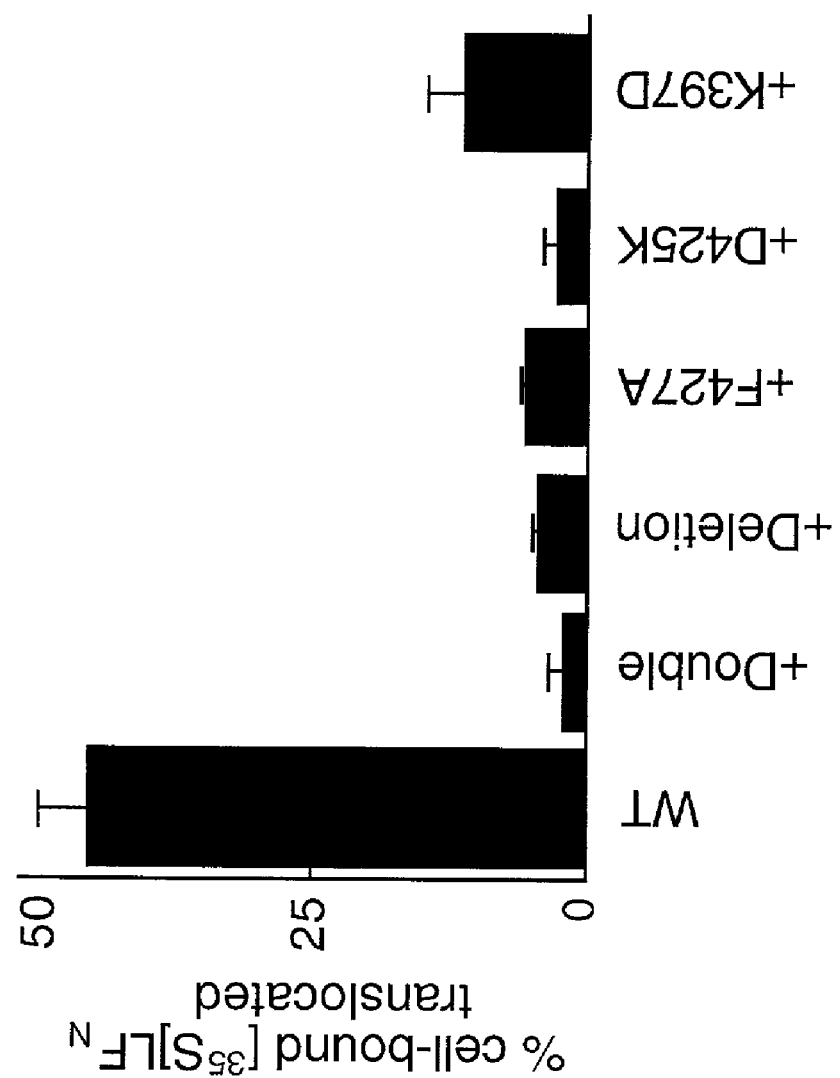
FIG. 12 is a bar graph showing the effect of the dominant negative mutants K397D+D425K, ΔD2L2, F427A, and D425K on the low-pH triggered translocation of $^{35}$S LFN across the plasma membrane. The results presented are the mean of three experiments ±SEM.

Pore formation is a requisite step in the PA dependent translocation of ligands (i.e., LF, EF or LFn) across membranes. A cell surface translocation assay was used to directly measure the translocation of PA ligands into the cytoplasm of the cell (Example 1). None of the PA mutants # 1–12 in Table 1 had a significantly decreased ability to bind LFn (FIG. 4A); however, all of the assayed mutants had a significantly reduced ability to translocate LFn in this assay (FIGS. 4B and 12). The SSSR control mutant caused little inhibition under these conditions. These data suggest that the mutants retain structural integrity and the ability to bind to the cellular receptor and LFn but are not able to form pores or translocate ligands across membranes.

EXAMPLE 5

Failure of PA Mutants to Translocate LFnDTA Across Membranes

Figure 5:
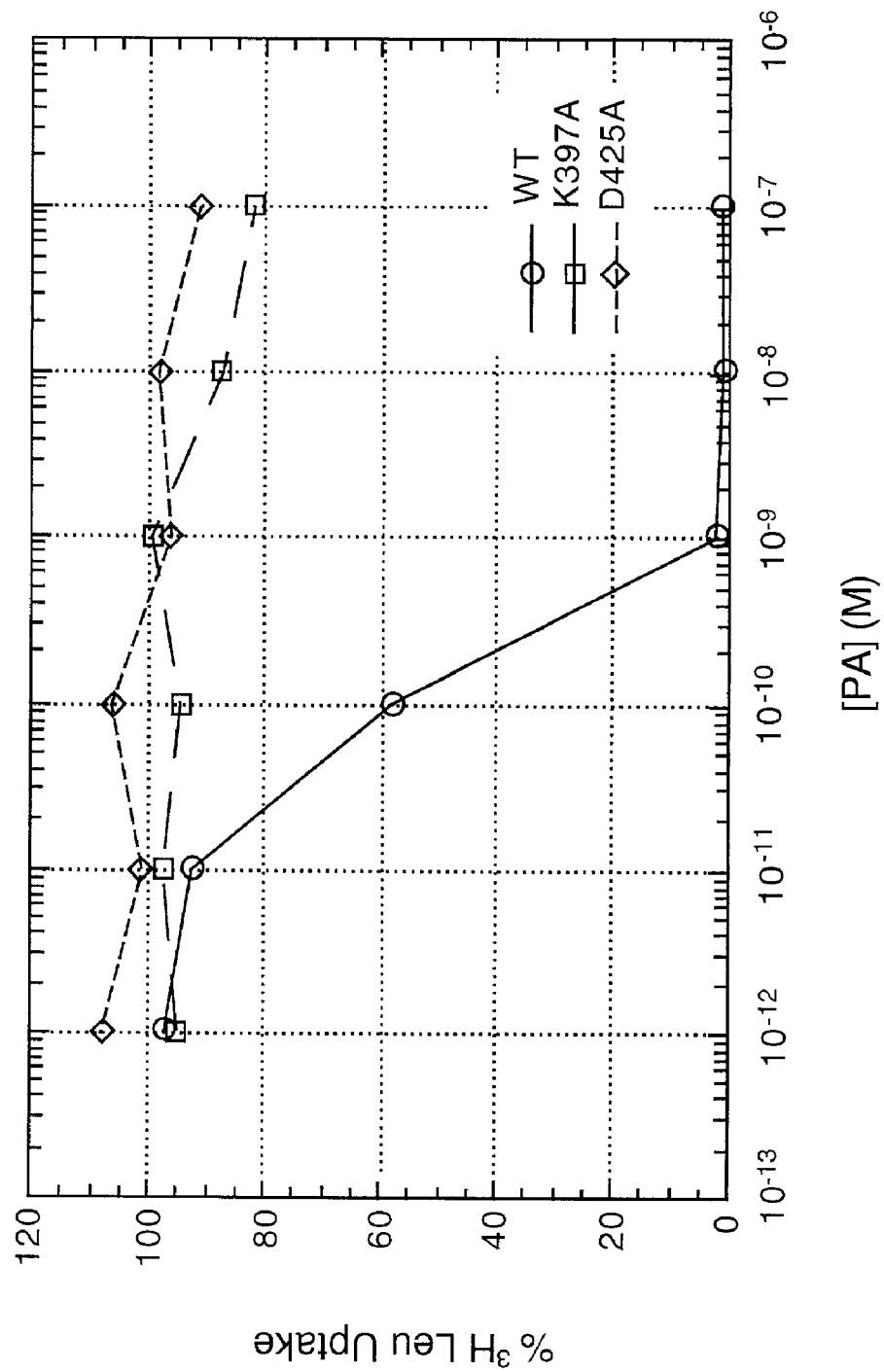
FIG. 5 is a graph showing the percent of $^3$H-Leu in the TCA insoluble fraction (protein fraction) after incubation of cells with wild-type, K397A, or D425A PA in the LFnDTA toxicity assay. Translocation of LFnDTA, which contains LFn fused to the A-chain of diptheria toxin, into the cell leads to ribosylation of EF-2, resulting in the inhibition of protein synthesis and a decrease in the amount of $^3$H-Leu in the protein fraction.

Another method used to measure translocation of PA ligands across membranes is the LFnDTA toxicity assay (Example 1). In this assay, CHO cells are treated with PA and a ligand containing LFn fused to the A-chain of diphtheria toxin DTA (LFnDTA). The translocated A-chain of diphtheria toxin ADP ribosylates the cytoplasmic protein EF-2, resulting in the inhibition of protein synthesis and the induction of cell death. This assay is a measure of translocation of a ligand from an endosomal compartment as opposed to a cell surface, as measured in Example 4. After incubation with LFnDTA and wild-type or mutant PA, cells were washed and incubated in leucine-free media supplemented with $^3$H-leucine. If protein synthesis is not inhibited, $^3$H-leucine will be incorporated into newly synthesized proteins. If protein synthesis is inhibited by LFnDTA, little $^3$H will be incorporated. All of the mutants tested did not significantly inhibit protein synthesis in this assay (FIG. 5). This result further supports the hypothesis that the lack of significant pore formation by PA mutants results in decreased membrane translocation of PA ligands by these mutants.

EXAMPLE 6

Inhibition of Wild-type PA Pore Formation by PA Mutants

Figure 6A:
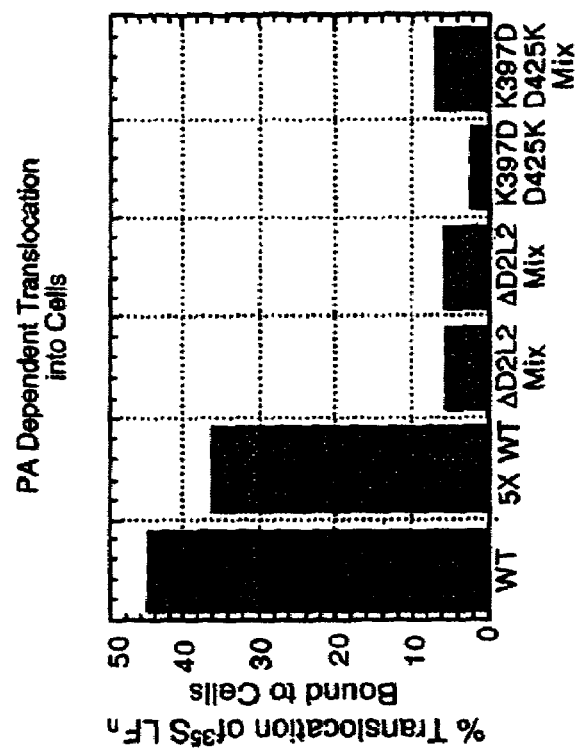
FIG. 6A is a bar graph showing the similar binding of $^{35}$S-LFn to cells incubated with wild-type, ΔD2L2, the double mutant K397D+D425K, or a mixture of wild-type and ΔD2L2 or K397D+D425K PA.
Figure 6B:
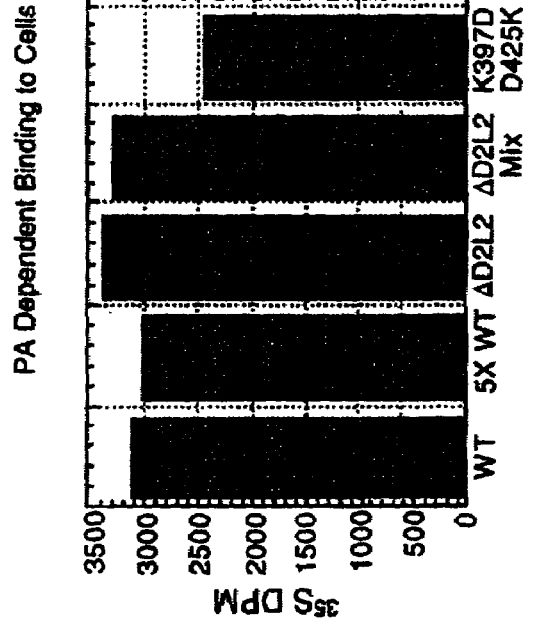
FIG. 6B is a bar graph showing the reduction of wild-type PA-mediated translocation of $^{35}$S-LFn by ΔD2L2 or K397D+D425K PA.

Since all of the PA mutants # 1–12 in Table 1 were defective in pore formation, they were tested to determine whether they could form inactive hetero-oligomers with wild-type PA thus inhibiting PA-mediated translocation of ligands across membranes. ΔD2L2, K397D+D425K, and K395D+K397D+D425K+D426K PA inhibited wild-type PA in this manner. When mixed with an equimolar amount of wild-type PA, each of these three mutants markedly inhibited translocation of $^{35}$S-LFn into the cells in the cell surface translocation assay (FIG. 6). $^{35}$S-LFn binding to cells was not inhibited (FIG. 6).

EXAMPLE 7

Inhibition of Wild-type PA Pore Formation by PA Mutants

Figure 7:
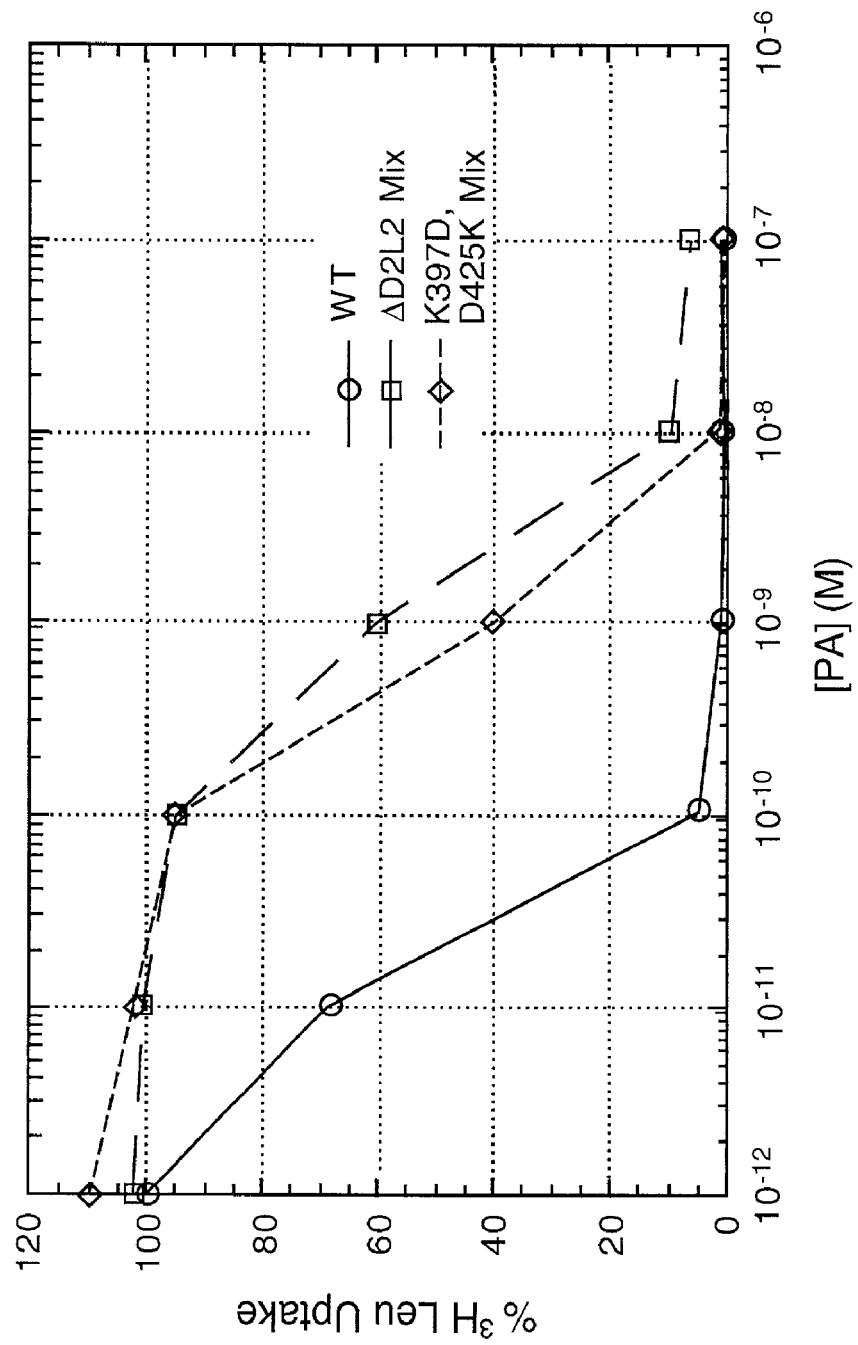
FIG. 7 is a graph showing the higher percent of $^3$H-Leu in the TCA insoluble fraction after incubation of ΔD2L2 or K397D+D425K PA and wild-type PA compared to wild-type PA alone. This result corresponds to a decrease in wild-type PA-mediated inhibition of protein synthesis in the LFnDTA toxicity assay.

The effect of these mutant proteins on PA mediated LFnDTA toxicity was also measured. When the ΔD2L2, K397D+D425K double mutant, or K395D+K397D+D425K+D426K quadruple mutant PA was mixed with an equimolar amount of wild-type PA in the LFnDTA assay, there was an approximately 2-log decrease in the wild-type PA-mediated inhibition of $^3$H-Leu (FIG. 7). Thus, the mutants inhibited PA-mediated translocation by 99%. The activity retained in the presence of the mutant proteins is probably the result of heptamers containing 7 wild-type PA molecules and 0 mutant PA molecules (WT$_7$Mut$_0$). Using Pascal's triangle, 1% of the heptamers formed from the equimolar mixture of wild-type and mutant PA are expected to be 100% wild-type (WT$_7$Mut$_0$) (Table 2). This calculated result agrees with the 1% experimentally measured residual activity present in the mixture. Inhibition studies in which various ratios of wild-type to ΔD2L2 or K397D+D425K mutant PA were tested in the LFnDTA assay indicate that the only active species in the mix is probably WT$_7$Mut$_0$. Thus, the majority of heptamers containing one molecule of ΔD2L2 or K397D+D425K PA are inactive (Table 2), further supporting the dominant negative nature of these inhibitors.

Figure 8A:
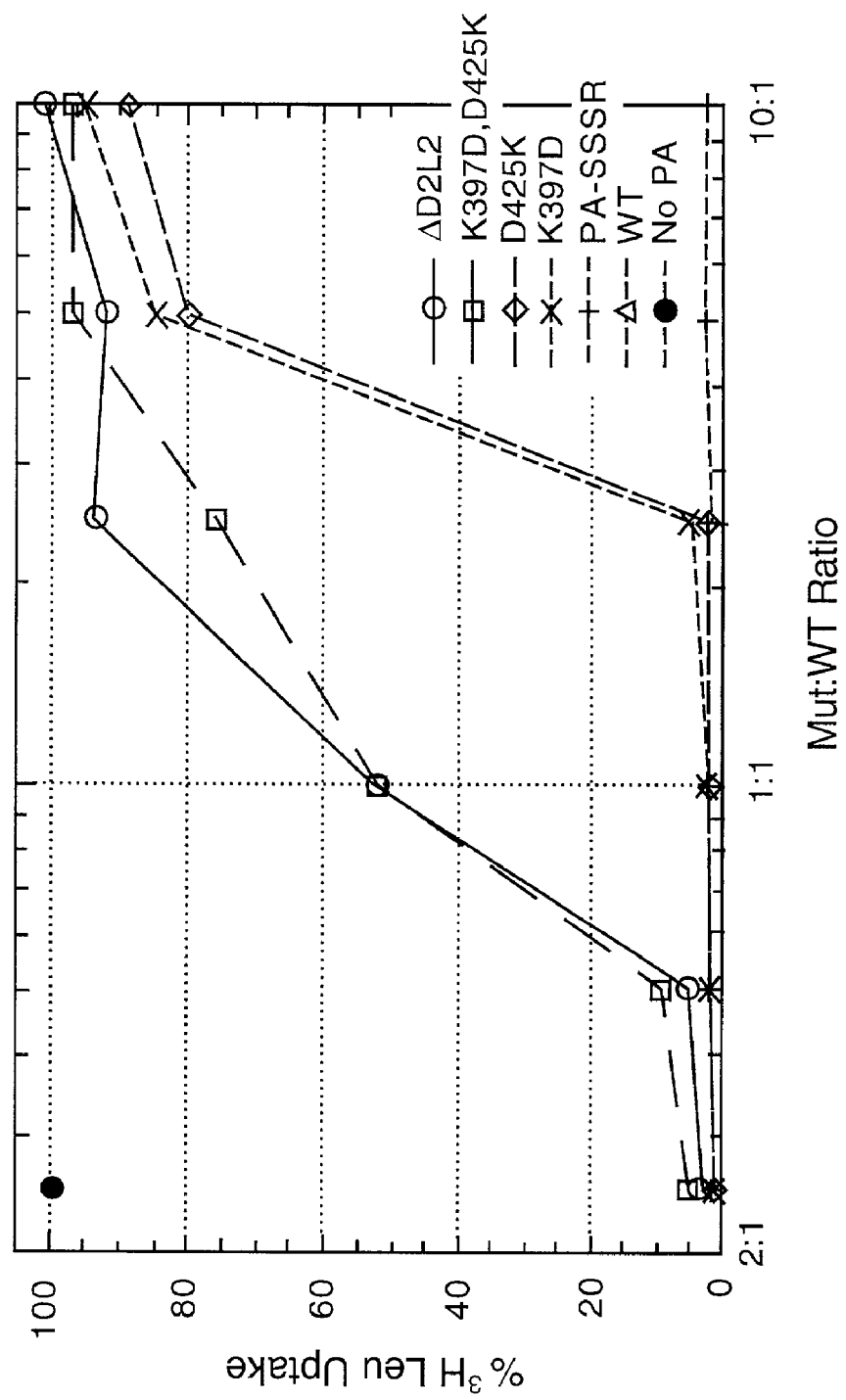
FIG. 8A is a graph showing the decrease in wild-type PA-mediated inhibition of protein synthesis in the LFnDTA toxicity assay. Increasing concentrations of mutant PA proteins relieve the wild-type PA-mediated inhibition of $^3$H-Leu uptake into the TCA insoluble fraction.
Figure 8B:
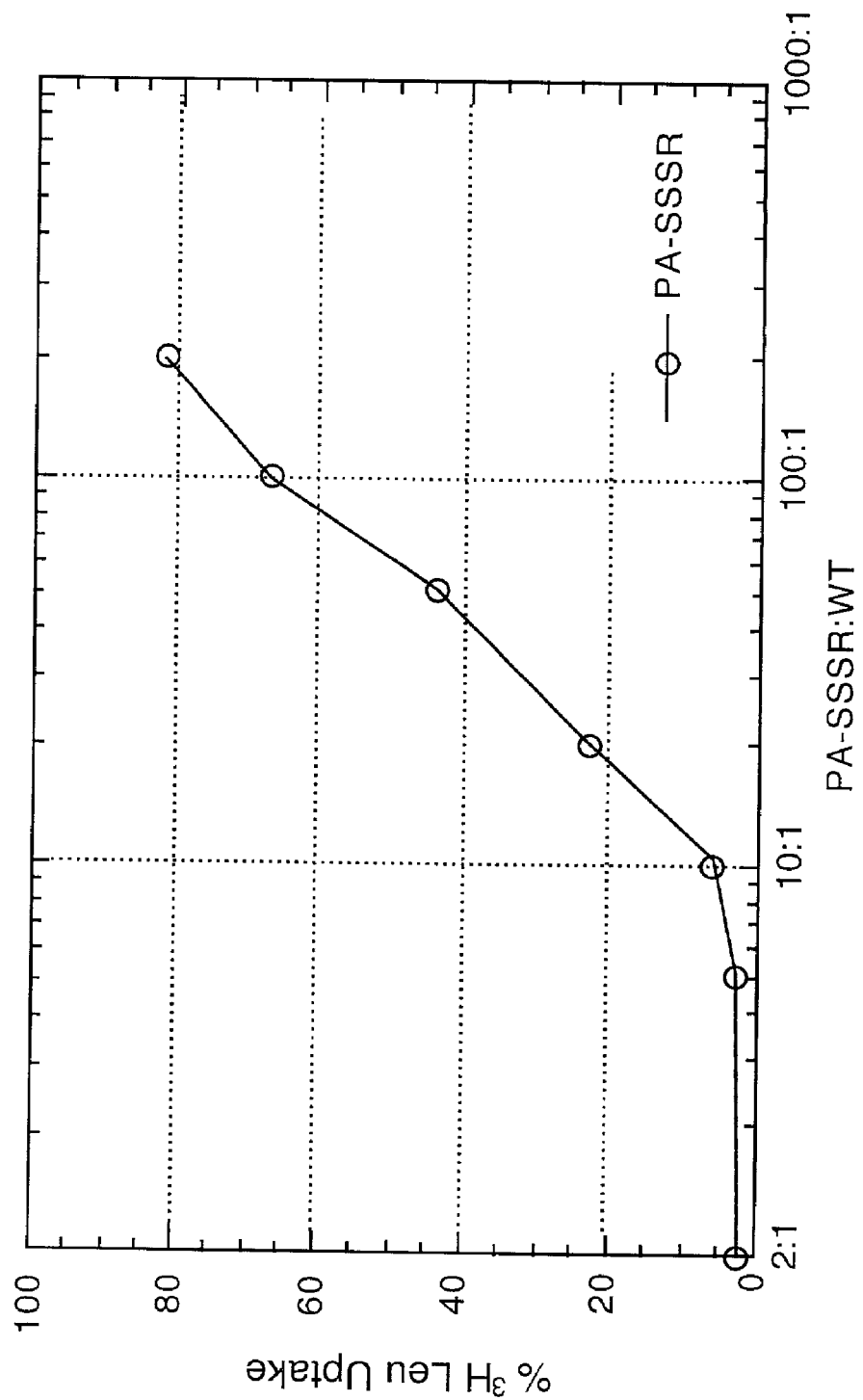
FIG. 8B is a graph showing that much higher amounts of PA-SSR relative to wild-type PA are required to relieve the wild-type PA-mediated inhibition of $^3$H-Leu uptake compared to the amounts required for the mutants listed in FIG. 8A.

A titration of mutant with wild-type PA in the LFnDTA assay was performed to further characterize the inhibition of wild-type PA. Increasing amounts of one of the mutants was added to incubations of cells with wild-type PA and LFnDTA (FIG. 8A). The mutant PA-SSSR, which has the furin recognition site mutated from $^{164}$RKKR$^{167}$ to $^{164}$SSSR$^{167}$, was included as a control. Since this mutant cannot be nicked by furin or other furin-like proteases and thus can not form pores, the mutant can only inhibit PA by competing for the receptor. Both ΔD2L2 and K397D+D425K greatly inhibited PA mediated translocation. Most importantly these mutants do not inhibit solely by competing for the receptor since far less protein is required by these mutants to see 50% inhibition than is required by PA-SSSR (FIG. 7B). The single mutant constituents of K397D+D425K do not inhibit as well as the double mutant but inhibit better than PA-SSSR. Taken together these data suggest that ΔD2L2, K397D+D425K, and K395D+K397D+D425K+D426K PA are dominant negative inhibitors of wild-type PA.

The dominant negative inhibitory activity of the F427A, D425K, K397D+D425K+F427A, F427A+ΔD2L2, K397D+F427A+ΔD2L2 PA mutants was also measured. For this assay, increasing amounts of the mutant forms of PA were mixed with a constant amount of wild-type PA as described above. The most potent member of this group, the K397D+D425K+F427A triple mutant, almost completely blocked toxin action at a 1:1 ratio of mutant:wild-type PA. The D2L2, K397D+D425K, F427A, F427A+ΔD2L2, and K397D+F427A+ΔD2L2 PA mutants also had inhibitory activity. The K397D+D425K+F427A+ΔD2L2, F427D, and F427K PA mutants also exhibited dominant negative activity in the LFnDTA toxicity assay. In contrast, another translocation-deficient mutant, K397D, caused virtually no inhibition at a 1:1 ratio, showing that not all mutants of this type are strongly inhibitory (FIG. 9). The SSSR control mutant caused no detectable inhibition of toxin action, even in 10-fold excess over wild-type PA, implying that competition for receptors did not contribute significantly to the inhibitory activities of the other mutants.

TABLE 2

Predicted and Measured Compositions of PA Oligomers Formed from Various Ratios of Mutant to Wild-type PA

| | Predicted % of the total heptamer population | | | Activity Retained | |
|---|---|---|---|---|---|
| Mutant:Wt (mole:mole) | WT$_7$Mut$_0$ | WT$_6$Mut$_1$ | WT$_5$Mut$_2$ | ΔD2L2 Mix | K397D + D425A Mix |
| 1:1 | 0.78% | 6% | 22% | 0.7% ± .2 | 0.9% ± .06 |
| 0.75:1 | 2 | 10.4 | 23.5% | 3.8% ± 2 | 1.2% ± .2 |
| 0.5:1 | 5.8 | 25.8 | 56.8 | 13.5% ± .5 | 5.8% ± 3.6 |
| 0.25:1 | 21 | 57 | 85 | 14.3% ± 2 | 10% ± 2 |

The predicted values represent the percent of the total heptamers that are expected to have at least the indicated number of wild-type molecules in the mixtures containing varying ratios of mutant and wild-type PA. The WT$_7$Mut$_0$ column represents the percent of the total heptamers that are expected to contain seven wild-type PA molecules. The WT$_6$Mut$_1$ column represents the percent of the total heptamers that are expected to contain at least six wild-type PA molecules(i.e., the heptamers that either contain six wild-type PA molecules and one mutant PA molecule or contain seven wild-type PA molecules and zero mutant PA molecules. Similarly, the WT$_5$Mut$_2$ column represents the percent of the total heptamers that are expected to contain at least five wild-type PA molecules These values were calculated using Pascal's triangle. The values listed under "Activity Retained" are the actual experimental values seen in these mixtures.

The hypothesis that inhibition by the dominant negative mutants depends upon the ability of their PA63 moieties to form hybrid complexes with wild-type PA63 was tested using purified homo- and hetero-heptamers. PA in solution can be cleaved at the furin site by mild trypsinization, and the resulting fragments can be separated by chromatography of the trypsin-nicked molecule on an anion-exchange column (Miller et al, Biochemistry 38, 10432, 1999). Purified PA63 isolated by this method is heptameric, indicating that the oligomerization equilibrium is greatly in favor of this form, and may be structurally similar or identical to the prepore. Purified homo-heptamers were prepared from wild-type PA and each of the K397D+D425K, ΔD2L2, F427A, D425K, and K397D translocation deficient PA mutants. Putative hetero-heptamers were prepared by mixing each mutant PA 1:1 with wild-type PA, followed by trypsinization of the mixture and chromatography of the products on an anion-exchange column.

The LFnDTA-dependent inhibition of protein synthesis by each hetero-heptamer and by an equivalent amount of a 1:1 mixture of the corresponding mutant and wild-type homo-heptamers was measured. Hetero-heptamers containing the K397D+D425K, ΔD2L2, F427A and D425K mutants did not mediate the action of LFnDTA, whereas the corresponding mixtures of homo-heptamers were highly active (FIG. 11). In contrast, the putative hetero-heptamer formed by mixing K397D with wild-type PA was as active as the mixture of homo-K397D PA and homo-wild-type PA. These results are consistent with the properties of these mutants in the experiment of FIG. 9 and support the notion that PA63 from the dominant negative mutants inactivates the wild-type protein by co-oligomerizing with it. The absence of inhibitory activity of K397D in the hetero-heptamer preparation may reflect a defect either in ability to co-oligomerize with the wild-type protein or in ability to inhibit its activity within a heptamer. The finding that mutant homo-heptamers did not inhibit the activity of the wild-type indicates that little competition for receptors and little or no subunit exchange among heptamers occurred under the conditions of the experiment.

As described above, the fact that the K397D+D425K double mutant almost completely blocked activity in these LFnDTA toxicity assays suggests both that a single molecule of the mutant inactivates a heptamer and that oligomerization is stochastic. The ΔD2L2, D425K, and F427A mutants appear to be slightly less inhibitory, implying that more than one molecule of these mutants per heptamer may be required for inactivation and/or that their co-oligomerization with wild-type PA may not be purely stochastic. Other factors, such as the order of addition of B moieties to a growing heptamer complex (e.g., the B moiety that is added first or last) may also effect inactivation. It is not intended that the invention be limited by any proposed mechanism for inhibition set forth in the specification.

EXAMPLE 8

Formation of SDS-resistant Oligomers Containing Mutant and Wild-type PA

To examine the interaction of ΔD2L2 and K397D+D425K mutants with wild-type PA, an equimolar ratio of mutant to wild-type PA was mixed, nicked with trypsin, and analyzed by SDS-PAGE for SDS-resistant oligomer formation. When either mutant was mixed with wild-type PA, a new species of SDS-resistant PA was formed. In contrast to wild-type PA alone which produces a diffuse high molecular weight smear in the gel, the mixture of mutant and wild-type PA results in the formation of a sharp high molecular weight band. This sharp band also differs from what is seen for either of the mutants alone: K397D+D425K alone does not form an SDS-resistant oligomer, and ΔD2L2 PA alone forms an oligomer which migrates farther in the gel than the band formed when wild-type PA is also present. Although the exact composition or nature of this band has not been determined, this band further suggests that the mutants interact with wild-type PA in SDS-resistant oligomers resulting in a change in the mobility of the oligomer in the gel.

EXAMPLE 9

Toxin Inhibition in vivo

The properties displayed by the dominant negative mutants in vitro imply that they should inhibit toxin action in vivo. To test this hypothesis, activities of three of these mutants (K397D+D425K, ΔD2L2, and F427A) were measured in a classical in vivo model for anthrax toxin action, the Fisher 344 rat (Ivins et al., Appl. Environ. Microbiol. 55:2098, 1989). Male rats (250–300 g) injected intravenously with a mixture of 8 μg LF and 40 μg PA (approximately 10 times the minimal lethal dose) become moribund after about 90 minutes (Table 3). When wild-type PA was replaced with any of the dominant negatives mutants, the animals showed no symptoms of intoxication during the two week time period before the animals were sacrificed. When a dominant negative PA was added to the wild-type PA/LF mixture before injection, either at a 1:1 ratio relative to wild-type PA (40 μg dominant negative PA) or at a 0.25:1 ratio (10 μg dominant negative PA), the injected animals also survived without symptoms. The SSSR mutant had little effect on the activity of the toxin. These results are consistent with our in vitro results and demonstrate that the dominant negative mutants can ablate anthrax toxin action in vivo, even at a sub-stoichiometric (0.25:1) ratio to wild-type PA.

TABLE 3

Inhibition of wild-type PA by PA mutants in vivo

| Quantity of protein (μg) | | | | | | |
|---|---|---|---|---|---|---|
| WT | ΔD2L2 | K397D + D425K | F427A | SSR | TTM | |
| 40 | — | — | — | — | 90 ± 11 min | |
| — | 40 | — | — | — | Survived | |
| — | — | 40 | — | — | Survived | |
| — | — | — | 40 | — | Survived | |
| 40 | 40 | — | — | — | Survived | |
| 40 | — | 40 | — | — | Survived | |
| 40 | — | — | 40 | — | Survived | |
| 40 | — | — | — | 40 | 100 ± 3 min | |
| 40 | 10 | — | — | — | Survived | |
| 40 | — | 10 | — | — | Survived | |
| 40 | — | — | 10 | — | Survived | |

The ability of the K397D+D425K+F427A triple mutant ("Triple") to inhibit the activity of wild-type PA in vivo was compared to that of the K397D+D425K double mutant ("Double") (Table 4). This experiment was performed as described above using rats injected with a mixture of 40 μg wild-type PA, 10 μg LF, and either PBS or a dominant negative PA mutant.

TABLE 4

Inhibition of wild-type PA by PA mutants in vivo

| | Animals | amount of mutant PA | TTM |
|---|---|---|---|
| PBS | 2 | — | ~100 minutes |
| Double | 2 | 40 μg | Survived |
| Triple | 2 | 40 μg | Survived |
| Double | 4 | 4 μg | Survived |
| Triple | 4 | 4 μg | Survived |

The anti-PA and the neutralizing antibody titer generated by vaccination of rats with K397D+D425K, ΔD2L2, or F427A PA was also measured. For this determination, groups of six animals were vaccinated three times each at 0, 3, and 6 weeks with 50 µg of protein in 200 µl of Ribi Tri-Mix adjuvant (Sigma) by intramuscular injection into the hind-quarters. Two days prior to the first injection and 14 days following each injection, blood was drawn from each animal and the serum was collected. Sixteen days following the final injection the rats were challenged with a lethal dose of LF (30 µg PA+6 µg LF) by IV injection as described in Table 5. The mean anti-PA antibody titers in the serum were determined in a standard ELISA assay against PA. The titers are reported as the reciprocal of the geometric mean of the dilution at which the reactivity of the serum ends. Neutralizing antibodies were titered in an LFnDTA assay at $1 \times 10^{-10}$ M PA and $1 \times 10^{-10}$ M LFnDTA. Antibody dilutions were incubated with PA at 37° C. for one hour prior to starting the assay. Protein synthesis inhibition was measured using the LFnDTA toxicity assay as described above. The neutralizing titers are represented as the reciprocal of the geometric mean dilution required to inhibit PA activity by 50%. As illustrated in Table 5, the K397D+D425K, ΔD2L2, and F427A PA mutants exhibited little or no diminution in immunogenicity relative to wild-type PA in Fisher rats. The neutralizing and anti-PA antibody titers, after three injections were similar, regardless of immunogen employed, and all vaccinated animals survived challenge with a lethal dose of wild-type PA plus LF administered 16 days after the last injection.

TABLE 5

Anti-PA and the neutralizing antibody titer generated by vaccination of rats with PA mutants

|  | Animals | Anti-PA Titer | Neutralizing Titer | TTM |
| --- | --- | --- | --- | --- |
| PBS | 6 | <10 | <10 | 74.2 ± 1.5 |
| WT | 5 | 43,300 | 2,490 | Survived |
| ΔD2L2 | 6 | 47,500 | 3,350 | Survived |
| K397D + D425K | 6 | 65,500 | 2,260 | Survived |
| F427A | 6 | 132,000 | 6,090 | Survived |

EXAMPLE b 10

Antibodies to PA

Antibodies to a PA protein may be used as therapeutics and/or diagnostics. Antibodies may be produced using standard methods by immunologically challenging a B-cell-containing biological system, e.g., an animal such as a mouse or rabbit, with a PA protein or a fragment thereof to stimulate production of an anti-PA antibody by the B-cells, followed by isolation of the antibody from the biological system. For the generation of monoclonal antibodies, the spleen may be harvested from the animal with the highest ELISA-determined immune response to the PA protein, and the B-cells fused to NS-1 myeloma cells to generate hybridomas. Hybridomas that secrete antibodies which bind PA may be selected using a standard ELISA assay or by western blotting. Monoclonal cell lines producing a high antibody titer and specifically recognizing a PA protein are saved.

The cell lines may also be screened to identify lines that produce antibodies which bind naturally-occuring PA with greater affinity than a mutant PA protein. These antibodies may be generated by administering to animals fragments of naturally-occurring PA that contain residues such as K397, D425, D426, or F427. The resulting antibodies may then be screened to determine which antibodies bind naturally-occurring PA but do not bind a mutant PA protein in which one or more of residues K397, D425, D426, or F427 is mutated or deleted. For example, the antibodies may be applied to a column containing an immobilized mutant PA protein, and the antibodies that do not bind the mutant PA protein may be selected. Antibodies may also be generated that are reactive with residues in the D2L2 loop; these antibodies may be produced by administering a fragment of PA containing the D2L2 loop to an animal, as described above. Antibodies that are reactive with residues in the D2L2 loop of naturally-occurring PA may also be screened to select the antibodies that do not bind a mutant PA protein in which one or more residues in the D2L2 loop are deleted. Alternatively, antibodies may be generated that bind a mutant PA with greater affinity than a naturally-occurring PA molecule by administering a fragment of a mutant PA to an animal as described above and selecting the antibodies with greater affinity for the mutant PA form. These antibodies may bind a residue in a mutant PA that is not present in a naturally-occurring PA.

Anti-PA antibodies may be used to measure PA protein in a biological sample such as serum, by contacting the sample with the antibody and then measuring immune complexes as a measure of the PA protein in the sample. Thus, these antibodies may be used in kits to determine whether a subject has been exposed to anthrax toxin.

Antibodies to PA can also be used as therapeutics for the treatment or prevention of anthrax infection. If a anti-PA antibody that binds wild-type PA but does not bind a dominant negative PA mutant is administered to a subject for passive immunization against anthrax infection, a dominant negative PA mutant may also be administered to the same subject as a therapeutic to inhibit the activity of wild-type PA. Because the administered anti-PA antibody does not react with the therapeutic dominant negative PA mutant, the anti-PA antibody should not reduce the ability of the dominant negative PA mutant to inhibit wild-type PA. Additionally, an anti-PA antibody that does not react with a therapeutic dominant negative PA mutant may be used to determine the amount of wild-type PA present in a sample from a subject who has been treated with the dominant negative PA mutant.

Similar antibodies may be generated for other mutant B moieties of the present invention.

EXAMPLE 11

Administration of PA Proteins and Fragments

It is not intended that the administration of the PA proteins or fragments of the invention be limited to a particular mode of administration, dosage, or frequency of dosing; the present mode contemplates all modes of administration, including oral, intramuscular, intravenous, subcutaneous, by inhalation, or any other route sufficient to provide a dose adequate to prevent or treat an anthrax infection. One or more of the mutant PA proteins or fragments may be administered to a mammal in a single dose or multiple doses. When multiple doses are administered, the doses can be separated from one another by, for example, one week to one month. It is to be understood that for any particular subject, specific dosage regimes should be adjusted over time according to the individual need and the professional judgement of the person administering or supervising the administration of the compositions.

The pharmaceutical compositions containing one or more PA proteins or fragments of the invention can be prepared as described previously in Remington's Pharmaceutical Sciences by E. W. Martin. Pharmaceutical stabilizing compounds, delivery vehicles, carrier vehicles, or adjuvants may be used. For example, human serum albumin or other human or animal proteins can be used. Phospholipid vesicles or liposomal suspensions are possible pharmaceutically acceptable carriers or delivery vehicles. Adjuvants that can be used in the invention include aluminum compounds, such as aluminum hydroxide, aluminum phosphate, and aluminum hydroxy phosphate. These compositions can be prepared according to methods known to those skilled in the art.

Other mutant B moieties or fragments of the invention may be administered similarly.

EXAMPLE 12

Other Pore-forming Mutants

Figure 15:
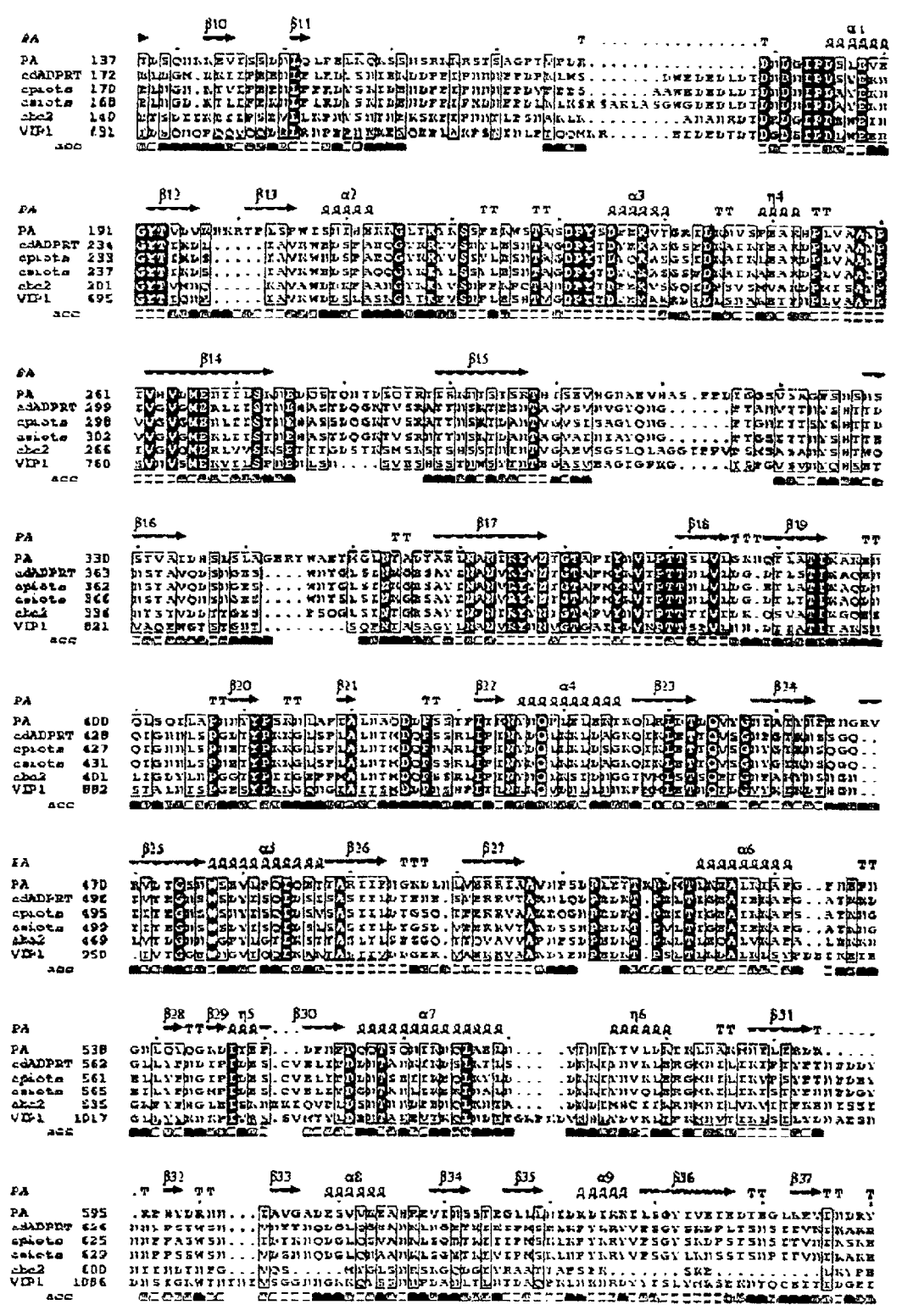
Figure 15:
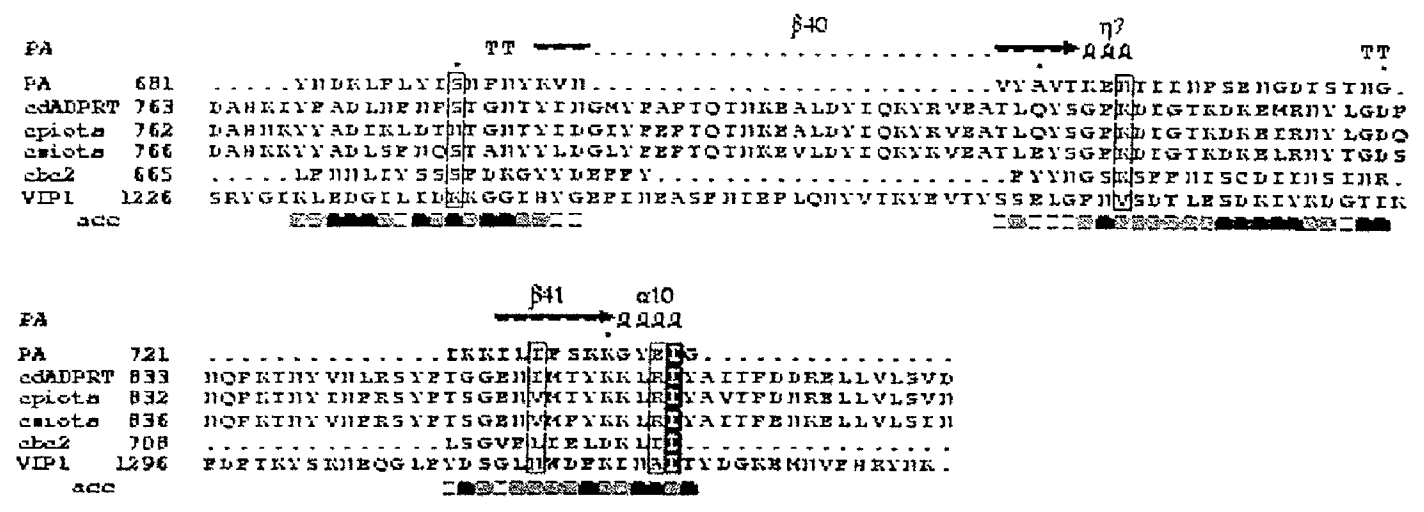
Figure 16:
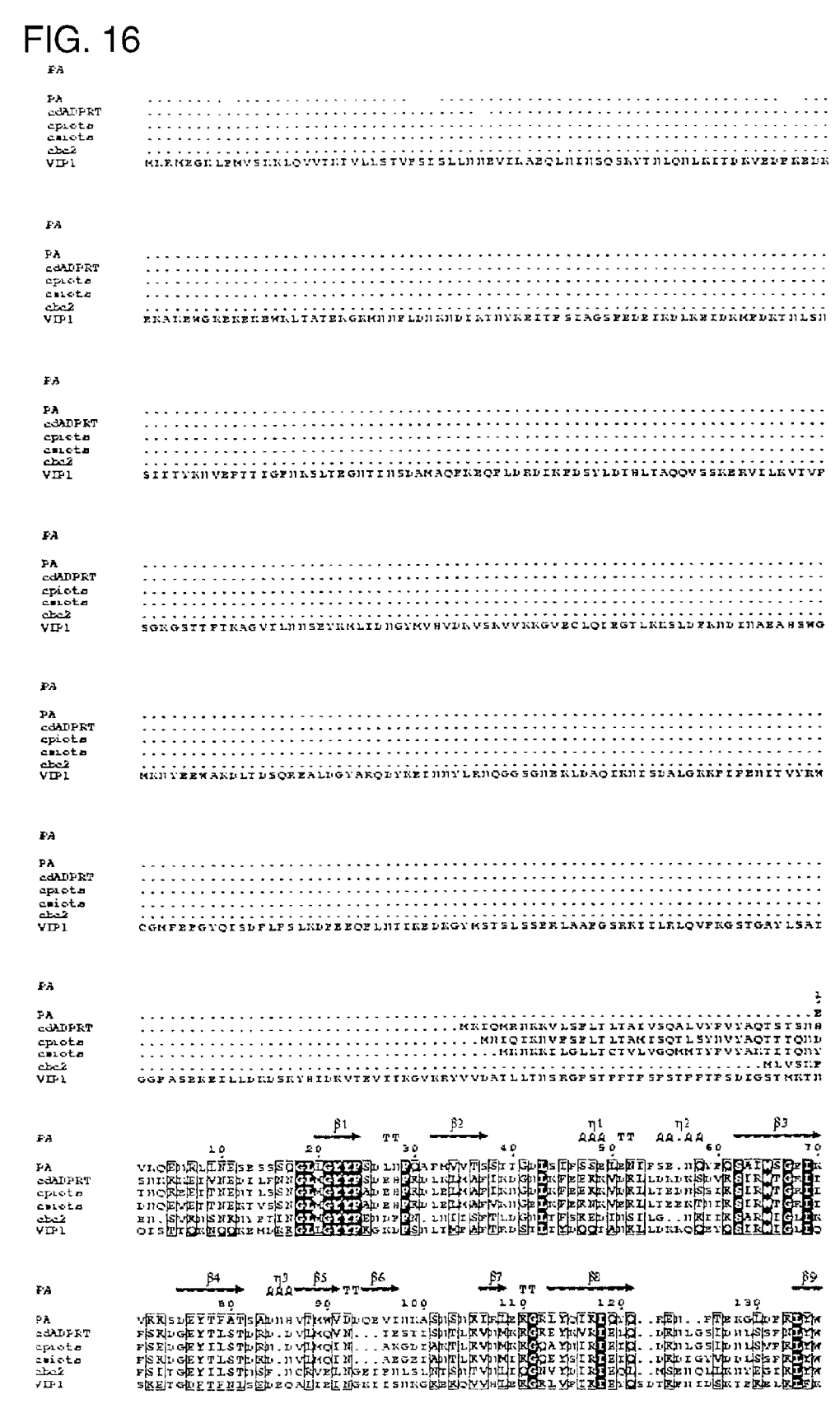
Figure 16:
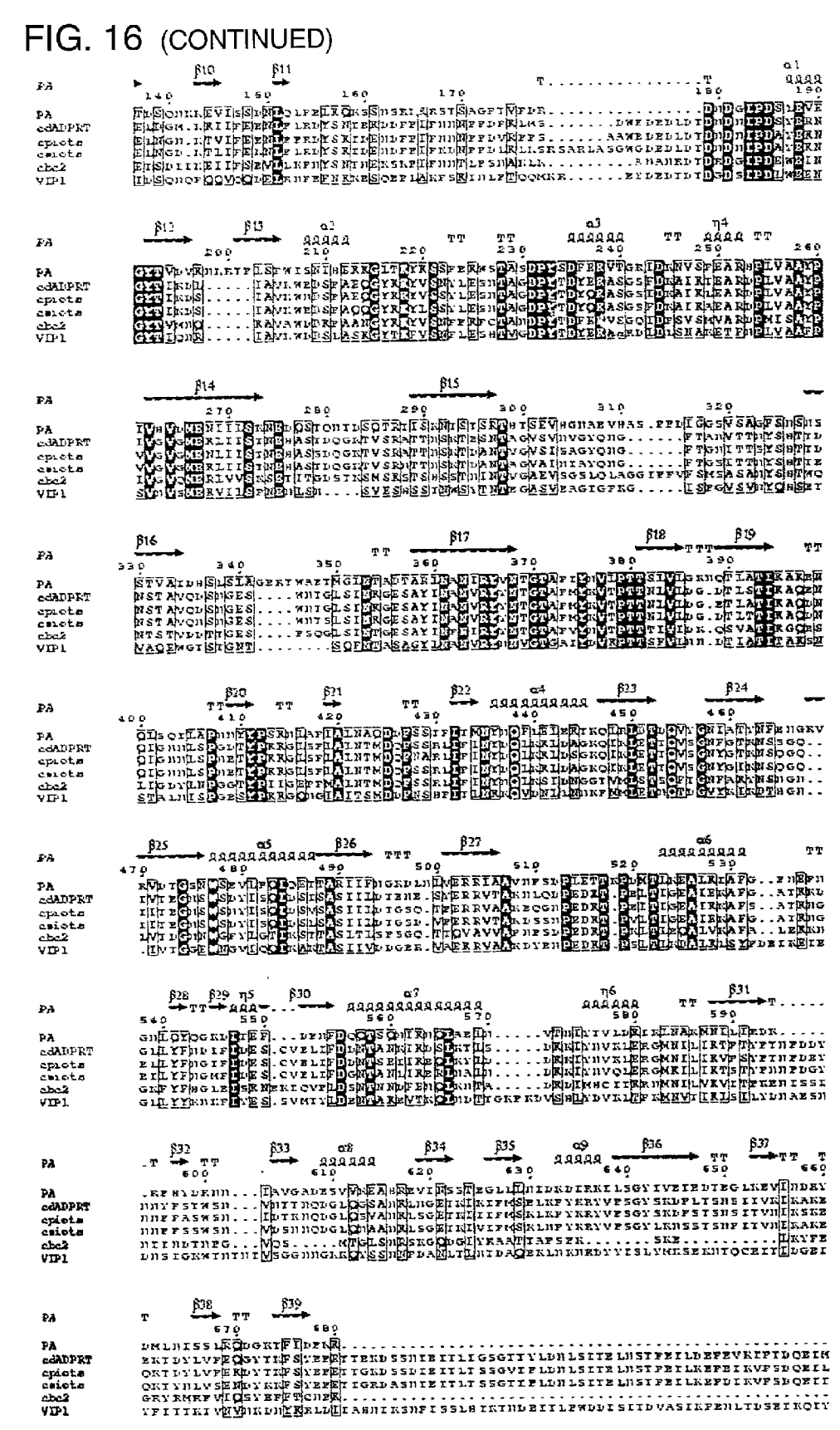
Figure 16:
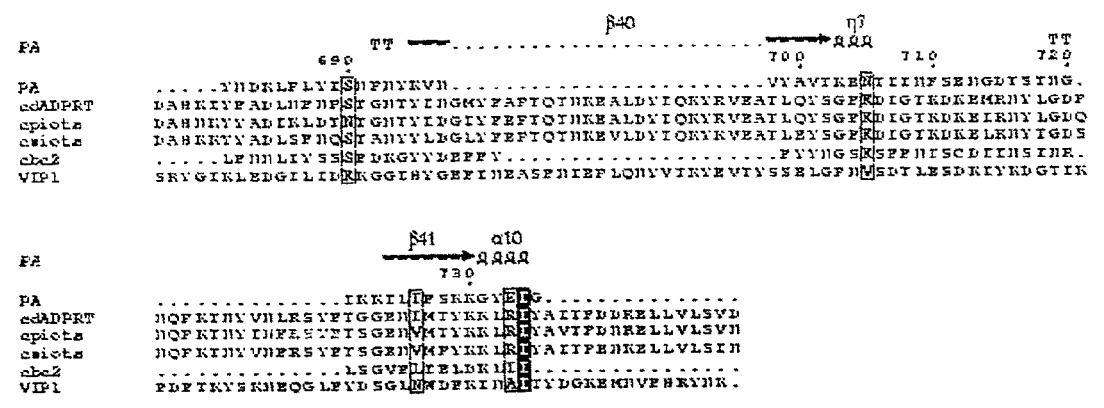

The crystal structure of PA identified four domains of PA (Petosa et al., Nature 385(6619): 833–838, 1997). Domain 2 (residues 259–487) contains a large flexible loop that may undergo a major conformational change during conversion from the prepore to the pore. Mutation, deletion, or insertion of one or more amino acids in this region may result in inhibition of the pore-forming ability of the protein in vivo and/or result in the ability of the PA mutant to inhibit the pore-forming ability of naturally-occurring PA. For example, residues in domain 2 of PA that are identical to the corresponding residues in one or more other pore-forming toxins (such as toxins from *Clostridium difficile, C. Perfringens, C. Spiroforme, C. botulinum, Bacillus cereus*, or *B. thuringiensis*; FIGS. 15 and 16) may be mutated. These residues may be mutated or deleted in PA to generate dominant negative PA mutants. The following residues of domain 2 in PA are invariant among the binary A-B toxins listed in FIGS. 15 and 16: A259, P260, V262, V264, M266, E267, S272 E275 T298, N353, N361, N363 R365, Y366, N368, G370, T371, Y375, V377, P389, T380, T381, V384, T393, I394, P407, Y411, P412, A420, D425, F427, I432, N435, Q438, L450, T452, Q454, G457, G474, W477, and I484. These residues may be mutated to any other amino acid. For example, the residues may be changed to an amino acid with a smaller side chain such as glycine or alanine, or the residues may be changed to an amino acid with a larger or branched side chain such as tryptophan, leucine, or methionine. Additionally, charged residues may be changed to residues with a neutral side chain or residues with a side chain of the opposite charge. Other examples of residues that may be used to replace a naturally-occurring residue are listed in Table 1.

In addition to anthrax toxin, the present invention is relevant to other pore-forming toxins. These toxins may also be mutated to generate toxins with reduced or negligible ability to oligomerize, to form transmembrane channels, or to translocate a ligand. Additionally, dominant negative mutants of other pore-forming mutants may be generated. For example, mutations that correspond to the PA mutations described herein may be made in other toxins that are homologous to PA (such as toxins from *Clostridium difficile, C. Perfringens, C. Spiroforme, C. botulinum, Bacillus cereus*, or *B. thuringiensis*) (FIGS. 15 and 16 and Table 6). Residues in other toxins that correspond to residues in domain 2 of PA may be mutated as described above. Additionally, at least 1, 3, 5, 8, 10, 15, 20, or 24 of the amino acids in the region that corresponds to the D2L2 loop of PA may be deleted in other pore-forming toxins. Also, one or more point mutations may be made at residues that correspond to the mutated PA residues described herein.

Any of these mutant forms of pore-forming toxins may be administered to a mammal for the treatment or prevention of infection by the pathogens (e.g., bacteria) that produce the corresponding toxin.

TABLE 6

Mutations in other pore-forming toxins that correspond to the mutations in anthrax PA which are described herein.
The residues in the other pore-forming toxins that correspond to the residues that were mutated in PA may also be mutated to any other amino acid.

| anthrax PA | C. difficile toxin | C. perfringens toxin | C. spiroforme toxin | C. botulinum toxin | B. cereus toxin |
|---|---|---|---|---|---|
| K397A | Q425A | Q424A | Q428A | Q398A | K879A |
| K397D | Q425D | Q424D | Q428D | Q398D | K879D |
| K397C | Q425C | Q424C | Q428C | Q398C | K879C |
| K397Q | Q425Q | Q424Q | Q428Q | Q398Q | K879Q |
| D425A | D453A | D452A | D456A | D426A | D907A |
| D425N | D453N | D452N | D456N | D426N | D907N |
| D425E | D453E | D452E | D456E | D426E | D907E |
| D425K | D453K | D452K | D456K | D426K | D907K |
| F427A | F455A | F454A | F458A | F428A | F909A |
| K397D + | Q425D + | Q424D + | Q428D + | Q398D + | K879D + |
| D425K | D453K | D452K | D456K | D426K | D907K |
| K395D + | K423D + | K422D + | K426D + | K396D + | T877D |
| K397D + | Q425D + | Q424D + | Q428D + | Q398D + | K879D + |
| D425K + | D453K + | D452K + | D456K + | D426K + | D907K + |
| D426K | Q454K | Q453K | Q457K | Q427K | D908K |
| ΔD2L2 | Δ340–358 | Δ339–357 | Δ343–361 | Δ307–331 | Δ797–816 |
| K397D + | Q425D + | Q424D + | Q428D + | Q398D + | K879D + |
| D425K + | D453K + | D452K + | D456K + | D426K + | D907K + |
| F427A | F455A | F454A | F458A | F428A | F909A |
| F427A + | F455A + | F454A + | F458A + | F428A + | F909A + |
| ΔD2L2 | Δ340–358 | Δ339–357 | Δ343–361 | Δ307–331 | Δ797–816 |
| K397D + | Q425D + | Q424D + | Q428D + | Q398D + | K879D + |
| F427A + | F455A + | F454A + | F458A + | F428A + | F909A+ |
| ΔD2L2 | Δ340–358 | Δ339–357 | Δ343–361 | Δ307–331 | Δ797–816 |
| K397D + | Q425D + | Q424D + | Q428D + | Q398D + | K879D + |
| D425K + | D453K + | D452K + | D456K + | D426K + | D907K + |
| F427A + | F455A + | F454A + | F458A + | F428A + | F909A + |
| ΔD2L2 | Δ340–358 | Δ339–357 | Δ343–361 | Δ307–331 | Δ797–816 |
| F427D | F455D | F454D | F458D | F428D | F909D |
| F427K | F455K | F454K | F458K | F428K | F909K |

Alternatively, random mutagenesis may be performed on nucleic acids encoding pore-forming mutants (such as cholesterol dependent cytolysins or hexameric or heptameric toxins related to the Staphylococcal α-toxin) using standard molecular biology methods. The encoded mutant toxins may be expressed and optionally purified using standard methods. The rubidium release assay described herein may be used to identify mutant toxins with a reduced ability to form a trans membrane channel. Additionally, animal models may be used to identify dominant negative toxin mutants that reduce the toxicity of the corresponding wild-type toxin when both the mutant and wild-type toxins are administered to the animal.

OTHER EMBODIMENTS

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

Other embodiments are within the claims.

---

The invention claimed is:

1. An immunogenic composition comprising a purified anthrax toxin B moiety in a pharmaceutically acceptable carrier, wherein said B moiety comprises SEQ ID NO: 8.

2. A purified anthrax toxin B moiety, wherein said B moiety comprises SEQ ID NO:8.

3. A purified anthrax toxin B moiety, wherein said B moiety comprises SEQ ID NO: 10.

4. A purified anthrax toxin B moiety, wherein said B moiety comprises SEQ ID NO: 11.

5. A purified anthrax toxin B moiety, wherein said B moiety comprises SEQ ID NO: 13.

6. A purified anthrax toxin B moiety, wherein said B moiety comprises SEQ ID NO:16.

7. An immunogenic composition comprising a purified anthrax toxin B moiety in a pharmaceutically acceptable carrier, wherein said B moiety comprises SEQ ID NO:10.

8. An immunogenic composition comprising a purified anthrax toxin B moiety in a pharmaceutically acceptable carrier, wherein said B moiety comprises SEQ ID NO: 11.

9. An immunogenic composition comprising a purified anthrax toxin B moiety in a pharmaceutically acceptable carrier, wherein said B moiety comprises SEQ ID NO:13.

10. An immunogenic composition comprising a purified anthrax toxin B moiety in a pharmaceutically acceptable carrier, wherein said B moiety comprises SEQ ID NO:16.

* * * * *

SEQUENCE LISTING

<160> NUMBER OF SEQ ID NOS: 35

<210> SEQ ID NO 1
<211> LENGTH: 735
<212> TYPE: PRT
<213> ORGANISM: Bacillus anthracis

<400> SEQUENCE: 1

```
Glu Val Lys Gln Glu Asn Arg Leu Leu Asn Glu Ser Glu Ser Ser Ser
 1               5                  10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Glu Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
```

```
                     325                 330                 335
Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
    370                 375                 380

Leu Gly Lys Asn Gln Thr Leu Ala Thr Ile Lys Ala Ala Glu Asn Gln
385                 390                 395                 400

Leu Ser Gln Ile Leu Ala Pro Asn Asn Tyr Tyr Pro Ser Lys Asn Leu
            405                 410                 415

Ala Pro Ile Ala Leu Asn Ala Gln Asp Asp Phe Ser Ser Thr Pro Ile
        420                 425                 430

Thr Met Asn Tyr Asn Gln Phe Leu Glu Leu Glu Lys Thr Lys Gln Leu
    435                 440                 445

Arg Leu Asp Thr Asp Gln Val Tyr Gly Asn Ile Ala Thr Tyr Asn Phe
450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
            485                 490                 495

Asp Leu Asn Leu Val Glu Arg Arg Ile Ala Ala Val Asn Pro Ser Asp
        500                 505                 510

Pro Leu Glu Thr Thr Lys Pro Asp Met Thr Leu Lys Glu Ala Leu Lys
    515                 520                 525

Ile Ala Phe Gly Phe Asn Glu Pro Asn Gly Asn Leu Gln Tyr Gln Gly
530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
            565                 570                 575

Val Leu Asp Lys Ile Lys Leu Asn Ala Lys Met Asn Ile Leu Ile Arg
        580                 585                 590

Asp Lys Arg Phe His Tyr Asp Arg Asn Asn Ile Ala Val Gly Ala Asp
    595                 600                 605

Glu Ser Val Val Lys Glu Ala His Arg Glu Val Ile Asn Ser Ser Thr
610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
            645                 650                 655

Asn Asp Arg Tyr Asp Met Leu Asn Ile Ser Ser Leu Arg Gln Asp Gly
        660                 665                 670

Lys Thr Phe Ile Asp Phe Lys Lys Tyr Asn Asp Lys Leu Pro Leu Tyr
    675                 680                 685

Ile Ser Asn Pro Asn Tyr Lys Val Asn Val Tyr Ala Val Thr Lys Glu
690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
            725                 730                 735

<210> SEQ ID NO 2
```

<211> LENGTH: 735
<212> TYPE: PRT
<213> ORGANISM: Bacillus anthracis

<400> SEQUENCE: 2

```
Glu Val Lys Gln Glu Asn Arg Leu Leu Asn Glu Ser Glu Ser Ser
 1               5                  10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
                35                  40                  45

Glu Leu Glu Asn Ile Pro Ser Glu Asn Gln Tyr Phe Gln Ser Ala Ile
     50                  55                  60

Trp Ser Gly Phe Ile Lys Val Lys Lys Ser Asp Glu Tyr Thr Phe Ala
 65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Glu Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
    370                 375                 380

Leu Gly Lys Asn Gln Thr Leu Ala Thr Ile Lys Ala Asp Glu Asn Gln
```

```
                385                 390                 395                 400
        Leu Ser Gln Ile Leu Ala Pro Asn Asn Tyr Tyr Pro Ser Lys Asn Leu
                            405                 410                 415

Ala Pro Ile Ala Leu Asn Ala Gln Asp Asp Phe Ser Ser Thr Pro Ile
                    420                 425                 430

Thr Met Asn Tyr Asn Gln Phe Leu Glu Leu Glu Lys Thr Lys Gln Leu
                    435                 440                 445

Arg Leu Asp Thr Asp Gln Val Tyr Gly Asn Ile Ala Thr Tyr Asn Phe
                    450                 455                 460

Glu Asn Gly Arg Val Arg Val Asp Thr Gly Ser Asn Trp Ser Glu Val
        465                 470                 475                 480

Leu Pro Gln Ile Gln Glu Thr Thr Ala Arg Ile Ile Phe Asn Gly Lys
                        485                 490                 495

Asp Leu Asn Leu Val Glu Arg Arg Ile Ala Ala Val Asn Pro Ser Asp
                    500                 505                 510

Pro Leu Glu Thr Thr Lys Pro Asp Met Thr Leu Lys Glu Ala Leu Lys
                    515                 520                 525

Ile Ala Phe Gly Phe Asn Glu Pro Asn Gly Asn Leu Gln Tyr Gln Gly
        530                 535                 540

Lys Asp Ile Thr Glu Phe Asp Phe Asn Phe Asp Gln Gln Thr Ser Gln
        545                 550                 555                 560

Asn Ile Lys Asn Gln Leu Ala Glu Leu Asn Ala Thr Asn Ile Tyr Thr
                        565                 570                 575

Val Leu Asp Lys Ile Lys Leu Asn Ala Lys Met Asn Ile Leu Ile Arg
                    580                 585                 590

Asp Lys Arg Phe His Tyr Asp Arg Asn Asn Ile Ala Val Gly Ala Asp
                    595                 600                 605

Glu Ser Val Val Lys Glu Ala His Arg Glu Val Ile Asn Ser Ser Thr
                    610                 615                 620

Glu Gly Leu Leu Leu Asn Ile Asp Lys Asp Ile Arg Lys Ile Leu Ser
        625                 630                 635                 640

Gly Tyr Ile Val Glu Ile Glu Asp Thr Glu Gly Leu Lys Glu Val Ile
                        645                 650                 655

Asn Asp Arg Tyr Asp Met Leu Asn Ile Ser Ser Leu Arg Gln Asp Gly
                    660                 665                 670

Lys Thr Phe Ile Asp Phe Lys Lys Tyr Asn Asp Lys Leu Pro Leu Tyr
                    675                 680                 685

Ile Ser Asn Pro Asn Tyr Lys Val Asn Val Tyr Ala Val Thr Lys Glu
                    690                 695                 700

Asn Thr Ile Ile Asn Pro Ser Glu Asn Gly Asp Thr Ser Thr Asn Gly
        705                 710                 715                 720

Ile Lys Lys Ile Leu Ile Phe Ser Lys Lys Gly Tyr Glu Ile Gly
                        725                 730                 735

<210> SEQ ID NO 3
<211> LENGTH: 735
<212> TYPE: PRT
<213> ORGANISM: Bacillus anthracis

<400> SEQUENCE: 3

Glu Val Lys Gln Glu Asn Arg Leu Leu Asn Glu Ser Glu Ser Ser Ser
        1               5                   10                  15

Gln Gly Leu Leu Gly Tyr Tyr Phe Ser Asp Leu Asn Phe Gln Ala Pro
                    20                  25                  30
```

-continued

```
Met Val Val Thr Ser Ser Thr Thr Gly Asp Leu Ser Ile Pro Ser Ser
            35                  40                  45
Glu Leu Glu Asn Ile Pro Ser Glu Asn Gln Tyr Phe Gln Ser Ala Ile
 50                  55                  60
Trp Ser Gly Phe Ile Lys Val Lys Lys Ser Asp Glu Tyr Thr Phe Ala
 65                  70                  75                  80
Thr Ser Ala Asp Asn His Val Thr Met Trp Val Asp Asp Gln Glu Val
                 85                  90                  95
Ile Asn Lys Ala Ser Asn Ser Asn Lys Ile Arg Leu Glu Lys Gly Arg
                100                 105                 110
Leu Tyr Gln Ile Lys Ile Gln Tyr Gln Arg Glu Asn Pro Thr Glu Lys
                115                 120                 125
Gly Leu Asp Phe Lys Leu Tyr Trp Thr Asp Ser Gln Asn Lys Lys Glu
                130                 135                 140
Val Ile Ser Ser Asp Asn Leu Gln Leu Pro Glu Leu Lys Gln Lys Ser
145                 150                 155                 160
Ser Asn Ser Arg Lys Lys Arg Ser Thr Ser Ala Gly Pro Thr Val Pro
                165                 170                 175
Asp Arg Asp Asn Asp Gly Ile Pro Asp Ser Leu Glu Val Glu Gly Tyr
                180                 185                 190
Thr Val Asp Val Lys Asn Lys Arg Thr Phe Leu Ser Pro Trp Ile Ser
                195                 200                 205
Asn Ile His Glu Lys Lys Gly Leu Thr Lys Tyr Lys Ser Ser Pro Glu
                210                 215                 220
Lys Trp Ser Thr Ala Ser Asp Pro Tyr Ser Asp Phe Glu Lys Val Thr
225                 230                 235                 240
Gly Arg Ile Asp Lys Asn Val Ser Pro Glu Ala Arg His Pro Leu Val
                245                 250                 255
Ala Ala Tyr Pro Ile Val His Val Asp Met Glu Asn Ile Ile Leu Ser
                260                 265                 270
Lys Asn Glu Asp Gln Ser Thr Gln Asn Thr Asp Ser Glu Thr Arg Thr
                275                 280                 285
Ile Ser Lys Asn Thr Ser Thr Ser Arg Thr His Thr Ser Glu Val His
                290                 295                 300
Gly Asn Ala Glu Val His Ala Ser Phe Phe Asp Ile Gly Gly Ser Val
305                 310                 315                 320
Ser Ala Gly Phe Ser Asn Ser Asn Ser Ser Thr Val Ala Ile Asp His
                325                 330                 335
Ser Leu Ser Leu Ala Gly Glu Arg Thr Trp Ala Glu Thr Met Gly Leu
                340                 345                 350
Asn Thr Ala Asp Thr Ala Arg Leu Asn Ala Asn Ile Arg Tyr Val Asn
                355                 360                 365
Thr Gly Thr Ala Pro Ile Tyr Asn Val Leu Pro Thr Thr Ser Leu Val
                370                 375                 380
Leu Gly Lys Asn Gln Thr Leu Ala Thr Ile Lys Ala Cys Glu Asn Gln
385                 390                 395                 400
Leu Ser Gln Ile Leu Ala Pro Asn Asn Tyr Tyr Pro Ser Lys Asn Leu
                405                 410                 415
Ala Pro Ile Ala Leu Asn Ala Gln Asp Asp Phe Ser Ser Thr Pro Ile
                420                 425                 430
Thr Met Asn Tyr Asn Gln Phe Leu Glu Leu Glu Lys Thr Lys Gln Leu
                435                 440                 445
Arg Leu Asp Thr Asp Gln Val Tyr Gly Asn Ile Ala Thr Tyr Asn Phe
```

```
            450                 455                 460
Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735

<210> SEQ ID NO 4
<211> LENGTH: 735
<212> TYPE: PRT
<213> ORGANISM: Bacillus anthracis

<400> SEQUENCE: 4

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Glu Tyr Thr Phe Ala
65                  70                  75                  80

Thr Ser Ala Asp Asn His Val Thr Met Trp Val Asp Asp Gln Glu Val
                85                  90                  95
```

-continued

```
Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Glu Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
    370                 375                 380

Leu Gly Lys Asn Gln Thr Leu Ala Thr Ile Lys Ala Gln Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Phe Ser Ser Thr Pro Ile
            420                 425                 430

Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
    450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
```

515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735

<210> SEQ ID NO 5
<211> LENGTH: 735
<212> TYPE: PRT
<213> ORGANISM: Bacillus anthracis

<400> SEQUENCE: 5

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

-continued

```
Ser Asn Ser Arg Lys Lys Arg Ser Thr Ser Ala Gly Pro Thr Val Pro
            165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
            195                 200                 205

Asn Ile His Glu Lys Lys Gly Leu Thr Lys Tyr Lys Ser Ser Pro Glu
            210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
            245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Glu Thr Arg Thr
            275                 280                 285

Ile Ser Lys Asn Thr Ser Thr Ser Arg Thr His Thr Ser Glu Val His
            290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
            325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
            355                 360                 365

Thr Gly Thr Ala Pro Ile Tyr Asn Val Leu Pro Thr Thr Ser Leu Val
            370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
            405                 410                 415

Ala Pro Ile Ala Leu Asn Ala Gln Ala Asp Phe Ser Ser Thr Pro Ile
            420                 425                 430

Thr Met Asn Tyr Asn Gln Phe Leu Glu Leu Glu Lys Thr Lys Gln Leu
            435                 440                 445

Arg Leu Asp Thr Asp Gln Val Tyr Gly Asn Ile Ala Thr Tyr Asn Phe
450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
            485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
            515                 520                 525

Ile Ala Phe Gly Phe Asn Glu Pro Asn Gly Asn Leu Gln Tyr Gln Gly
            530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
            565                 570                 575

Val Leu Asp Lys Ile Lys Leu Asn Ala Lys Met Asn Ile Leu Ile Arg
```

```
                580                 585                 590
Asp Lys Arg Phe His Tyr Asp Arg Asn Asn Ile Ala Val Gly Ala Asp
            595                 600                 605

Glu Ser Val Val Lys Glu Ala His Arg Glu Val Ile Asn Ser Ser Thr
        610                 615                 620

Glu Gly Leu Leu Asn Ile Asp Lys Asp Ile Arg Lys Ile Leu Ser
625                 630                 635                 640

Gly Tyr Ile Val Glu Ile Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735

<210> SEQ ID NO 6
<211> LENGTH: 735
<212> TYPE: PRT
<213> ORGANISM: Bacillus anthracis

<400> SEQUENCE: 6

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220
```

-continued

```
Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
            245                 250                 255

Ala Ala Tyr Pro Ile Val His Val Asp Met Glu Asn Ile Ile Leu Ser
                260                 265                 270

Lys Asn Glu Asp Gln Ser Thr Gln Asn Thr Asp Ser Glu Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
        340                 345                 350

Asn Thr Ala Asp Thr Ala Arg Leu Asn Ala Asn Ile Arg Tyr Val Asn
    355                 360                 365

Thr Gly Thr Ala Pro Ile Tyr Asn Val Leu Pro Thr Thr Ser Leu Val
370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asn Asp Phe Ser Ser Thr Pro Ile
                420                 425                 430

Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
```

-continued

```
                645                 650                 655
Asn Asp Arg Tyr Asp Met Leu Asn Ile Ser Ser Leu Arg Gln Asp Gly
            660                 665                 670
Lys Thr Phe Ile Asp Phe Lys Lys Tyr Asn Asp Lys Leu Pro Leu Tyr
            675                 680                 685
Ile Ser Asn Pro Asn Tyr Lys Val Asn Val Tyr Ala Val Thr Lys Glu
            690                 695                 700
Asn Thr Ile Ile Asn Pro Ser Glu Asn Gly Asp Thr Ser Thr Asn Gly
705                 710                 715                 720
Ile Lys Lys Ile Leu Ile Phe Ser Lys Lys Gly Tyr Glu Ile Gly
            725                 730                 735

<210> SEQ ID NO 7
<211> LENGTH: 735
<212> TYPE: PRT
<213> ORGANISM: Bacillus anthracis

<400> SEQUENCE: 7

Glu Val Lys Gln Glu Asn Arg Leu Leu Asn Glu Ser Glu Ser Ser Ser
1               5                   10                  15
Gln Gly Leu Leu Gly Tyr Tyr Phe Ser Asp Leu Asn Phe Gln Ala Pro
            20                  25                  30
Met Val Val Thr Ser Ser Thr Thr Gly Asp Leu Ser Ile Pro Ser Ser
            35                  40                  45
Glu Leu Glu Asn Ile Pro Ser Glu Asn Gln Tyr Phe Gln Ser Ala Ile
        50                  55                  60
Trp Ser Gly Phe Ile Lys Val Lys Lys Ser Asp Glu Tyr Thr Phe Ala
65                  70                  75                  80
Thr Ser Ala Asp Asn His Val Thr Met Trp Val Asp Asp Gln Glu Val
                85                  90                  95
Ile Asn Lys Ala Ser Asn Ser Asn Lys Ile Arg Leu Glu Lys Gly Arg
            100                 105                 110
Leu Tyr Gln Ile Lys Ile Gln Tyr Gln Arg Glu Asn Pro Thr Glu Lys
        115                 120                 125
Gly Leu Asp Phe Lys Leu Tyr Trp Thr Asp Ser Gln Asn Lys Lys Glu
    130                 135                 140
Val Ile Ser Ser Asp Asn Leu Gln Leu Pro Glu Leu Lys Gln Lys Ser
145                 150                 155                 160
Ser Asn Ser Arg Lys Lys Arg Ser Thr Ser Ala Gly Pro Thr Val Pro
                165                 170                 175
Asp Arg Asp Asn Asp Gly Ile Pro Asp Ser Leu Glu Val Glu Gly Tyr
            180                 185                 190
Thr Val Asp Val Lys Asn Lys Arg Thr Phe Leu Ser Pro Trp Ile Ser
        195                 200                 205
Asn Ile His Glu Lys Lys Gly Leu Thr Lys Tyr Lys Ser Ser Pro Glu
    210                 215                 220
Lys Trp Ser Thr Ala Ser Asp Pro Tyr Ser Asp Phe Glu Lys Val Thr
225                 230                 235                 240
Gly Arg Ile Asp Lys Asn Val Ser Pro Glu Ala Arg His Pro Leu Val
                245                 250                 255
Ala Ala Tyr Pro Ile Val His Val Asp Met Glu Asn Ile Ile Leu Ser
            260                 265                 270
Lys Asn Glu Asp Gln Ser Thr Gln Asn Thr Asp Ser Glu Thr Arg Thr
        275                 280                 285
```

-continued

```
Ile Ser Lys Asn Thr Ser Thr Ser Arg Thr His Thr Ser Glu Val His
    290                 295                 300
Gly Asn Ala Glu Val His Ala Ser Phe Phe Asp Ile Gly Gly Ser Val
305                 310                 315                 320
Ser Ala Gly Phe Ser Asn Ser Asn Ser Ser Thr Val Ala Ile Asp His
                325                 330                 335
Ser Leu Ser Leu Ala Gly Glu Arg Thr Trp Ala Glu Thr Met Gly Leu
            340                 345                 350
Asn Thr Ala Asp Thr Ala Arg Leu Asn Ala Asn Ile Arg Tyr Val Asn
        355                 360                 365
Thr Gly Thr Ala Pro Ile Tyr Asn Val Leu Pro Thr Thr Ser Leu Val
    370                 375                 380
Leu Gly Lys Asn Gln Thr Leu Ala Thr Ile Lys Ala Lys Glu Asn Gln
385                 390                 395                 400
Leu Ser Gln Ile Leu Ala Pro Asn Asn Tyr Tyr Pro Ser Lys Asn Leu
                405                 410                 415
Ala Pro Ile Ala Leu Asn Ala Gln Glu Asp Phe Ser Ser Thr Pro Ile
            420                 425                 430
Thr Met Asn Tyr Asn Gln Phe Leu Glu Leu Lys Thr Lys Gln Leu
        435                 440                 445
Arg Leu Asp Thr Asp Gln Val Tyr Gly Asn Ile Ala Thr Tyr Asn Phe
    450                 455                 460
Glu Asn Gly Arg Val Arg Val Asp Thr Gly Ser Asn Trp Ser Glu Val
465                 470                 475                 480
Leu Pro Gln Ile Gln Glu Thr Thr Ala Arg Ile Ile Phe Asn Gly Lys
                485                 490                 495
Asp Leu Asn Leu Val Glu Arg Arg Ile Ala Ala Val Asn Pro Ser Asp
            500                 505                 510
Pro Leu Glu Thr Thr Lys Pro Asp Met Thr Leu Lys Glu Ala Leu Lys
        515                 520                 525
Ile Ala Phe Gly Phe Asn Glu Pro Asn Gly Asn Leu Gln Tyr Gln Gly
    530                 535                 540
Lys Asp Ile Thr Glu Phe Asp Phe Asn Phe Asp Gln Gln Thr Ser Gln
545                 550                 555                 560
Asn Ile Lys Asn Gln Leu Ala Glu Leu Asn Ala Thr Asn Ile Tyr Thr
                565                 570                 575
Val Leu Asp Lys Ile Lys Leu Asn Ala Lys Met Asn Ile Leu Ile Arg
            580                 585                 590
Asp Lys Arg Phe His Tyr Asp Arg Asn Asn Ile Ala Val Gly Ala Asp
        595                 600                 605
Glu Ser Val Val Lys Glu Ala His Arg Glu Val Ile Asn Ser Ser Thr
    610                 615                 620
Glu Gly Leu Leu Leu Asn Ile Asp Lys Asp Ile Arg Lys Ile Leu Ser
625                 630                 635                 640
Gly Tyr Ile Val Glu Ile Glu Asp Thr Glu Gly Leu Lys Glu Val Ile
                645                 650                 655
Asn Asp Arg Tyr Asp Met Leu Asn Ile Ser Ser Leu Arg Gln Asp Gly
            660                 665                 670
Lys Thr Phe Ile Asp Phe Lys Lys Tyr Asn Asp Lys Leu Pro Leu Tyr
        675                 680                 685
Ile Ser Asn Pro Asn Tyr Lys Val Asn Val Tyr Ala Val Thr Lys Glu
    690                 695                 700
Asn Thr Ile Ile Asn Pro Ser Glu Asn Gly Asp Thr Ser Thr Asn Gly
```

```
                705                 710                 715                 720
Ile Lys Lys Ile Leu Ile Phe Ser Lys Lys Gly Tyr Glu Ile Gly
                725                 730                 735

<210> SEQ ID NO 8
<211> LENGTH: 735
<212> TYPE: PRT
<213> ORGANISM: Bacillus anthracis

<400> SEQUENCE: 8

Glu Val Lys Gln Glu Asn Arg Leu Leu Asn Glu Ser Glu Ser Ser
 1               5                  10                  15

Gln Gly Leu Leu Gly Tyr Tyr Phe Ser Asp Leu Asn Phe Gln Ala Pro
             20                  25                  30

Met Val Thr Ser Ser Thr Thr Gly Asp Leu Ser Ile Pro Ser Ser
             35                  40                  45

Glu Leu Glu Asn Ile Pro Ser Glu Asn Gln Tyr Phe Gln Ser Ala Ile
        50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Glu Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350
```

-continued

Asn Thr Ala Asp Thr Ala Arg Leu Asn Ala Asn Ile Arg Tyr Val Asn
            355                 360                 365

Thr Gly Thr Ala Pro Ile Tyr Asn Val Leu Pro Thr Thr Ser Leu Val
    370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Lys Asp Phe Ser Ser Thr Pro Ile
            420                 425                 430

Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735

<210> SEQ ID NO 9
<211> LENGTH: 735
<212> TYPE: PRT
<213> ORGANISM: Bacillus anthracis

<400> SEQUENCE: 9

```
Glu Val Lys Gln Glu Asn Arg Leu Leu Asn Glu Ser Glu Ser Ser
 1               5                  10                 15

Gln Gly Leu Leu Gly Tyr Tyr Phe Ser Asp Leu Asn Phe Gln Ala Pro
            20                  25                  30

Met Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
 50                  55                  60

Trp Ser Gly Phe Ile Lys Val Lys Ser Asp Glu Tyr Thr Phe Ala
 65                  70                  75                  80

Thr Ser Ala Asp Asn His Val Thr Met Trp Val Asp Gln Glu Val
                 85                  90                  95

Ile Asn Lys Ala Ser Asn Ser Asn Lys Ile Arg Leu Glu Lys Gly Arg
                100                 105                 110

Leu Tyr Gln Ile Lys Ile Gln Tyr Gln Arg Glu Asn Pro Thr Glu Lys
            115                 120                 125

Gly Leu Asp Phe Lys Leu Tyr Trp Thr Asp Ser Gln Asn Lys Lys Glu
130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
                180                 185                 190

Thr Val Asp Val Lys Asn Lys Arg Thr Phe Leu Ser Pro Trp Ile Ser
            195                 200                 205

Asn Ile His Glu Lys Lys Gly Leu Thr Lys Tyr Lys Ser Ser Pro Glu
            210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
                260                 265                 270

Lys Asn Glu Asp Gln Ser Thr Gln Asn Thr Asp Ser Gln Thr Arg Thr
            275                 280                 285

Ile Ser Lys Asn Thr Ser Thr Ser Arg Thr His Thr Ser Glu Val His
            290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
            355                 360                 365

Thr Gly Thr Ala Pro Ile Tyr Asn Val Leu Pro Thr Thr Ser Leu Val
370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415
```

-continued

```
Ala Pro Ile Ala Leu Asn Ala Gln Asp Asp Ala Ser Ser Thr Pro Ile
            420                 425                 430

Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
    450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735
```

<210> SEQ ID NO 10
<211> LENGTH: 735
<212> TYPE: PRT
<213> ORGANISM: Bacillus anthracis

<400> SEQUENCE: 10

```
Glu Val Lys Gln Glu Asn Arg Leu Leu Asn Glu Ser Glu Ser Ser Ser
 1               5                  10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60
```

```
Trp Ser Gly Phe Ile Lys Val Lys Lys Ser Asp Glu Tyr Thr Phe Ala
 65                  70                  75                  80

Thr Ser Ala Asp Asn His Val Thr Met Trp Val Asp Asp Gln Glu Val
                 85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
            115                 120                 125

Gly Leu Asp Phe Lys Leu Tyr Trp Thr Asp Ser Gln Asn Lys Lys Glu
            130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
            195                 200                 205

Asn Ile His Glu Lys Lys Gly Leu Thr Lys Tyr Lys Ser Ser Pro Glu
            210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Glu Thr Arg Thr
            275                 280                 285

Ile Ser Lys Asn Thr Ser Thr Ser Arg Thr His Thr Ser Glu Val His
            290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
            355                 360                 365

Thr Gly Thr Ala Pro Ile Tyr Asn Val Leu Pro Thr Thr Ser Leu Val
            370                 375                 380

Leu Gly Lys Asn Gln Thr Leu Ala Thr Ile Lys Ala Asp Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Lys Asp Phe Ser Ser Thr Pro Ile
            420                 425                 430

Thr Met Asn Tyr Asn Gln Phe Leu Glu Leu Glu Lys Thr Lys Gln Leu
            435                 440                 445

Arg Leu Asp Thr Asp Gln Val Tyr Gly Asn Ile Ala Thr Tyr Asn Phe
            450                 455                 460

Glu Asn Gly Arg Val Arg Val Asp Thr Gly Ser Asn Trp Ser Glu Val
465                 470                 475                 480
```

```
Leu Pro Gln Ile Gln Glu Thr Thr Ala Arg Ile Ile Phe Asn Gly Lys
            485                 490                 495

Asp Leu Asn Leu Val Glu Arg Arg Ile Ala Ala Val Asn Pro Ser Asp
                500                 505                 510

Pro Leu Glu Thr Thr Lys Pro Asp Met Thr Leu Lys Glu Ala Leu Lys
                515                 520                 525

Ile Ala Phe Gly Phe Asn Glu Pro Asn Gly Asn Leu Gln Tyr Gln Gly
            530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
                580                 585                 590

Asp Lys Arg Phe His Tyr Asp Arg Asn Asn Ile Ala Val Gly Ala Asp
                595                 600                 605

Glu Ser Val Val Lys Glu Ala His Arg Glu Val Ile Asn Ser Ser Thr
            610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
                660                 665                 670

Lys Thr Phe Ile Asp Phe Lys Lys Tyr Asn Asp Lys Leu Pro Leu Tyr
            675                 680                 685

Ile Ser Asn Pro Asn Tyr Lys Val Asn Val Tyr Ala Val Thr Lys Glu
            690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735
```

<210> SEQ ID NO 11
<211> LENGTH: 735
<212> TYPE: PRT
<213> ORGANISM: Bacillus anthracis

<400> SEQUENCE: 11

```
Glu Val Lys Gln Glu Asn Arg Leu Leu Asn Glu Ser Glu Ser Ser Ser
  1               5                  10                  15

Gln Gly Leu Leu Gly Tyr Tyr Phe Ser Asp Leu Asn Phe Gln Ala Pro
                20                  25                  30

Met Val Val Thr Ser Ser Thr Thr Gly Asp Leu Ser Ile Pro Ser Ser
            35                  40                  45

Glu Leu Glu Asn Ile Pro Ser Glu Asn Gln Tyr Phe Gln Ser Ala Ile
        50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125
```

-continued

```
Gly Leu Asp Phe Lys Leu Tyr Trp Thr Asp Ser Gln Asn Lys Lys Glu
    130                 135                 140
Val Ile Ser Ser Asp Asn Leu Gln Leu Pro Glu Leu Lys Gln Lys Ser
145                 150                 155                 160
Ser Asn Ser Arg Lys Lys Arg Ser Thr Ser Ala Gly Pro Thr Val Pro
                165                 170                 175
Asp Arg Asp Asn Asp Gly Ile Pro Asp Ser Leu Glu Val Glu Gly Tyr
            180                 185                 190
Thr Val Asp Val Lys Asn Lys Arg Thr Phe Leu Ser Pro Trp Ile Ser
        195                 200                 205
Asn Ile His Glu Lys Lys Gly Leu Thr Lys Tyr Lys Ser Ser Pro Glu
    210                 215                 220
Lys Trp Ser Thr Ala Ser Asp Pro Tyr Ser Asp Phe Glu Lys Val Thr
225                 230                 235                 240
Gly Arg Ile Asp Lys Asn Val Ser Pro Glu Ala Arg His Pro Leu Val
                245                 250                 255
Ala Ala Tyr Pro Ile Val His Val Asp Met Glu Asn Ile Ile Leu Ser
            260                 265                 270
Lys Asn Glu Asp Gln Ser Thr Gln Asn Thr Asp Ser Glu Thr Arg Thr
        275                 280                 285
Ile Ser Lys Asn Thr Ser Thr Ser Arg Thr His Thr Ser Glu Val His
    290                 295                 300
Gly Asn Ala Glu Val His Ala Ser Phe Phe Asp Ile Gly Gly Ser Val
305                 310                 315                 320
Ser Ala Gly Phe Ser Asn Ser Asn Ser Ser Thr Val Ala Ile Asp His
                325                 330                 335
Ser Leu Ser Leu Ala Gly Glu Arg Thr Trp Ala Glu Thr Met Gly Leu
            340                 345                 350
Asn Thr Ala Asp Thr Ala Arg Leu Asn Ala Asn Ile Arg Tyr Val Asn
        355                 360                 365
Thr Gly Thr Ala Pro Ile Tyr Asn Val Leu Pro Thr Thr Ser Leu Val
    370                 375                 380
Leu Gly Lys Asn Gln Thr Leu Ala Thr Ile Asp Ala Asp Glu Asn Gln
385                 390                 395                 400
Leu Ser Gln Ile Leu Ala Pro Asn Asn Tyr Tyr Pro Ser Lys Asn Leu
                405                 410                 415
Ala Pro Ile Ala Leu Asn Ala Gln Lys Lys Phe Ser Ser Thr Pro Ile
            420                 425                 430
Thr Met Asn Tyr Asn Gln Phe Leu Glu Leu Glu Lys Thr Lys Gln Leu
        435                 440                 445
Arg Leu Asp Thr Asp Gln Val Tyr Gly Asn Ile Ala Thr Tyr Asn Phe
    450                 455                 460
Glu Asn Gly Arg Val Arg Val Asp Thr Gly Ser Asn Trp Ser Glu Val
465                 470                 475                 480
Leu Pro Gln Ile Gln Glu Thr Thr Ala Arg Ile Ile Phe Asn Gly Lys
                485                 490                 495
Asp Leu Asn Leu Val Glu Arg Arg Ile Ala Ala Val Asn Pro Ser Asp
            500                 505                 510
Pro Leu Glu Thr Thr Lys Pro Asp Met Thr Leu Lys Glu Ala Leu Lys
        515                 520                 525
Ile Ala Phe Gly Phe Asn Glu Pro Asn Gly Asn Leu Gln Tyr Gln Gly
    530                 535                 540
```

```
Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
            565                 570                 575

Val Leu Asp Lys Ile Lys Leu Asn Ala Lys Met Asn Ile Leu Ile Arg
        580                 585                 590

Asp Lys Arg Phe His Tyr Asp Arg Asn Asn Ile Ala Val Gly Ala Asp
    595                 600                 605

Glu Ser Val Val Lys Glu Ala His Arg Glu Val Ile Asn Ser Ser Thr
610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735

<210> SEQ ID NO 12
<211> LENGTH: 711
<212> TYPE: PRT
<213> ORGANISM: Bacillus anthracis

<400> SEQUENCE: 12

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190
```

-continued

```
Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
        210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Glu Thr Arg Thr
        275                 280                 285

Ile Ser Lys Asn Thr Ser Thr Ser Arg Thr His Thr Ser Asn Ser Asn
        290                 295                 300

Ser Ser Thr Val Ala Ile Asp His Ser Leu Ser Leu Ala Gly Glu Arg
305                 310                 315                 320

Thr Trp Ala Glu Thr Met Gly Leu Asn Thr Ala Asp Thr Ala Arg Leu
                325                 330                 335

Asn Ala Asn Ile Arg Tyr Val Asn Thr Gly Thr Ala Pro Ile Tyr Asn
            340                 345                 350

Val Leu Pro Thr Thr Ser Leu Val Leu Gly Lys Asn Gln Thr Leu Ala
        355                 360                 365

Thr Ile Lys Ala Lys Glu Asn Gln Leu Ser Gln Ile Leu Ala Pro Asn
        370                 375                 380

Asn Tyr Tyr Pro Ser Lys Asn Leu Ala Pro Ile Ala Leu Asn Ala Gln
385                 390                 395                 400

Asp Asp Phe Ser Ser Thr Pro Ile Thr Met Asn Tyr Asn Gln Phe Leu
                405                 410                 415

Glu Leu Glu Lys Thr Lys Gln Leu Arg Leu Asp Thr Asp Gln Val Tyr
            420                 425                 430

Gly Asn Ile Ala Thr Tyr Asn Phe Glu Asn Gly Arg Val Arg Val Asp
        435                 440                 445

Thr Gly Ser Asn Trp Ser Glu Val Leu Pro Gln Ile Gln Glu Thr Thr
        450                 455                 460

Ala Arg Ile Ile Phe Asn Gly Lys Asp Leu Asn Leu Val Glu Arg Arg
465                 470                 475                 480

Ile Ala Ala Val Asn Pro Ser Asp Pro Leu Glu Thr Thr Lys Pro Asp
                485                 490                 495

Met Thr Leu Lys Glu Ala Leu Lys Ile Ala Phe Gly Phe Asn Glu Pro
            500                 505                 510

Asn Gly Asn Leu Gln Tyr Gln Gly Lys Asp Ile Thr Glu Phe Asp Phe
        515                 520                 525

Asn Phe Asp Gln Gln Thr Ser Gln Asn Ile Lys Asn Gln Leu Ala Glu
        530                 535                 540

Leu Asn Ala Thr Asn Ile Tyr Thr Val Leu Asp Lys Ile Lys Leu Asn
545                 550                 555                 560

Ala Lys Met Asn Ile Leu Ile Arg Asp Lys Arg Phe His Tyr Asp Arg
                565                 570                 575

Asn Asn Ile Ala Val Gly Ala Asp Glu Ser Val Val Lys Glu Ala His
            580                 585                 590

Arg Glu Val Ile Asn Ser Ser Thr Glu Gly Leu Leu Leu Asn Ile Asp
        595                 600                 605
```

```
Lys Asp Ile Arg Lys Ile Leu Ser Gly Tyr Ile Val Glu Ile Glu Asp
    610                 615                 620
Thr Glu Gly Leu Lys Glu Val Ile Asn Asp Arg Tyr Asp Met Leu Asn
625                 630                 635                 640
Ile Ser Ser Leu Arg Gln Asp Gly Lys Thr Phe Ile Asp Phe Lys Lys
                    645                 650                 655
Tyr Asn Asp Lys Leu Pro Leu Tyr Ile Ser Asn Pro Asn Tyr Lys Val
                660                 665                 670
Asn Val Tyr Ala Val Thr Lys Glu Asn Thr Ile Ile Asn Pro Ser Glu
            675                 680                 685
Asn Gly Asp Thr Ser Thr Asn Gly Ile Lys Lys Ile Leu Ile Phe Ser
690                 695                 700
Lys Lys Gly Tyr Glu Ile Gly
705                 710

<210> SEQ ID NO 13
<211> LENGTH: 735
<212> TYPE: PRT
<213> ORGANISM: Bacillus anthracis

<400> SEQUENCE: 13

Glu Val Lys Gln Glu Asn Arg Leu Leu Asn Glu Ser Glu Ser Ser Ser
1               5                   10                  15
Gln Gly Leu Leu Gly Tyr Tyr Phe Ser Asp Leu Asn Phe Gln Ala Pro
                20                  25                  30
Met Val Val Thr Ser Ser Thr Thr Gly Asp Leu Ser Ile Pro Ser Ser
            35                  40                  45
Glu Leu Glu Asn Ile Pro Ser Glu Asn Gln Tyr Phe Gln Ser Ala Ile
50                  55                  60
Trp Ser Gly Phe Ile Lys Val Lys Lys Ser Asp Glu Tyr Thr Phe Ala
65                  70                  75                  80
Thr Ser Ala Asp Asn His Val Thr Met Trp Val Asp Asp Gln Glu Val
                85                  90                  95
Ile Asn Lys Ala Ser Asn Ser Asn Lys Ile Arg Leu Glu Lys Gly Arg
            100                 105                 110
Leu Tyr Gln Ile Lys Ile Gln Tyr Gln Arg Glu Asn Pro Thr Glu Lys
        115                 120                 125
Gly Leu Asp Phe Lys Leu Tyr Trp Thr Asp Ser Gln Asn Lys Lys Glu
    130                 135                 140
Val Ile Ser Ser Asp Asn Leu Gln Leu Pro Glu Leu Lys Gln Lys Ser
145                 150                 155                 160
Ser Asn Ser Arg Lys Lys Arg Ser Thr Ser Ala Gly Pro Thr Val Pro
                165                 170                 175
Asp Arg Asp Asn Asp Gly Ile Pro Asp Ser Leu Glu Val Glu Gly Tyr
            180                 185                 190
Thr Val Asp Val Lys Asn Lys Arg Thr Phe Leu Ser Pro Trp Ile Ser
        195                 200                 205
Asn Ile His Glu Lys Lys Gly Leu Thr Lys Tyr Lys Ser Ser Pro Glu
    210                 215                 220
Lys Trp Ser Thr Ala Ser Asp Pro Tyr Ser Asp Phe Glu Lys Val Thr
225                 230                 235                 240
Gly Arg Ile Asp Lys Asn Val Ser Pro Glu Ala Arg His Pro Leu Val
                245                 250                 255
Ala Ala Tyr Pro Ile Val His Val Asp Met Glu Asn Ile Ile Leu Ser
            260                 265                 270
```

-continued

```
Lys Asn Glu Asp Gln Ser Thr Gln Asn Thr Asp Ser Glu Thr Arg Thr
            275                 280                 285

Ile Ser Lys Asn Thr Ser Thr Ser Arg Thr His Thr Ser Glu Val His
        290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
            355                 360                 365

Thr Gly Thr Ala Pro Ile Tyr Asn Val Leu Pro Thr Thr Ser Leu Val
        370                 375                 380

Leu Gly Lys Asn Gln Thr Leu Ala Thr Ile Lys Ala Asp Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Lys Asp Ala Ser Ser Thr Pro Ile
            420                 425                 430

Thr Met Asn Tyr Asn Gln Phe Leu Glu Leu Lys Thr Lys Gln Leu
            435                 440                 445

Arg Leu Asp Thr Asp Gln Val Tyr Gly Asn Ile Ala Thr Tyr Asn Phe
    450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685
```

-continued

Ile Ser Asn Pro Asn Tyr Lys Val Asn Val Tyr Ala Val Thr Lys Glu
    690             695             700

Asn Thr Ile Ile Asn Pro Ser Glu Asn Gly Asp Thr Ser Thr Asn Gly
705             710             715             720

Ile Lys Lys Ile Leu Ile Phe Ser Lys Lys Gly Tyr Glu Ile Gly
            725             730             735

<210> SEQ ID NO 14
<211> LENGTH: 711
<212> TYPE: PRT
<213> ORGANISM: Bacillus anthracis

<400> SEQUENCE: 14

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Gly Asp Leu Ser Ile Pro Ser Ser
            35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Glu Thr Arg Thr
        275                 280                 285

Ile Ser Lys Asn Thr Ser Thr Ser Arg Thr His Thr Ser Asn Ser Asn
    290                 295                 300

Ser Ser Thr Val Ala Ile Asp His Ser Leu Ser Leu Ala Gly Glu Arg
305                 310                 315                 320

Thr Trp Ala Glu Thr Met Gly Leu Asn Thr Ala Asp Thr Ala Arg Leu
                325                 330                 335

```
Asn Ala Asn Ile Arg Tyr Val Asn Thr Gly Thr Ala Pro Ile Tyr Asn
            340                 345                 350

Val Leu Pro Thr Thr Ser Leu Val Leu Gly Lys Asn Gln Thr Leu Ala
            355                 360                 365

Thr Ile Lys Ala Lys Glu Asn Gln Leu Ser Gln Ile Leu Ala Pro Asn
            370                 375                 380

Asn Tyr Tyr Pro Ser Lys Asn Leu Ala Pro Ile Ala Leu Asn Ala Gln
385                 390                 395                 400

Asp Asp Ala Ser Ser Thr Pro Ile Thr Met Asn Tyr Asn Gln Phe Leu
                405                 410                 415

Glu Leu Glu Lys Thr Lys Gln Leu Arg Leu Asp Thr Asp Gln Val Tyr
            420                 425                 430

Gly Asn Ile Ala Thr Tyr Asn Phe Glu Asn Gly Arg Val Arg Val Asp
            435                 440                 445

Thr Gly Ser Asn Trp Ser Glu Val Leu Pro Gln Ile Gln Glu Thr Thr
            450                 455                 460

Ala Arg Ile Ile Phe Asn Gly Lys Asp Leu Asn Leu Val Glu Arg Arg
465                 470                 475                 480

Ile Ala Ala Val Asn Pro Ser Asp Pro Leu Glu Thr Thr Lys Pro Asp
                485                 490                 495

Met Thr Leu Lys Glu Ala Leu Lys Ile Ala Phe Gly Phe Asn Glu Pro
            500                 505                 510

Asn Gly Asn Leu Gln Tyr Gln Gly Lys Asp Ile Thr Glu Phe Asp Phe
            515                 520                 525

Asn Phe Asp Gln Gln Thr Ser Gln Asn Ile Lys Asn Gln Leu Ala Glu
            530                 535                 540

Leu Asn Ala Thr Asn Ile Tyr Thr Val Leu Asp Lys Ile Lys Leu Asn
545                 550                 555                 560

Ala Lys Met Asn Ile Leu Ile Arg Asp Lys Arg Phe His Tyr Asp Arg
                565                 570                 575

Asn Asn Ile Ala Val Gly Ala Asp Glu Ser Val Val Lys Glu Ala His
            580                 585                 590

Arg Glu Val Ile Asn Ser Ser Thr Glu Gly Leu Leu Leu Asn Ile Asp
            595                 600                 605

Lys Asp Ile Arg Lys Ile Leu Ser Gly Tyr Ile Val Glu Ile Glu Asp
610                 615                 620

Thr Glu Gly Leu Lys Glu Val Ile Asn Asp Arg Tyr Asp Met Leu Asn
625                 630                 635                 640

Ile Ser Ser Leu Arg Gln Asp Gly Lys Thr Phe Ile Asp Phe Lys Lys
                645                 650                 655

Tyr Asn Asp Lys Leu Pro Leu Tyr Ile Ser Asn Pro Asn Tyr Lys Val
            660                 665                 670

Asn Val Tyr Ala Val Thr Lys Glu Asn Thr Ile Ile Asn Pro Ser Glu
            675                 680                 685

Asn Gly Asp Thr Ser Thr Asn Gly Ile Lys Lys Ile Leu Ile Phe Ser
            690                 695                 700

Lys Lys Gly Tyr Glu Ile Gly
705                 710

<210> SEQ ID NO 15
<211> LENGTH: 711
<212> TYPE: PRT
<213> ORGANISM: Bacillus anthracis
```

-continued

<400> SEQUENCE: 15

```
Glu Val Lys Gln Glu Asn Arg Leu Leu Asn Glu Ser Glu Ser Ser
 1               5                  10                  15

Gln Gly Leu Leu Gly Tyr Tyr Phe Ser Asp Leu Asn Phe Gln Ala Pro
             20                  25                  30

Met Val Val Thr Ser Ser Thr Thr Gly Asp Leu Ser Ile Pro Ser Ser
             35                  40                  45

Glu Leu Glu Asn Ile Pro Ser Glu Asn Gln Tyr Phe Gln Ser Ala Ile
         50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                 85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
            115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Glu Thr Arg Thr
        275                 280                 285

Ile Ser Lys Asn Thr Ser Thr Ser Arg Thr His Thr Ser Asn Ser Asn
    290                 295                 300

Ser Ser Thr Val Ala Ile Asp His Ser Leu Ser Leu Ala Gly Glu Arg
305                 310                 315                 320

Thr Trp Ala Glu Thr Met Gly Leu Asn Thr Ala Asp Thr Ala Arg Leu
                325                 330                 335

Asn Ala Asn Ile Arg Tyr Val Asn Thr Gly Thr Ala Pro Ile Tyr Asn
            340                 345                 350

Val Leu Pro Thr Thr Ser Leu Val Leu Gly Lys Asn Gln Thr Leu Ala
        355                 360                 365

Thr Ile Lys Ala Asp Glu Asn Gln Leu Ser Gln Ile Leu Ala Pro Asn
    370                 375                 380

Asn Tyr Tyr Pro Ser Lys Asn Leu Ala Pro Ile Ala Leu Asn Ala Gln
385                 390                 395                 400

Asp Asp Ala Ser Ser Thr Pro Ile Thr Met Asn Tyr Asn Gln Phe Leu
                405                 410                 415
```

-continued

Glu Leu Glu Lys Thr Lys Gln Leu Arg Leu Asp Thr Asp Gln Val Tyr
            420                 425                 430

Gly Asn Ile Ala Thr Tyr Asn Phe Glu Asn Gly Arg Val Arg Val Asp
            435                 440                 445

Thr Gly Ser Asn Trp Ser Glu Val Leu Pro Gln Ile Gln Glu Thr Thr
            450                 455                 460

Ala Arg Ile Ile Phe Asn Gly Lys Asp Leu Asn Leu Val Glu Arg Arg
465                 470                 475                 480

Ile Ala Ala Val Asn Pro Ser Asp Pro Leu Glu Thr Thr Lys Pro Asp
                485                 490                 495

Met Thr Leu Lys Glu Ala Leu Lys Ile Ala Phe Gly Phe Asn Glu Pro
            500                 505                 510

Asn Gly Asn Leu Gln Tyr Gln Gly Lys Asp Ile Thr Glu Phe Asp Phe
            515                 520                 525

Asn Phe Asp Gln Gln Thr Ser Gln Asn Ile Lys Asn Gln Leu Ala Glu
            530                 535                 540

Leu Asn Ala Thr Asn Ile Tyr Thr Val Leu Asp Lys Ile Lys Leu Asn
545                 550                 555                 560

Ala Lys Met Asn Ile Leu Ile Arg Asp Lys Arg Phe His Tyr Asp Arg
                565                 570                 575

Asn Asn Ile Ala Val Gly Ala Asp Glu Ser Val Val Lys Glu Ala His
            580                 585                 590

Arg Glu Val Ile Asn Ser Ser Thr Glu Gly Leu Leu Leu Asn Ile Asp
            595                 600                 605

Lys Asp Ile Arg Lys Ile Leu Ser Gly Tyr Ile Val Glu Ile Glu Asp
            610                 615                 620

Thr Glu Gly Leu Lys Glu Val Ile Asn Asp Arg Tyr Asp Met Leu Asn
625                 630                 635                 640

Ile Ser Ser Leu Arg Gln Asp Gly Lys Thr Phe Ile Asp Phe Lys Lys
                645                 650                 655

Tyr Asn Asp Lys Leu Pro Leu Tyr Ile Ser Asn Pro Asn Tyr Lys Val
            660                 665                 670

Asn Val Tyr Ala Val Thr Lys Glu Asn Thr Ile Ile Asn Pro Ser Glu
            675                 680                 685

Asn Gly Asp Thr Ser Thr Asn Gly Ile Lys Lys Ile Leu Ile Phe Ser
            690                 695                 700

Lys Lys Gly Tyr Glu Ile Gly
705                 710

<210> SEQ ID NO 16
<211> LENGTH: 711
<212> TYPE: PRT
<213> ORGANISM: Bacillus anthracis

<400> SEQUENCE: 16

Glu Val Lys Gln Glu Asn Arg Leu Leu Asn Glu Ser Glu Ser Ser Ser
  1               5                  10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
            35                  40                  45

Glu Leu Glu Asn Ile Pro Ser Glu Asn Gln Tyr Phe Gln Ser Ala Ile
            50                  55                  60

Trp Ser Gly Phe Ile Lys Val Lys Lys Ser Asp Glu Tyr Thr Phe Ala

-continued

```
             65                  70                  75                  80
Thr Ser Ala Asp Asn His Val Thr Met Trp Val Asp Gln Glu Val
                85                  90                  95
Ile Asn Lys Ala Ser Asn Ser Asn Lys Ile Arg Leu Glu Lys Gly Arg
                100                 105                 110
Leu Tyr Gln Ile Lys Ile Gln Tyr Gln Arg Glu Asn Pro Thr Glu Lys
                115                 120                 125
Gly Leu Asp Phe Lys Leu Tyr Trp Thr Asp Ser Gln Asn Lys Lys Glu
                130                 135                 140
Val Ile Ser Ser Asp Asn Leu Gln Leu Pro Glu Leu Lys Gln Lys Ser
145                 150                 155                 160
Ser Asn Ser Arg Lys Lys Arg Ser Thr Ala Gly Pro Thr Val Pro
                165                 170                 175
Asp Arg Asp Asn Asp Gly Ile Pro Asp Ser Leu Glu Val Glu Gly Tyr
                180                 185                 190
Thr Val Asp Val Lys Asn Lys Arg Thr Phe Leu Ser Pro Trp Ile Ser
                195                 200                 205
Asn Ile His Glu Lys Lys Gly Leu Thr Lys Tyr Lys Ser Ser Pro Glu
                210                 215                 220
Lys Trp Ser Thr Ala Ser Asp Pro Tyr Ser Asp Phe Glu Lys Val Thr
225                 230                 235                 240
Gly Arg Ile Asp Lys Asn Val Ser Pro Glu Ala Arg His Pro Leu Val
                245                 250                 255
Ala Ala Tyr Pro Ile Val His Val Asp Met Glu Asn Ile Ile Leu Ser
                260                 265                 270
Lys Asn Glu Asp Gln Ser Thr Gln Asn Thr Asp Ser Glu Thr Arg Thr
                275                 280                 285
Ile Ser Lys Asn Thr Ser Thr Ser Arg Thr His Thr Ser Asn Ser Asn
                290                 295                 300
Ser Ser Thr Val Ala Ile Asp His Ser Leu Ser Leu Ala Gly Glu Arg
305                 310                 315                 320
Thr Trp Ala Glu Thr Met Gly Leu Asn Thr Ala Asp Thr Ala Arg Leu
                325                 330                 335
Asn Ala Asn Ile Arg Tyr Val Asn Thr Gly Thr Ala Pro Ile Tyr Asn
                340                 345                 350
Val Leu Pro Thr Thr Ser Leu Val Leu Gly Lys Asn Gln Thr Leu Ala
                355                 360                 365
Thr Ile Lys Ala Asp Glu Asn Gln Leu Ser Gln Ile Leu Ala Pro Asn
                370                 375                 380
Asn Tyr Tyr Pro Ser Lys Asn Leu Ala Pro Ile Ala Leu Asn Ala Gln
385                 390                 395                 400
Lys Asp Ala Ser Ser Thr Pro Ile Thr Met Asn Tyr Asn Gln Phe Leu
                405                 410                 415
Glu Leu Glu Lys Thr Lys Gln Leu Arg Leu Asp Thr Asp Gln Val Tyr
                420                 425                 430
Gly Asn Ile Ala Thr Tyr Asn Phe Glu Asn Gly Arg Val Arg Val Asp
                435                 440                 445
Thr Gly Ser Asn Trp Ser Glu Val Leu Pro Gln Ile Gln Glu Thr Thr
                450                 455                 460
Ala Arg Ile Ile Phe Asn Gly Lys Asp Leu Asn Leu Val Glu Arg Arg
465                 470                 475                 480
Ile Ala Ala Val Asn Pro Ser Asp Pro Leu Glu Thr Thr Lys Pro Asp
                485                 490                 495
```

```
Met Thr Leu Lys Glu Ala Leu Lys Ile Ala Phe Gly Phe Asn Glu Pro
        500                 505                 510

Asn Gly Asn Leu Gln Tyr Gln Gly Lys Asp Ile Thr Glu Phe Asp Phe
            515                 520                 525

Asn Phe Asp Gln Gln Thr Ser Gln Asn Ile Lys Asn Gln Leu Ala Glu
        530                 535                 540

Leu Asn Ala Thr Asn Ile Tyr Thr Val Leu Asp Lys Ile Lys Leu Asn
545                 550                 555                 560

Ala Lys Met Asn Ile Leu Ile Arg Asp Lys Arg Phe His Tyr Asp Arg
                565                 570                 575

Asn Asn Ile Ala Val Gly Ala Asp Glu Ser Val Val Lys Glu Ala His
            580                 585                 590

Arg Glu Val Ile Asn Ser Ser Thr Glu Gly Leu Leu Leu Asn Ile Asp
                595                 600                 605

Lys Asp Ile Arg Lys Ile Leu Ser Gly Tyr Ile Val Glu Ile Glu Asp
        610                 615                 620

Thr Glu Gly Leu Lys Glu Val Ile Asn Asp Arg Tyr Asp Met Leu Asn
625                 630                 635                 640

Ile Ser Ser Leu Arg Gln Asp Gly Lys Thr Phe Ile Asp Phe Lys Lys
                645                 650                 655

Tyr Asn Asp Lys Leu Pro Leu Tyr Ile Ser Asn Pro Asn Tyr Lys Val
            660                 665                 670

Asn Val Tyr Ala Val Thr Lys Glu Asn Thr Ile Ile Asn Pro Ser Glu
        675                 680                 685

Asn Gly Asp Thr Ser Thr Asn Gly Ile Lys Lys Ile Leu Ile Phe Ser
    690                 695                 700

Lys Lys Gly Tyr Glu Ile Gly
705                 710

<210> SEQ ID NO 17
<211> LENGTH: 735
<212> TYPE: PRT
<213> ORGANISM: Bacillus anthracis

<400> SEQUENCE: 17

Glu Val Lys Gln Glu Asn Arg Leu Leu Asn Glu Ser Glu Ser Ser Ser
  1               5                  10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
```

```
                145                 150                 155                 160
Ser Asn Ser Arg Lys Arg Ser Thr Ser Ala Gly Pro Thr Val Pro
                    165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
            245                 250                 255

Ala Ala Tyr Pro Ile Val His Val Asp Met Glu Asn Ile Ile Leu Ser
        260                 265                 270

Lys Asn Glu Asp Gln Ser Thr Gln Asn Thr Asp Ser Glu Thr Arg Thr
    275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
    370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Asp Ser Ser Thr Pro Ile
            420                 425                 430

Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
    450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575
```

```
Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
            595                 600                 605

Glu Ser Val Val Lys Glu Ala His Arg Glu Val Ile Asn Ser Ser Thr
            610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                    645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
            675                 680                 685

Ile Ser Asn Pro Asn Tyr Lys Val Asn Val Tyr Ala Val Thr Lys Glu
            690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                    725                 730                 735

<210> SEQ ID NO 18
<211> LENGTH: 735
<212> TYPE: PRT
<213> ORGANISM: Bacillus anthracis

<400> SEQUENCE: 18

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
            35                  40                  45

Glu Leu Glu Asn Ile Pro Ser Glu Asn Gln Tyr Phe Gln Ser Ala Ile
50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
            85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
            115                 120                 125

Gly Leu Asp Phe Lys Leu Tyr Trp Thr Asp Ser Gln Asn Lys Lys Glu
130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
            165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
            195                 200                 205

Asn Ile His Glu Lys Lys Gly Leu Thr Lys Tyr Lys Ser Ser Pro Glu
```

-continued

```
            210                 215                 220
Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
                260                 265                 270

Lys Asn Glu Asp Gln Ser Thr Gln Asn Thr Asp Ser Glu Thr Arg Thr
            275                 280                 285

Ile Ser Lys Asn Thr Ser Thr Ser Arg Thr His Thr Ser Glu Val His
        290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Lys Ser Ser Thr Pro Ile
                420                 425                 430

Thr Met Asn Tyr Asn Gln Phe Leu Glu Leu Glu Lys Thr Lys Gln Leu
            435                 440                 445

Arg Leu Asp Thr Asp Gln Val Tyr Gly Asn Ile Ala Thr Tyr Asn Phe
        450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
610                 615                 620

Glu Gly Leu Leu Leu Asn Ile Asp Lys Asp Ile Arg Lys Ile Leu Ser
625                 630                 635                 640
```

-continued

```
Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735

<210> SEQ ID NO 19
<211> LENGTH: 735
<212> TYPE: PRT
<213> ORGANISM: Bacillus anthracis
<220> FEATURE:
<221> NAME/KEY: VARIANT
<222> LOCATION: 397
<223> OTHER INFORMATION: Xaa = any amino acid except Lys

<400> SEQUENCE: 19

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255
```

-continued

```
Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Glu Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
            325                 330                 335

Ser Leu Ser Leu Ala Gly Glu Arg Thr Trp Ala Glu Thr Met Gly Leu
        340                 345                 350

Asn Thr Ala Asp Thr Ala Arg Leu Asn Ala Asn Ile Arg Tyr Val Asn
    355                 360                 365

Thr Gly Thr Ala Pro Ile Tyr Asn Val Leu Pro Thr Thr Ser Leu Val
370                 375                 380

Leu Gly Lys Asn Gln Thr Leu Ala Thr Ile Lys Ala Xaa Glu Asn Gln
385                 390                 395                 400

Leu Ser Gln Ile Leu Ala Pro Asn Asn Tyr Tyr Pro Ser Lys Asn Leu
            405                 410                 415

Ala Pro Ile Ala Leu Asn Ala Gln Asp Asp Phe Ser Ser Thr Pro Ile
        420                 425                 430

Thr Met Asn Tyr Asn Gln Phe Leu Glu Leu Glu Lys Thr Lys Gln Leu
    435                 440                 445

Arg Leu Asp Thr Asp Gln Val Tyr Gly Asn Ile Ala Thr Tyr Asn Phe
450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
            485                 490                 495

Asp Leu Asn Leu Val Glu Arg Arg Ile Ala Ala Val Asn Pro Ser Asp
        500                 505                 510

Pro Leu Glu Thr Thr Lys Pro Asp Met Thr Leu Lys Glu Ala Leu Lys
    515                 520                 525

Ile Ala Phe Gly Phe Asn Glu Pro Asn Gly Asn Leu Gln Tyr Gln Gly
530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
            565                 570                 575

Val Leu Asp Lys Ile Lys Leu Asn Ala Lys Met Asn Ile Leu Ile Arg
        580                 585                 590

Asp Lys Arg Phe His Tyr Asp Arg Asn Asn Ile Ala Val Gly Ala Asp
    595                 600                 605

Glu Ser Val Val Lys Glu Ala His Arg Glu Val Ile Asn Ser Ser Thr
610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
            645                 650                 655

Asn Asp Arg Tyr Asp Met Leu Asn Ile Ser Ser Leu Arg Gln Asp Gly
        660                 665                 670

Lys Thr Phe Ile Asp Phe Lys Lys Tyr Asn Asp Lys Leu Pro Leu Tyr
```

```
                675                 680                 685
Ile Ser Asn Pro Asn Tyr Lys Val Asn Val Tyr Ala Val Thr Lys Glu
        690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735

<210> SEQ ID NO 20
<211> LENGTH: 735
<212> TYPE: PRT
<213> ORGANISM: Bacillus anthracis

<400> SEQUENCE: 20

Glu Val Lys Gln Glu Asn Arg Leu Leu Asn Glu Ser Glu Ser Ser Ser
  1               5                  10                  15

Gln Gly Leu Leu Gly Tyr Tyr Phe Ser Asp Leu Asn Phe Gln Ala Pro
             20                  25                  30

Met Val Val Thr Ser Ser Thr Thr Gly Asp Leu Ser Ile Pro Ser Ser
         35                  40                  45

Glu Leu Glu Asn Ile Pro Ser Glu Asn Gln Tyr Phe Gln Ser Ala Ile
 50                  55                  60

Trp Ser Gly Phe Ile Lys Val Lys Lys Ser Asp Glu Tyr Thr Phe Ala
 65                  70                  75                  80

Thr Ser Ala Asp Asn His Val Thr Met Trp Val Asp Asp Gln Glu Val
                 85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Glu Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320
```

-continued

```
Ser Ala Gly Phe Ser Asn Ser Asn Ser Ser Thr Val Ala Ile Asp His
            325                 330                 335

Ser Leu Ser Leu Ala Gly Glu Arg Thr Trp Ala Glu Thr Met Gly Leu
        340                 345                 350

Asn Thr Ala Asp Thr Ala Arg Leu Asn Ala Asn Ile Arg Tyr Val Asn
            355                 360                 365

Thr Gly Thr Ala Pro Ile Tyr Asn Val Leu Pro Thr Thr Ser Leu Val
    370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Phe Ser Ser Thr Pro Ile
            420                 425                 430

Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
    450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735
```

<210> SEQ ID NO 21
<211> LENGTH: 735
<212> TYPE: PRT
<213> ORGANISM: Bacillus anthracis

<400> SEQUENCE: 21

Glu Val Lys Gln Glu Asn Arg Leu Leu Asn Glu Ser Glu Ser Ser Ser
 1               5                  10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Glu Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
    370                 375                 380

| | | | | | | | | | | | |
|---|---|---|---|---|---|---|---|---|---|---|---|
Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
            405                 410                 415

Ala Pro Ile Ala Leu Asn Ala Gln Asp Asp Phe Ser Ser Thr Pro Ile
        420                 425                 430

Thr Met Asn Tyr Asn Gln Phe Leu Glu Leu Glu Lys Thr Lys Gln Leu
            435                 440                 445

Arg Leu Asp Thr Asp Gln Val Tyr Gly Asn Ile Ala Thr Tyr Asn Phe
        450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
            485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
        530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
            565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
            645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
            675                 680                 685

Ile Ser Asn Pro Asn Tyr Lys Val Asn Val Tyr Ala Val Thr Lys Glu
        690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
            725                 730                 735

<210> SEQ ID NO 22
<211> LENGTH: 2208
<212> TYPE: DNA
<213> ORGANISM: Bacillus anthracis

<400> SEQUENCE: 22
gaagttaaac aggagaaccg gttattaaat gaatcagaat caagttccca ggggttacta    60
ggatactatt ttagtgattt gaattttcaa gcacccatgg tggttacctc ttctactaca   120
ggggatttat ctattcctag ttctgagtta gaaaatattc catcggaaaa ccaatatttt   180

```
caatctgcta tttggtcagg atttatcaaa gttaagaaga gtgatgaata tacatttgct    240
acttccgctg ataatcatgt aacaatgtgg gtagatgacc aagaagtgat taataaagct    300
tctaattcta acaaaatcag attagaaaaa ggaagattat atcaaataaa aattcaatat    360
caacgagaaa atcctactga aaaggattg gatttcaagt tgtactggac cgattctcaa     420
aataaaaaag aagtgatttc tagtgataac ttacaattgc cagaattaaa acaaaaatct    480
tcgaactcaa gaaaaagcg aagtacaagt gctggaccta cggttccaga ccgtgacaat     540
gatggaatcc ctgattcatt agaggtagaa ggatatacgg ttgatgtcaa aaataaaaga    600
acttttcttt caccatggat tctaatatt catgaaaaga aggattaac caaatataaa      660 tcatctcctg aaaatggag cacggcttct gatccgtaca gtgatttcga aaaggttaca     720
ggacggattg ataagaatgt atcaccagag gcaagacacc cccttgtggc agcttatccg    780
attgtacatg tagatatgga gaatattatt ctctcaaaaa atgaggatca atccacacag    840
aatactgata gtgaaacgag aacaataagt aaaaatactt ctacaagtag gacacatact    900
agtgaagtac atggaaatgc agaagtgcat gcgtcgttct ttgatattgg tgggagtgta    960
tctgcaggat ttagtaattc gaattcaagt acggtcgcaa ttgatcattc actatctcta    1020 gcagggaaa gaacttgggc tgaaacaatg ggtttaaata ccgctgatac agcaagatta    1080
aatgccaata ttagatatgt aaatactggg acggctccaa tctacaacgt gttaccaacg    1140
acttcgttag tgttaggaaa aaatcaaaca ctcgcgacaa ttaaagctaa ggaaaaccaa    1200
ttaagtcaaa tacttgcacc taataattat tatccttcta aaaacttggc gccaatcgca    1260
ttaaatgcac aagacgattt cagttctact ccaattacaa tgaattacaa tcaatttctt    1320
gagttagaaa aaacgaaaca attaagatta gatacggatc aagtatatgg gaatatagca    1380
acatacaatt ttgaaaatgg aagagtgagg gtggatacag gctcgaactg gagtgaagtg    1440
ttaccgcaaa ttcaagaaac aactgcacgt atcatttta atggaaaaga tttaaatctg     1500
gtagaaaggc ggatagcggc ggttaatcct agtgatccat tagaaacgac taaaccggat    1560
atgacattaa aagaagccct taaaatagca tttggattta acgaaccgaa tggaaactta    1620
caatatcaag ggaaagacat aaccgaattt gattttaatt tcgatcaaca acatctcaa     1680 aatatcaaga atcagttagc ggaattaaac gcaactaaca tatatactgt attagataaa    1740
atcaaattaa atgcaaaaat gaatatttta ataagagata aacgttttca ttatgataga    1800
aataacatag cagttggggc ggatgagtca gtagttaagg aggctcatag agaagtaatt    1860
aattcgtcaa cagagggatt attgttaaat attgataagg atataagaaa aatattatca    1920
ggttatattg tagaaattga agatactgaa gggcttaaag aagttataaa tgacagatat    1980
gatatgttga atatttctag tttacggcaa gatggaaaaa catttataga ttttaaaaaa    2040
tataatgata aattaccgtt atatataagt aatcccaatt ataaggtaaa tgtatatgct    2100
gttactaaag aaaacactat tattaatcct agtgagaatg gggatactag taccaacggg    2160
atcaagaaaa tttaatctt ttctaaaaaa ggctatgaga taggataa                  2208
```

<210> SEQ ID NO 23
<211> LENGTH: 735
<212> TYPE: PRT
<213> ORGANISM: Bacillus anthracis
<220> FEATURE:
<221> NAME/KEY: VARIANT
<222> LOCATION: 427
<223> OTHER INFORMATION: Xaa = any amino acid except Phe

<400> SEQUENCE: 23

| | | | | | | | | | | | | | | |
|---|---|---|---|---|---|---|---|---|---|---|---|---|---|---|
| Glu | Val | Lys | Gln | Glu | Asn | Arg | Leu | Leu | Asn | Glu | Ser | Glu | Ser | Ser | Ser |
| 1 | | | | 5 | | | | | 10 | | | | | 15 | |
| Gln | Gly | Leu | Leu | Gly | Tyr | Tyr | Phe | Ser | Asp | Leu | Asn | Phe | Gln | Ala | Pro |
| | | | 20 | | | | | 25 | | | | | 30 | | |
| Met | Val | Val | Thr | Ser | Ser | Thr | Thr | Gly | Asp | Leu | Ser | Ile | Pro | Ser | Ser |
| | | | 35 | | | | | 40 | | | | | 45 | | |
| Glu | Leu | Glu | Asn | Ile | Pro | Ser | Glu | Asn | Gln | Tyr | Phe | Gln | Ser | Ala | Ile |
| | 50 | | | | | 55 | | | | | 60 | | | | |
| Trp | Ser | Gly | Phe | Ile | Lys | Val | Lys | Lys | Ser | Asp | Glu | Tyr | Thr | Phe | Ala |
| 65 | | | | | 70 | | | | | 75 | | | | | 80 |
| Thr | Ser | Ala | Asp | Asn | His | Val | Thr | Met | Trp | Val | Asp | Asp | Gln | Glu | Val |
| | | | | 85 | | | | | 90 | | | | | 95 | |
| Ile | Asn | Lys | Ala | Ser | Asn | Ser | Asn | Lys | Ile | Arg | Leu | Glu | Lys | Gly | Arg |
| | | | 100 | | | | | 105 | | | | | 110 | | |
| Leu | Tyr | Gln | Ile | Lys | Ile | Gln | Tyr | Gln | Arg | Glu | Asn | Pro | Thr | Glu | Lys |
| | | | 115 | | | | | 120 | | | | | 125 | | |
| Gly | Leu | Asp | Phe | Lys | Leu | Tyr | Trp | Thr | Asp | Ser | Gln | Asn | Lys | Lys | Glu |
| | 130 | | | | | 135 | | | | | 140 | | | | |
| Val | Ile | Ser | Ser | Asp | Asn | Leu | Gln | Leu | Pro | Glu | Leu | Lys | Gln | Lys | Ser |
| 145 | | | | | 150 | | | | | 155 | | | | | 160 |
| Ser | Asn | Ser | Arg | Lys | Lys | Arg | Ser | Thr | Ser | Ala | Gly | Pro | Thr | Val | Pro |
| | | | | 165 | | | | | 170 | | | | | 175 | |
| Asp | Arg | Asp | Asn | Asp | Gly | Ile | Pro | Asp | Ser | Leu | Glu | Val | Glu | Gly | Tyr |
| | | | 180 | | | | | 185 | | | | | 190 | | |
| Thr | Val | Asp | Val | Lys | Asn | Lys | Arg | Thr | Phe | Leu | Ser | Pro | Trp | Ile | Ser |
| | | | 195 | | | | | 200 | | | | | 205 | | |
| Asn | Ile | His | Glu | Lys | Lys | Gly | Leu | Thr | Lys | Tyr | Lys | Ser | Ser | Pro | Glu |
| | 210 | | | | | 215 | | | | | 220 | | | | |
| Lys | Trp | Ser | Thr | Ala | Ser | Asp | Pro | Tyr | Ser | Asp | Phe | Glu | Lys | Val | Thr |
| 225 | | | | | 230 | | | | | 235 | | | | | 240 |
| Gly | Arg | Ile | Asp | Lys | Asn | Val | Ser | Pro | Glu | Ala | Arg | His | Pro | Leu | Val |
| | | | | 245 | | | | | 250 | | | | | 255 | |
| Ala | Ala | Tyr | Pro | Ile | Val | His | Val | Asp | Met | Glu | Asn | Ile | Ile | Leu | Ser |
| | | | 260 | | | | | 265 | | | | | 270 | | |
| Lys | Asn | Glu | Asp | Gln | Ser | Thr | Gln | Asn | Thr | Asp | Ser | Glu | Thr | Arg | Thr |
| | | | 275 | | | | | 280 | | | | | 285 | | |
| Ile | Ser | Lys | Asn | Thr | Ser | Thr | Ser | Arg | Thr | His | Thr | Ser | Glu | Val | His |
| | | 290 | | | | | 295 | | | | | 300 | | | |
| Gly | Asn | Ala | Glu | Val | His | Ala | Ser | Phe | Phe | Asp | Ile | Gly | Gly | Ser | Val |
| 305 | | | | | 310 | | | | | 315 | | | | | 320 |
| Ser | Ala | Gly | Phe | Ser | Asn | Ser | Asn | Ser | Ser | Thr | Val | Ala | Ile | Asp | His |
| | | | | 325 | | | | | 330 | | | | | 335 | |
| Ser | Leu | Ser | Leu | Ala | Gly | Glu | Arg | Thr | Trp | Ala | Glu | Thr | Met | Gly | Leu |
| | | | 340 | | | | | 345 | | | | | 350 | | |
| Asn | Thr | Ala | Asp | Thr | Ala | Arg | Leu | Asn | Ala | Asn | Ile | Arg | Tyr | Val | Asn |
| | | | 355 | | | | | 360 | | | | | 365 | | |
| Thr | Gly | Thr | Ala | Pro | Ile | Tyr | Asn | Val | Leu | Pro | Thr | Thr | Ser | Leu | Val |
| | | 370 | | | | | 375 | | | | | 380 | | | |
| Leu | Gly | Lys | Asn | Gln | Thr | Leu | Ala | Thr | Ile | Lys | Ala | Lys | Glu | Asn | Gln |
| 385 | | | | | 390 | | | | | 395 | | | | | 400 |
| Leu | Ser | Gln | Ile | Leu | Ala | Pro | Asn | Asn | Tyr | Tyr | Pro | Ser | Lys | Asn | Leu |
| | | | | 405 | | | | | 410 | | | | | 415 | |

```
Ala Pro Ile Ala Leu Asn Ala Gln Asp Asp Xaa Ser Ser Thr Pro Ile
        420                 425                 430
Thr Met Asn Tyr Asn Gln Phe Leu Glu Leu Glu Lys Thr Lys Gln Leu
        435                 440                 445
Arg Leu Asp Thr Asp Gln Val Tyr Gly Asn Ile Ala Thr Tyr Asn Phe
        450                 455                 460
Glu Asn Gly Arg Val Arg Val Asp Thr Gly Ser Asn Trp Ser Glu Val
465                 470                 475                 480
Leu Pro Gln Ile Gln Glu Thr Thr Ala Arg Ile Ile Phe Asn Gly Lys
                485                 490                 495
Asp Leu Asn Leu Val Glu Arg Arg Ile Ala Ala Val Asn Pro Ser Asp
                500                 505                 510
Pro Leu Glu Thr Thr Lys Pro Asp Met Thr Leu Lys Glu Ala Leu Lys
                515                 520                 525
Ile Ala Phe Gly Phe Asn Glu Pro Asn Gly Asn Leu Gln Tyr Gln Gly
        530                 535                 540
Lys Asp Ile Thr Glu Phe Asp Phe Asn Phe Asp Gln Gln Thr Ser Gln
545                 550                 555                 560
Asn Ile Lys Asn Gln Leu Ala Glu Leu Asn Ala Thr Asn Ile Tyr Thr
                565                 570                 575
Val Leu Asp Lys Ile Lys Leu Asn Ala Lys Met Asn Ile Leu Ile Arg
                580                 585                 590
Asp Lys Arg Phe His Tyr Asp Arg Asn Asn Ile Ala Val Gly Ala Asp
        595                 600                 605
Glu Ser Val Val Lys Glu Ala His Arg Glu Val Ile Asn Ser Ser Thr
610                 615                 620
Glu Gly Leu Leu Leu Asn Ile Asp Lys Asp Ile Arg Lys Ile Leu Ser
625                 630                 635                 640
Gly Tyr Ile Val Glu Ile Glu Asp Thr Glu Gly Leu Lys Glu Val Ile
                645                 650                 655
Asn Asp Arg Tyr Asp Met Leu Asn Ile Ser Ser Leu Arg Gln Asp Gly
                660                 665                 670
Lys Thr Phe Ile Asp Phe Lys Lys Tyr Asn Asp Lys Leu Pro Leu Tyr
        675                 680                 685
Ile Ser Asn Pro Asn Tyr Lys Val Asn Val Tyr Ala Val Thr Lys Glu
        690                 695                 700
Asn Thr Ile Ile Asn Pro Ser Glu Asn Gly Asp Thr Ser Thr Asn Gly
705                 710                 715                 720
Ile Lys Lys Ile Leu Ile Phe Ser Lys Lys Gly Tyr Glu Ile Gly
                725                 730                 735

<210> SEQ ID NO 24
<211> LENGTH: 599
<212> TYPE: PRT
<213> ORGANISM: Bacillus anthracis

<400> SEQUENCE: 24

Thr Asp Ser Gln Asn Lys Lys Glu Val Ile Ser Ser Asp Asn Leu Gln
1               5                   10                  15
Leu Pro Glu Leu Lys Gln Lys Ser Ser Asn Ser Arg Lys Lys Arg Ser
                20                  25                  30
Thr Ser Ala Gly Pro Thr Val Pro Asp Arg Asp Asn Asp Gly Ile Pro
        35                  40                  45
Asp Ser Leu Glu Val Glu Gly Tyr Thr Val Asp Val Lys Asn Lys Arg
```

-continued

```
               50                  55                  60
Thr Phe Leu Ser Pro Trp Ile Ser Asn Ile His Glu Lys Lys Gly Leu
 65                  70                  75                  80

Thr Lys Tyr Lys Ser Ser Pro Glu Lys Trp Ser Thr Ala Ser Asp Pro
                 85                  90                  95

Tyr Ser Asp Phe Glu Lys Val Thr Gly Arg Ile Asp Lys Asn Val Ser
                100                 105                 110

Pro Glu Ala Arg His Pro Leu Val Ala Ala Tyr Pro Ile Val His Val
                115                 120                 125

Asp Met Glu Asn Ile Ile Leu Ser Lys Asn Asp Gln Ser Thr Gln
            130                 135                 140

Asn Thr Asp Ser Gln Thr Arg Thr Ile Ser Lys Asn Thr Ser Thr Ser
145                 150                 155                 160

Arg Thr His Thr Ser Glu Val His Gly Asn Ala Glu Val His Ala Ser
                165                 170                 175

Phe Phe Asp Ile Gly Gly Ser Val Ser Ala Gly Phe Ser Asn Ser Asn
                180                 185                 190

Ser Ser Thr Val Ala Ile Asp His Ser Leu Ser Leu Ala Gly Glu Arg
                195                 200                 205

Thr Trp Ala Glu Thr Met Gly Leu Asn Thr Ala Asp Thr Ala Arg Leu
210                 215                 220

Asn Ala Asn Ile Arg Tyr Val Asn Thr Gly Thr Ala Pro Ile Tyr Asn
225                 230                 235                 240

Val Leu Pro Thr Thr Ser Leu Val Leu Gly Lys Asn Gln Thr Leu Ala
                245                 250                 255

Thr Ile Lys Ala Lys Glu Asn Gln Leu Ser Gln Ile Leu Ala Pro Asn
                260                 265                 270

Asn Tyr Tyr Pro Ser Lys Asn Leu Ala Pro Ile Ala Leu Asn Ala Gln
                275                 280                 285

Asp Asp Phe Ser Ser Thr Pro Ile Thr Met Asn Tyr Asn Gln Phe Leu
            290                 295                 300

Glu Leu Glu Lys Thr Lys Gln Leu Arg Leu Asp Thr Asp Gln Val Tyr
305                 310                 315                 320

Gly Asn Ile Ala Thr Tyr Asn Phe Glu Asn Gly Arg Val Arg Val Asp
                325                 330                 335

Thr Gly Ser Asn Trp Ser Glu Val Leu Pro Gln Ile Gln Glu Thr Thr
                340                 345                 350

Ala Arg Ile Ile Phe Asn Gly Lys Asp Leu Asn Leu Val Glu Arg Arg
                355                 360                 365

Ile Ala Ala Val Asn Pro Ser Asp Pro Leu Glu Thr Thr Lys Pro Asp
            370                 375                 380

Met Thr Leu Lys Glu Ala Leu Lys Ile Ala Phe Gly Phe Asn Glu Pro
385                 390                 395                 400

Asn Gly Asn Leu Gln Tyr Gln Gly Lys Asp Ile Thr Glu Phe Asp Phe
                405                 410                 415

Asn Phe Asp Gln Gln Thr Ser Gln Asn Ile Lys Asn Gln Leu Ala Glu
                420                 425                 430

Leu Asn Val Thr Asn Ile Tyr Thr Val Leu Asp Lys Ile Lys Leu Asn
                435                 440                 445

Ala Lys Met Asn Ile Leu Ile Arg Asp Lys Arg Phe His Tyr Asp Arg
            450                 455                 460

Asn Asn Ile Ala Val Gly Ala Asp Glu Ser Val Val Lys Glu Ala His
465                 470                 475                 480
```

-continued

Arg Glu Val Ile Asn Ser Ser Thr Glu Gly Leu Leu Leu Asn Ile Asp
485 490 495

Lys Asp Ile Arg Lys Ile Leu Ser Gly Tyr Ile Val Glu Ile Glu Asp
500 505 510

Thr Glu Gly Leu Lys Glu Val Ile Asn Asp Arg Tyr Asp Met Leu Asn
515 520 525

Ile Ser Ser Leu Arg Gln Asp Gly Lys Thr Phe Ile Asp Phe Lys Lys
530 535 540

Tyr Asn Asp Lys Leu Pro Leu Tyr Ile Ser Asn Pro Asn Tyr Lys Val
545 550 555 560

Asn Val Tyr Ala Val Thr Lys Glu Asn Thr Ile Ile Asn Pro Ser Glu
565 570 575

Asn Gly Asp Thr Ser Thr Asn Gly Ile Lys Lys Ile Leu Ile Phe Ser
580 585 590

Lys Lys Gly Tyr Glu Ile Gly
595

<210> SEQ ID NO 25
<211> LENGTH: 705
<212> TYPE: PRT
<213> ORGANISM: Clostridium difficile

<400> SEQUENCE: 25

Glu Leu Asp Gly Met Lys Lys Ile Ile Pro Glu Glu Asn Leu Phe Leu
1 5 10 15

Arg Asp Tyr Ser Asn Ile Glu Lys Asp Asp Pro Phe Ile Pro Asn Asn
20 25 30

Asn Phe Phe Asp Pro Lys Leu Met Ser Asp Trp Glu Asp Glu Asp Leu
35 40 45

Asp Thr Asp Asn Asp Asn Ile Pro Asp Ser Tyr Glu Arg Asn Gly Tyr
50 55 60

Thr Ile Lys Asp Leu Ile Ala Val Lys Trp Glu Asp Ser Phe Ala Glu
65 70 75 80

Gln Gly Tyr Lys Lys Tyr Val Ser Asn Tyr Leu Glu Ser Asn Thr Ala
85 90 95

Gly Asp Pro Tyr Thr Asp Tyr Glu Lys Ala Ser Gly Ser Phe Asp Lys
100 105 110

Ala Ile Lys Thr Glu Ala Arg Asp Pro Leu Val Ala Ala Tyr Pro Ile
115 120 125

Val Gly Val Gly Met Glu Lys Leu Ile Ile Ser Thr Asn Glu His Ala
130 135 140

Ser Thr Asp Gln Gly Lys Thr Val Ser Arg Ala Thr Thr Asn Ser Lys
145 150 155 160

Thr Glu Ser Asn Thr Ala Gly Val Ser Val Asn Val Gly Tyr Gln Asn
165 170 175

Gly Phe Thr Ala Asn Val Thr Thr Asn Tyr Ser His Thr Thr Asp Asn
180 185 190

Ser Thr Ala Val Gln Asp Ser Asn Gly Glu Ser Trp Asn Thr Gly Leu
195 200 205

Ser Ile Asn Lys Gly Glu Ser Ala Tyr Ile Asn Ala Asn Val Arg Tyr
210 215 220

Tyr Asn Thr Gly Thr Ala Pro Met Tyr Lys Val Thr Pro Thr Thr Asn
225 230 235 240

Leu Val Leu Asp Gly Asp Thr Leu Ser Thr Ile Lys Ala Gln Glu Asn

-continued

```
                245                 250                 255
Gln Ile Gly Asn Asn Leu Ser Pro Gly Asp Thr Tyr Pro Lys Lys Gly
                260                 265                 270
Leu Ser Pro Leu Ala Leu Asn Thr Met Asp Gln Phe Ser Ser Arg Leu
            275                 280                 285
Ile Pro Ile Asn Tyr Asp Gln Leu Lys Lys Leu Asp Ala Gly Lys Gln
        290                 295                 300
Ile Lys Leu Glu Thr Thr Gln Val Ser Gly Asn Phe Gly Thr Lys Asn
305                 310                 315                 320
Ser Ser Gly Gln Ile Val Thr Glu Gly Asn Ser Trp Ser Asp Tyr Ile
                325                 330                 335
Ser Gln Ile Asp Ser Ile Ser Ala Ser Ile Leu Asp Thr Glu Asn
                340                 345                 350
Glu Ser Tyr Glu Arg Arg Val Thr Ala Lys Asn Leu Gln Asp Pro Glu
            355                 360                 365
Asp Lys Thr Pro Glu Leu Thr Ile Gly Glu Ala Ile Glu Lys Ala Phe
        370                 375                 380
Gly Ala Thr Lys Lys Asp Gly Leu Leu Tyr Phe Asn Asp Ile Pro Ile
385                 390                 395                 400
Asp Glu Ser Cys Val Glu Leu Ile Phe Asp Asp Asn Thr Ala Asn Lys
                405                 410                 415
Ile Lys Asp Ser Leu Lys Thr Leu Ser Asp Lys Lys Ile Tyr Asn Val
                420                 425                 430
Lys Leu Glu Arg Gly Met Asn Ile Leu Ile Lys Thr Pro Thr Tyr Phe
            435                 440                 445
Thr Asn Phe Asp Asp Tyr Asn Asn Tyr Pro Ser Thr Trp Ser Asn Val
        450                 455                 460
Asn Thr Thr Asn Gln Asp Gly Leu Gln Gly Ser Ala Asn Lys Leu Asn
465                 470                 475                 480
Gly Glu Thr Lys Ile Lys Ile Pro Met Ser Glu Leu Lys Pro Tyr Lys
                485                 490                 495
Arg Tyr Val Phe Ser Gly Tyr Ser Lys Asp Pro Leu Thr Ser Asn Ser
            500                 505                 510
Ile Ile Val Lys Ile Lys Ala Lys Glu Glu Lys Thr Asp Tyr Leu Val
        515                 520                 525
Pro Glu Gln Gly Tyr Thr Lys Phe Ser Tyr Glu Phe Glu Thr Thr Glu
        530                 535                 540
Lys Asp Ser Ser Asn Ile Glu Ile Thr Leu Ile Gly Ser Gly Thr Thr
545                 550                 555                 560
Tyr Leu Asp Asn Leu Ser Ile Thr Glu Leu Asn Ser Thr Pro Glu Ile
                565                 570                 575
Leu Asp Glu Pro Glu Val Lys Ile Pro Thr Asp Gln Glu Ile Met Asp
            580                 585                 590
Ala His Lys Ile Tyr Phe Ala Asp Leu Asn Phe Asn Pro Ser Thr Gly
        595                 600                 605
Asn Thr Tyr Ile Asn Gly Met Tyr Phe Ala Pro Thr Gln Thr Asn Lys
        610                 615                 620
Glu Ala Leu Asp Tyr Ile Gln Lys Tyr Arg Val Glu Ala Thr Leu Gln
625                 630                 635                 640
Tyr Ser Gly Phe Lys Asp Ile Gly Thr Lys Asp Lys Glu Met Arg Asn
            645                 650                 655
Tyr Leu Gly Asp Pro Asn Gln Pro Lys Thr Asn Tyr Val Asn Leu Arg
        660                 665                 670
```

-continued

```
Ser Tyr Phe Thr Gly Gly Glu Asn Ile Met Thr Tyr Lys Lys Leu Arg
            675                 680                 685

Ile Tyr Ala Ile Thr Pro Asp Asp Arg Glu Leu Leu Val Leu Ser Val
        690                 695                 700

Asp
705

<210> SEQ ID NO 26
<211> LENGTH: 706
<212> TYPE: PRT
<213> ORGANISM: Clostridium perfringens

<400> SEQUENCE: 26

Glu Leu Asn Gly Asn Lys Thr Val Ile Pro Glu Glu Asn Leu Phe Phe
  1               5                  10                  15

Arg Asp Tyr Ser Lys Ile Asp Glu Asn Asp Pro Phe Ile Pro Asn Asn
             20                  25                  30

Asn Phe Phe Asp Val Arg Phe Phe Ser Ala Ala Trp Glu Asp Glu Asp
         35                  40                  45

Leu Asp Thr Asp Asn Asp Asn Ile Pro Asp Ala Tyr Glu Lys Asn Gly
     50                  55                  60

Tyr Thr Ile Lys Asp Ser Ile Ala Val Lys Trp Asn Asp Ser Phe Ala
 65                  70                  75                  80

Glu Gln Gly Tyr Lys Lys Tyr Val Ser Ser Tyr Leu Glu Ser Asn Thr
                 85                  90                  95

Ala Gly Asp Pro Tyr Thr Asp Tyr Gln Lys Ala Ser Gly Ser Ile Asp
            100                 105                 110

Lys Ala Ile Lys Leu Glu Ala Arg Asp Pro Leu Val Ala Ala Tyr Pro
        115                 120                 125

Val Val Gly Val Gly Met Glu Asn Leu Ile Ile Ser Thr Asn Glu His
    130                 135                 140

Ala Ser Ser Asp Gln Gly Lys Thr Val Ser Arg Ala Thr Thr Asn Ser
145                 150                 155                 160

Lys Thr Asp Ala Asn Thr Val Gly Val Ser Ile Ser Ala Gly Tyr Gln
                165                 170                 175

Asn Gly Phe Thr Gly Asn Ile Thr Thr Ser Tyr Ser His Thr Thr Asp
            180                 185                 190

Asn Ser Thr Ala Val Gln Asp Ser Asn Gly Glu Ser Trp Asn Thr Gly
        195                 200                 205

Leu Ser Ile Asn Lys Gly Glu Ser Ala Tyr Ile Asn Ala Asn Val Arg
    210                 215                 220

Tyr Tyr Asn Thr Gly Thr Ala Pro Met Tyr Lys Val Thr Pro Thr Thr
225                 230                 235                 240

Asn Leu Val Leu Asp Gly Glu Thr Leu Ala Thr Ile Lys Ala Gln Asp
                245                 250                 255

Asn Gln Ile Gly Asn Asn Leu Ser Pro Asn Glu Thr Tyr Pro Lys Lys
            260                 265                 270

Gly Leu Ser Pro Leu Ala Leu Asn Thr Met Asp Gln Phe Asn Ala Arg
        275                 280                 285

Leu Ile Pro Ile Asn Tyr Asp Gln Leu Lys Lys Leu Asp Ser Gly Lys
    290                 295                 300

Gln Ile Lys Leu Glu Thr Thr Gln Val Ser Gly Asn Tyr Gly Thr Lys
305                 310                 315                 320

Asn Ser Gln Gly Gln Ile Ile Thr Glu Gly Asn Ser Trp Ser Asn Tyr
```

```
                    325                 330                 335
Ile Ser Gln Ile Asp Ser Val Ser Ala Ser Ile Ile Leu Asp Thr Gly
                340                 345                 350
Ser Gln Thr Phe Glu Arg Arg Val Ala Ala Lys Glu Gln Gly Asn Pro
                355                 360                 365
Glu Asp Lys Thr Pro Glu Ile Thr Ile Gly Glu Ala Ile Lys Lys Ala
            370                 375                 380
Phe Ser Ala Thr Lys Asn Gly Glu Leu Leu Tyr Phe Asn Gly Ile Pro
385                 390                 395                 400
Ile Asp Glu Ser Cys Val Glu Leu Ile Phe Asp Asp Asn Thr Ser Glu
                405                 410                 415
Ile Ile Lys Glu Gln Leu Lys Tyr Leu Asp Asp Lys Lys Ile Tyr Asn
                420                 425                 430
Val Lys Leu Glu Arg Gly Met Asn Ile Leu Ile Lys Val Pro Ser Tyr
                435                 440                 445
Phe Thr Asn Phe Asp Glu Tyr Asn Asn Phe Pro Ala Ser Trp Ser Asn
                450                 455                 460
Ile Asp Thr Lys Asn Gln Asp Gly Leu Gln Ser Val Ala Asn Lys Leu
465                 470                 475                 480
Ser Gly Glu Thr Lys Ile Ile Pro Met Ser Lys Leu Lys Pro Tyr
                485                 490                 495
Lys Arg Tyr Val Phe Ser Gly Tyr Ser Lys Asp Pro Ser Thr Ser Asn
                500                 505                 510
Ser Ile Thr Val Asn Ile Lys Ser Lys Glu Gln Lys Thr Asp Tyr Leu
                515                 520                 525
Val Pro Glu Lys Asp Tyr Thr Lys Phe Ser Tyr Glu Phe Glu Thr Thr
            530                 535                 540
Gly Lys Asp Ser Ser Asp Ile Glu Ile Thr Leu Thr Ser Ser Gly Val
545                 550                 555                 560
Ile Phe Leu Asp Asn Leu Ser Ile Thr Glu Leu Asn Ser Thr Pro Glu
                565                 570                 575
Ile Leu Lys Glu Pro Glu Ile Lys Val Pro Ser Asp Gln Glu Ile Leu
                580                 585                 590
Asp Ala His Asn Lys Tyr Tyr Ala Asp Ile Lys Leu Asp Thr Asn Thr
                595                 600                 605
Gly Asn Thr Tyr Ile Asp Gly Ile Tyr Phe Glu Pro Thr Gln Thr Asn
            610                 615                 620
Lys Glu Ala Leu Asp Tyr Ile Gln Lys Tyr Arg Val Glu Ala Thr Leu
625                 630                 635                 640
Gln Tyr Ser Gly Phe Lys Asp Ile Gly Thr Lys Asp Lys Glu Ile Arg
                645                 650                 655
Asn Tyr Leu Gly Asp Gln Asn Gln Pro Lys Thr Asn Tyr Ile Asn Phe
            660                 665                 670
Arg Ser Tyr Phe Thr Ser Gly Glu Asn Val Met Thr Tyr Lys Lys Leu
                675                 680                 685
Arg Ile Tyr Ala Val Thr Pro Asp Asn Arg Glu Leu Leu Val Leu Ser
            690                 695                 700
Val Asn
705

<210> SEQ ID NO 27
<211> LENGTH: 712
<212> TYPE: PRT
<213> ORGANISM: Clostridium spiroforme
```

<400> SEQUENCE: 27

```
Glu Leu Asn Gly Asp Lys Thr Leu Ile Pro Glu Lys Asn Leu Phe Leu
 1               5                  10                  15

Arg Asp Tyr Ser Lys Ile Asp Glu Asn Asp Pro Phe Ile Pro Lys Asp
            20                  25                  30

Asn Phe Phe Asp Leu Lys Leu Lys Ser Arg Ser Ala Arg Leu Ala Ser
        35                  40                  45

Gly Trp Gly Asp Glu Asp Leu Asp Thr Asp Asn Asp Asn Ile Pro Asp
    50                  55                  60

Ala Tyr Glu Lys Asn Gly Tyr Thr Ile Lys Asp Ser Ile Ala Val Lys
65                  70                  75                  80

Trp Glu Asp Ser Phe Ala Gln Gln Gly Tyr Lys Lys Tyr Leu Ser Ser
                85                  90                  95

Tyr Leu Glu Ser Asn Thr Ala Gly Asp Pro Tyr Thr Asp Tyr Gln Lys
            100                 105                 110

Ala Ser Gly Ser Phe Asp Lys Ala Ile Lys Ala Glu Ala Arg Asp Pro
        115                 120                 125

Leu Val Ala Ala Tyr Pro Val Val Gly Val Gly Met Glu Lys Leu Ile
    130                 135                 140

Ile Ser Thr Asn Glu His Ala Ser Thr Asp Gln Gly Lys Thr Val Ser
145                 150                 155                 160

Arg Asn Thr Thr Asn Ser Lys Thr Asp Ala Asn Thr Ala Gly Val Ala
                165                 170                 175

Ile Asn Ile Ala Tyr Gln Asn Gly Phe Thr Gly Ser Ile Thr Thr Asn
            180                 185                 190

Tyr Ser His Thr Thr Glu Asn Ser Thr Ala Val Gln Asn Ser Asn Gly
        195                 200                 205

Glu Ser Trp Asn Thr Ser Leu Ser Ile Asn Lys Gly Glu Ser Ala Tyr
    210                 215                 220

Ile Asn Ala Asn Val Arg Tyr Tyr Asn Thr Gly Thr Ala Pro Met Tyr
225                 230                 235                 240

Lys Val Thr Pro Thr Thr Asn Leu Val Leu Asp Gly Asp Thr Leu Thr
                245                 250                 255

Thr Ile Lys Ala Gln Asp Asn Gln Ile Gly Asn Asn Leu Ser Pro Asn
            260                 265                 270

Glu Thr Tyr Pro Lys Lys Gly Leu Ser Pro Leu Ala Leu Asn Thr Met
        275                 280                 285

Asp Gln Phe Ser Ser Arg Leu Ile Pro Ile Asn Tyr Asp Gln Leu Lys
    290                 295                 300

Lys Leu Asp Ala Gly Lys Gln Ile Lys Leu Glu Thr Thr Gln Val Ser
305                 310                 315                 320

Gly Asn Tyr Gly Ile Lys Asn Ser Gln Gly Gln Ile Ile Thr Glu Gly
                325                 330                 335

Asn Ser Trp Ser Asp Tyr Ile Ser Gln Ile Asp Ser Leu Ser Ala Ser
            340                 345                 350

Ile Ile Leu Asp Thr Gly Ser Asp Val Phe Glu Arg Arg Val Thr Ala
        355                 360                 365

Lys Asp Ser Ser Asn Pro Glu Asp Lys Thr Pro Val Leu Thr Ile Gly
    370                 375                 380

Glu Ala Ile Glu Lys Ala Phe Gly Ala Thr Lys Asn Gly Glu Ile Leu
385                 390                 395                 400

Tyr Phe Asn Gly Met Pro Ile Asp Glu Ser Cys Val Glu Leu Ile Phe
```

```
                405                 410                 415
Asp Gly Asn Thr Ala Asn Leu Ile Lys Glu Arg Leu Asn Ala Leu Asn
            420                 425                 430

Asp Lys Lys Ile Tyr Asn Val Gln Leu Glu Arg Gly Met Lys Ile Leu
            435                 440             445

Ile Lys Thr Ser Thr Tyr Phe Asn Asn Phe Asp Gly Tyr Asn Asn Phe
            450                 455             460

Pro Ser Ser Trp Ser Asn Val Asp Ser Asn Gln Asp Gly Leu Gln
465                 470                 475                 480

Asn Ala Asn Lys Leu Ser Gly Glu Thr Lys Ile Val Ile Pro Met
                485                 490                 495

Ser Lys Leu Asn Pro Tyr Lys Arg Tyr Val Phe Ser Gly Tyr Leu Lys
            500                 505             510

Asn Ser Ser Thr Ser Asn Pro Ile Thr Val Asn Ile Lys Ala Lys Glu
            515                 520             525

Gln Lys Thr Tyr Asn Leu Val Ser Glu Asn Asp Tyr Lys Lys Phe Ser
            530                 535             540

Tyr Glu Phe Glu Thr Ile Gly Arg Asp Ala Ser Asn Ile Glu Ile Thr
545                 550                 555                 560

Leu Thr Ser Ser Gly Thr Ile Phe Leu Asp Asn Leu Ser Ile Thr Glu
                565                 570                 575

Leu Asn Ser Thr Pro Glu Ile Leu Lys Glu Pro Asp Ile Lys Val Pro
            580                 585             590

Ser Asp Gln Glu Ile Ile Asp Ala His Lys Lys Tyr Tyr Ala Asp Leu
            595                 600             605

Ser Phe Asn Gln Ser Thr Ala Asn Tyr Tyr Leu Asp Gly Leu Tyr Phe
            610                 615             620

Glu Pro Thr Gln Thr Asn Lys Glu Val Leu Asp Tyr Ile Gln Lys Tyr
625                 630                 635                 640

Lys Val Glu Ala Thr Leu Glu Tyr Ser Gly Phe Lys Asp Ile Gly Thr
                645                 650                 655

Lys Asp Lys Glu Leu Arg Asn Tyr Thr Gly Asp Ser Asn Gln Pro Lys
            660                 665             670

Thr Asn Tyr Val Asn Phe Arg Ser Tyr Phe Thr Ser Gly Glu Asn Val
            675                 680             685

Met Pro Tyr Lys Lys Leu Arg Ile Tyr Ala Ile Thr Pro Glu Asn Lys
            690                 695             700

Glu Leu Leu Val Leu Ser Ile Asn
705                 710

<210> SEQ ID NO 28
<211> LENGTH: 582
<212> TYPE: PRT
<213> ORGANISM: Clostridium botulinum

<400> SEQUENCE: 28

Glu Thr Ser Asp Ile Ile Lys Glu Ile Pro Ser Glu Val Leu Leu
1               5                   10                  15

Lys Pro Asn Tyr Ser Asn Thr Asn Glu Lys Ser Lys Phe Ile Pro Asn
            20                  25                  30

Asn Thr Leu Phe Ser Asn Ala Lys Leu Lys Ala Asn Ala Asn Arg Asp
            35                  40                  45

Thr Asp Arg Asp Gly Ile Pro Asp Glu Trp Glu Ile Asn Gly Tyr Thr
        50                  55                  60
```

-continued

```
Val Met Asn Gln Lys Ala Val Ala Trp Asp Asp Lys Phe Ala Ala Asn
 65                  70                  75                  80

Gly Tyr Lys Lys Tyr Val Ser Asn Pro Phe Lys Pro Cys Thr Ala Asn
                 85                  90                  95

Asp Pro Tyr Thr Asp Phe Glu Lys Val Ser Gly Gln Ile Asp Pro Ser
            100                 105                 110

Val Ser Met Val Ala Arg Asp Pro Met Ile Ser Ala Tyr Pro Ile Val
        115                 120                 125

Gly Val Gln Met Glu Arg Leu Val Val Ser Lys Ser Glu Thr Ile Thr
130                 135                 140

Gly Asp Ser Thr Lys Ser Met Ser Lys Ser Thr Ser His Ser Ser Thr
145                 150                 155                 160

Asn Ile Asn Thr Val Gly Ala Glu Val Ser Gly Ser Leu Gln Leu Ala
                165                 170                 175

Gly Gly Ile Phe Pro Val Phe Ser Met Ser Ala Ser Ala Asn Tyr Ser
            180                 185                 190

His Thr Trp Gln Asn Thr Ser Thr Val Asp Asp Thr Thr Gly Glu Ser
        195                 200                 205

Phe Ser Gln Gly Leu Ser Ile Asn Thr Gly Ser Ala Tyr Ile Asn
210                 215                 220

Pro Asn Ile Arg Tyr Tyr Asn Thr Gly Thr Ala Pro Val Tyr Asn Val
225                 230                 235                 240

Thr Pro Thr Thr Thr Ile Val Ile Asp Lys Gln Ser Val Ala Thr Ile
                245                 250                 255

Lys Gly Gln Glu Ser Leu Ile Gly Asp Tyr Leu Asn Pro Gly Gly Thr
            260                 265                 270

Tyr Pro Ile Ile Gly Glu Pro Met Ala Leu Asn Thr Met Asp Gln
        275                 280                 285

Phe Ser Ser Arg Leu Ile Pro Ile Asn Tyr Asn Gln Leu Lys Ser Ile
290                 295                 300

Asp Asn Gly Gly Thr Val Met Leu Ser Thr Ser Gln Phe Thr Gly Asn
305                 310                 315                 320

Phe Ala Lys Tyr Asn Ser Asn Gly Asn Leu Val Thr Asp Gly Asn Asn
                325                 330                 335

Trp Gly Pro Tyr Leu Gly Thr Ile Lys Ser Thr Thr Ala Ser Leu Thr
            340                 345                 350

Leu Ser Phe Ser Gly Gln Thr Thr Gln Val Ala Val Ala Pro Asn
        355                 360                 365

Phe Ser Asp Pro Glu Asp Lys Thr Pro Lys Leu Thr Leu Glu Gln Ala
370                 375                 380

Leu Val Lys Ala Phe Ala Leu Glu Lys Lys Asn Gly Lys Phe Tyr Phe
385                 390                 395                 400

His Gly Leu Glu Ile Ser Lys Asn Glu Lys Ile Gln Val Phe Leu Asp
                405                 410                 415

Ser Asn Thr Asn Asn Asp Phe Glu Asn Gln Leu Lys Asn Thr Ala Asp
            420                 425                 430

Lys Asp Ile Met His Cys Ile Ile Lys Arg Asn Met Asn Ile Leu Val
        435                 440                 445

Lys Val Ile Thr Phe Lys Glu Asn Ile Ser Ile Asn Ile Ile Asn
450                 455                 460

Asp Thr Asn Phe Gly Val Gln Ser Met Thr Gly Leu Ser Asn Arg Ser
465                 470                 475                 480

Lys Gly Gln Asp Gly Ile Tyr Arg Ala Ala Thr Thr Ala Phe Ser Phe
```

-continued

```
                485                 490                 495

Lys Ser Lys Glu Leu Lys Tyr Pro Glu Gly Arg Tyr Arg Met Arg Phe
            500                 505                 510

Val Ile Gln Ser Tyr Glu Pro Phe Thr Cys Asn Phe Lys Leu Phe Asn
        515                 520                 525

Asn Leu Ile Tyr Ser Ser Ser Phe Asp Lys Gly Tyr Tyr Asp Glu Phe
    530                 535                 540

Phe Tyr Phe Tyr Tyr Asn Gly Ser Lys Ser Phe Phe Asn Ile Ser Cys
545                 550                 555                 560

Asp Ile Ile Asn Ser Ile Asn Arg Leu Ser Gly Val Phe Leu Ile Glu
                565                 570                 575

Leu Asp Lys Leu Ile Ile
            580

<210> SEQ ID NO 29
<211> LENGTH: 708
<212> TYPE: PRT
<213> ORGANISM: Bacillus cereus

<400> SEQUENCE: 29

Ile Asp Ser Gln Asn Gln Pro Gln Gln Val Gln Gln Asp Glu Leu Arg
 1               5                  10                  15

Asn Pro Glu Phe Asn Lys Lys Glu Ser Gln Glu Phe Leu Ala Lys Pro
            20                  25                  30

Ser Lys Ile Asn Leu Phe Thr Gln Gln Met Lys Arg Glu Ile Asp Glu
        35                  40                  45

Asp Thr Asp Thr Asp Gly Asp Ser Ile Pro Asp Leu Trp Glu Glu Asn
    50                  55                  60

Gly Tyr Thr Ile Gln Asn Arg Ile Ala Val Lys Trp Asp Asp Ser Leu
65                  70                  75                  80

Ala Ser Lys Gly Tyr Thr Lys Phe Val Ser Asn Pro Leu Glu Ser His
                85                  90                  95

Thr Val Gly Asp Pro Tyr Thr Asp Tyr Glu Lys Ala Ala Arg Asp Leu
            100                 105                 110

Asp Leu Ser Asn Ala Lys Glu Thr Phe Asn Pro Leu Val Ala Ala Phe
        115                 120                 125

Pro Ser Val Asn Val Ser Met Glu Lys Val Ile Leu Ser Pro Asn Glu
    130                 135                 140

Asn Leu Ser Asn Ser Val Glu Ser His Ser Ser Thr Asn Trp Ser Tyr
145                 150                 155                 160

Thr Asn Thr Glu Gly Ala Ser Val Glu Ala Gly Ile Gly Pro Lys Gly
                165                 170                 175

Ile Ser Phe Gly Val Ser Val Asn Tyr Gln His Ser Glu Thr Val Ala
            180                 185                 190

Gln Glu Trp Gly Thr Ser Thr Gly Asn Thr Ser Gln Phe Asn Thr Ala
        195                 200                 205

Ser Ala Gly Tyr Leu Asn Ala Asn Val Arg Tyr Asn Asn Val Gly Thr
    210                 215                 220

Gly Ala Ile Tyr Asp Val Lys Pro Thr Thr Ser Phe Val Leu Asn Asn
225                 230                 235                 240

Asp Thr Ile Ala Thr Ile Thr Ala Lys Ser Asn Ser Thr Ala Leu Asn
                245                 250                 255

Ile Ser Pro Gly Glu Ser Tyr Pro Lys Lys Gly Gln Asn Gly Ile Ala
            260                 265                 270
```

```
Ile Thr Ser Met Asp Asp Phe Asn Ser His Pro Ile Thr Leu Asn Lys
        275                 280                 285

Lys Gln Val Asp Asn Leu Leu Asn Asn Lys Pro Met Met Leu Glu Thr
        290                 295                 300

Asn Gln Thr Asp Gly Val Tyr Lys Ile Lys Asp Thr His Gly Asn Ile
305                 310                 315                 320

Val Thr Gly Gly Glu Trp Asn Gly Val Ile Gln Gln Ile Lys Ala Lys
                325                 330                 335

Thr Ala Ser Ile Ile Val Asp Asp Gly Glu Arg Val Ala Glu Lys Arg
                340                 345                 350

Val Ala Ala Lys Asp Tyr Glu Asn Pro Glu Asp Lys Thr Pro Ser Leu
                355                 360                 365

Thr Leu Lys Asp Ala Leu Lys Leu Ser Tyr Pro Asp Glu Ile Lys Glu
        370                 375                 380

Ile Glu Gly Leu Leu Tyr Tyr Lys Asn Lys Pro Ile Tyr Glu Ser Ser
385                 390                 395                 400

Val Met Thr Tyr Leu Asp Glu Asn Thr Ala Lys Glu Val Thr Lys Gln
                405                 410                 415

Leu Asn Asp Thr Thr Gly Lys Phe Lys Asp Val Ser His Leu Tyr Asp
        420                 425                 430

Val Lys Leu Thr Pro Lys Met Asn Val Thr Ile Lys Leu Ser Ile Leu
        435                 440                 445

Tyr Asp Asn Ala Glu Ser Asn Asp Asn Ser Ile Gly Lys Trp Thr Asn
        450                 455                 460

Thr Asn Ile Val Ser Gly Gly Asn Gly Lys Lys Gln Tyr Ser Ser
465                 470                 475                 480

Asn Asn Pro Asp Ala Asn Leu Thr Leu Asn Thr Asp Ala Gln Glu Lys
                485                 490                 495

Leu Asn Lys Asn Arg Asp Tyr Tyr Ile Ser Leu Tyr Met Lys Ser Glu
                500                 505                 510

Lys Asn Thr Gln Cys Glu Ile Thr Ile Asp Gly Glu Ile Tyr Pro Ile
        515                 520                 525

Thr Thr Lys Thr Val Asn Val Asn Lys Asp Asn Tyr Lys Arg Leu Asp
        530                 535                 540

Ile Ile Ala His Asn Ile Lys Ser Asn Pro Ile Ser Ser Leu His Ile
545                 550                 555                 560

Lys Thr Asn Asp Glu Ile Thr Leu Phe Trp Asp Asp Ile Ser Ile Thr
                565                 570                 575

Asp Val Ala Ser Ile Lys Pro Glu Asn Leu Thr Asp Ser Glu Ile Lys
                580                 585                 590

Gln Ile Tyr Ser Arg Tyr Gly Ile Lys Leu Glu Asp Gly Ile Leu Ile
        595                 600                 605

Asp Lys Lys Gly Gly Ile His Tyr Gly Glu Phe Ile Asn Glu Ala Ser
        610                 615                 620

Phe Asn Ile Glu Pro Leu Gln Asn Tyr Val Thr Lys Tyr Glu Val Thr
625                 630                 635                 640

Tyr Ser Ser Glu Leu Gly Pro Asn Val Ser Asp Thr Leu Glu Ser Asp
                645                 650                 655

Lys Ile Tyr Lys Asp Gly Thr Ile Lys Phe Asp Phe Thr Lys Tyr Ser
                660                 665                 670

Lys Asn Glu Gln Gly Leu Phe Tyr Asp Ser Gly Leu Asn Trp Asp Phe
        675                 680                 685

Lys Ile Asn Ala Ile Thr Tyr Asp Gly Lys Glu Met Asn Val Phe His
```

690                 695                 700
Arg Tyr Asn Lys
705

<210> SEQ ID NO 30
<211> LENGTH: 735
<212> TYPE: PRT
<213> ORGANISM: Bacillus anthracis

<400> SEQUENCE: 30

Glu Val Lys Gln Glu Asn Arg Leu Leu Asn Glu Ser Glu Ser Ser Ser
 1               5                  10                  15

Gln Gly Leu Leu Gly Tyr Tyr Phe Ser Asp Leu Asn Phe Gln Ala Pro
            20                  25                  30

Met Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
 50                  55                  60

Trp Ser Gly Phe Ile Lys Val Lys Lys Ser Asp Glu Tyr Thr Phe Ala
 65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Gln Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
            355                 360                 365

Thr Gly Thr Ala Pro Ile Tyr Asn Val Leu Pro Thr Thr Ser Leu Val
        370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
            405                 410                 415

Ala Pro Ile Ala Leu Asn Ala Gln Asp Asp Phe Ser Ser Thr Pro Ile
            420                 425                 430

Thr Met Asn Tyr Asn Gln Phe Leu Glu Leu Glu Lys Thr Lys Gln Leu
            435                 440                 445

Arg Leu Asp Thr Asp Gln Val Tyr Gly Asn Ile Ala Thr Tyr Asn Phe
450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
            485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
            515                 520                 525

Ile Ala Phe Gly Phe Asn Glu Pro Asn Gly Asn Leu Gln Tyr Gln Gly
            530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Val Thr Asn Ile Tyr Thr
            565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
            595                 600                 605

Glu Ser Val Val Lys Glu Ala His Arg Glu Val Ile Asn Ser Ser Thr
610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
            645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
            675                 680                 685

Ile Ser Asn Pro Asn Tyr Lys Val Asn Val Tyr Ala Val Thr Lys Glu
            690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
            725                 730                 735

<210> SEQ ID NO 31
<211> LENGTH: 876
<212> TYPE: PRT
<213> ORGANISM: Clostridium difficile

<400> SEQUENCE: 31

```
Met Lys Ile Gln Met Arg Asn Lys Val Leu Ser Phe Leu Thr Leu
  1               5                  10                  15

Thr Ala Ile Val Ser Gln Ala Leu Val Tyr Pro Val Tyr Ala Gln Thr
             20                  25                  30

Ser Thr Ser Asn His Ser Asn Lys Lys Glu Ile Val Asn Glu Asp
         35                  40                  45

Ile Leu Pro Asn Asn Gly Leu Met Gly Tyr Tyr Phe Ser Asp Glu His
 50                      55                  60

Phe Lys Asp Leu Lys Leu Met Ala Pro Ile Lys Asp Gly Asn Leu Lys
 65                  70                  75                  80

Phe Glu Glu Lys Lys Val Asp Lys Leu Leu Asp Lys Asp Lys Ser Asp
                 85                  90                  95

Val Lys Ser Ile Arg Trp Thr Gly Arg Ile Ile Pro Ser Lys Asp Gly
                100                 105                 110

Glu Tyr Thr Leu Ser Thr Asp Arg Asp Asp Val Leu Met Gln Val Asn
             115                 120                 125

Thr Glu Ser Thr Ile Ser Asn Thr Leu Lys Val Asn Met Lys Lys Gly
130                 135                 140

Lys Glu Tyr Lys Val Arg Ile Glu Leu Gln Asp Lys Asn Leu Gly Ser
145                 150                 155                 160

Ile Asp Asn Leu Ser Ser Pro Asn Leu Tyr Trp Glu Leu Asp Gly Met
                165                 170                 175

Lys Lys Ile Ile Pro Glu Glu Asn Leu Phe Leu Arg Asp Tyr Ser Asn
             180                 185                 190

Ile Glu Lys Asp Asp Pro Phe Ile Pro Asn Asn Phe Phe Asp Pro
         195                 200                 205

Lys Leu Met Ser Asp Trp Glu Asp Glu Asp Leu Asp Thr Asp Asn Asp
     210                 215                 220

Asn Ile Pro Asp Ser Tyr Glu Arg Asn Gly Tyr Thr Ile Lys Asp Leu
225                 230                 235                 240

Ile Ala Val Lys Trp Glu Asp Ser Phe Ala Glu Gln Gly Tyr Lys Lys
                245                 250                 255

Tyr Val Ser Asn Tyr Leu Glu Ser Asn Thr Ala Gly Asp Pro Tyr Thr
             260                 265                 270

Asp Tyr Glu Lys Ala Ser Gly Ser Phe Asp Lys Ala Ile Lys Thr Glu
         275                 280                 285

Ala Arg Asp Pro Leu Val Ala Ala Tyr Pro Ile Val Gly Val Gly Met
     290                 295                 300

Glu Lys Leu Ile Ile Ser Thr Asn Glu His Ala Ser Thr Asp Gln Gly
305                 310                 315                 320

Lys Thr Val Ser Arg Ala Thr Thr Asn Ser Lys Thr Glu Ser Asn Thr
                325                 330                 335

Ala Gly Val Ser Val Asn Val Gly Tyr Gln Asn Gly Phe Thr Ala Asn
             340                 345                 350

Val Thr Thr Asn Tyr Ser His Thr Thr Asp Asn Ser Thr Ala Val Gln
         355                 360                 365

Asp Ser Asn Gly Glu Ser Trp Asn Thr Gly Leu Ser Ile Asn Lys Gly
     370                 375                 380

Glu Ser Ala Tyr Ile Asn Ala Asn Val Arg Tyr Tyr Asn Thr Gly Thr
385                 390                 395                 400

Ala Pro Met Tyr Lys Val Thr Pro Thr Thr Asn Leu Val Leu Asp Gly
                405                 410                 415
```

-continued

```
Asp Thr Leu Ser Thr Ile Lys Ala Gln Glu Asn Gln Ile Gly Asn Asn
            420                 425                 430
Leu Ser Pro Gly Asp Thr Tyr Pro Lys Lys Gly Leu Ser Pro Leu Ala
        435                 440                 445
Leu Asn Thr Met Asp Gln Phe Ser Ser Arg Leu Ile Pro Ile Asn Tyr
    450                 455                 460
Asp Gln Leu Lys Lys Leu Asp Ala Gly Lys Gln Ile Lys Leu Glu Thr
465                 470                 475                 480
Thr Gln Val Ser Gly Asn Phe Gly Thr Lys Asn Ser Ser Gly Gln Ile
            485                 490                 495
Val Thr Glu Gly Asn Ser Trp Ser Asp Tyr Ile Ser Gln Ile Asp Ser
        500                 505                 510
Ile Ser Ala Ser Ile Ile Leu Asp Thr Glu Asn Glu Ser Tyr Glu Arg
    515                 520                 525
Arg Val Thr Ala Lys Asn Leu Gln Asp Pro Glu Asp Lys Thr Pro Glu
530                 535                 540
Leu Thr Ile Gly Glu Ala Ile Glu Lys Ala Phe Gly Ala Thr Lys Lys
545                 550                 555                 560
Asp Gly Leu Leu Tyr Phe Asn Asp Ile Pro Ile Asp Glu Ser Cys Val
            565                 570                 575
Glu Leu Ile Phe Asp Asp Asn Thr Ala Asn Lys Ile Lys Asp Ser Leu
        580                 585                 590
Lys Thr Leu Ser Asp Lys Lys Ile Tyr Asn Val Lys Leu Glu Arg Gly
    595                 600                 605
Met Asn Ile Leu Ile Lys Thr Pro Thr Tyr Phe Thr Asn Phe Asp Asp
            610                 615                 620
Tyr Asn Asn Tyr Pro Ser Thr Trp Ser Asn Val Asn Thr Thr Asn Gln
625                 630                 635                 640
Asp Gly Leu Gln Gly Ser Ala Asn Lys Leu Asn Gly Glu Thr Lys Ile
            645                 650                 655
Lys Ile Pro Met Ser Glu Leu Lys Pro Tyr Lys Arg Tyr Val Phe Ser
        660                 665                 670
Gly Tyr Ser Lys Asp Pro Leu Thr Ser Asn Ser Ile Ile Val Lys Ile
    675                 680                 685
Lys Ala Lys Glu Glu Lys Thr Asp Tyr Leu Val Pro Glu Gln Gly Tyr
690                 695                 700
Thr Lys Phe Ser Tyr Glu Phe Glu Thr Thr Glu Lys Asp Ser Ser Asn
705                 710                 715                 720
Ile Glu Ile Thr Leu Ile Gly Ser Gly Thr Thr Tyr Leu Asp Asn Leu
            725                 730                 735
Ser Ile Thr Glu Leu Asn Ser Thr Pro Glu Ile Leu Asp Glu Pro Glu
        740                 745                 750
Val Lys Ile Pro Thr Asp Gln Glu Ile Met Asp Ala His Lys Ile Tyr
    755                 760                 765
Phe Ala Asp Leu Asn Phe Asn Pro Ser Thr Gly Asn Thr Tyr Ile Asn
770                 775                 780
Gly Met Tyr Phe Ala Pro Thr Gln Thr Asn Lys Glu Ala Leu Asp Tyr
785                 790                 795                 800
Ile Gln Lys Tyr Arg Val Glu Ala Thr Leu Gln Tyr Ser Gly Phe Lys
            805                 810                 815
Asp Ile Gly Thr Lys Asp Lys Glu Met Arg Asn Tyr Leu Gly Asp Pro
        820                 825                 830
Asn Gln Pro Lys Thr Asn Tyr Val Asn Leu Arg Ser Tyr Phe Thr Gly
```

```
                    835                 840                 845
Gly Glu Asn Ile Met Thr Tyr Lys Lys Leu Arg Ile Tyr Ala Ile Thr
    850                 855                 860

Pro Asp Asp Arg Glu Leu Leu Val Leu Ser Val Asp
865                 870                 875

<210> SEQ ID NO 32
<211> LENGTH: 875
<212> TYPE: PRT
<213> ORGANISM: Clostridium perfringens

<400> SEQUENCE: 32

Met Asn Ile Gln Ile Lys Asn Val Phe Ser Phe Leu Thr Leu Thr Ala
1               5                   10                  15

Met Ile Ser Gln Thr Leu Ser Tyr Asn Val Tyr Ala Gln Thr Thr Thr
                20                  25                  30

Gln Asn Asp Thr Asn Gln Lys Glu Glu Ile Thr Asn Glu Asn Thr Leu
            35                  40                  45

Ser Ser Asn Gly Leu Met Gly Tyr Tyr Phe Ala Asp Glu His Phe Lys
    50                  55                  60

Asp Leu Glu Leu Met Ala Pro Ile Lys Asn Gly Asp Leu Lys Phe Glu
65                  70                  75                  80

Glu Lys Lys Val Asp Lys Leu Leu Thr Glu Asp Asn Ser Ser Ile Lys
                85                  90                  95

Ser Ile Arg Trp Thr Gly Arg Ile Ile Pro Ser Glu Asp Gly Glu Tyr
            100                 105                 110

Ile Leu Ser Thr Asp Arg Asn Asp Val Leu Met Gln Ile Asn Ala Lys
        115                 120                 125

Gly Asp Ile Ala Lys Thr Leu Lys Val Asn Met Lys Lys Gly Gln Ala
    130                 135                 140

Tyr Asn Ile Arg Ile Glu Ile Gln Asp Lys Asn Leu Gly Ser Ile Asp
145                 150                 155                 160

Asn Leu Ser Val Pro Lys Leu Tyr Trp Glu Leu Asn Gly Asn Lys Thr
                165                 170                 175

Val Ile Pro Glu Glu Asn Leu Phe Phe Arg Asp Tyr Ser Lys Ile Asp
            180                 185                 190

Glu Asn Asp Pro Phe Ile Pro Asn Asn Phe Phe Asp Val Arg Phe
        195                 200                 205

Phe Ser Ala Ala Trp Glu Asp Glu Asp Leu Asp Thr Asp Asn Asp Asn
    210                 215                 220

Ile Pro Asp Ala Tyr Glu Lys Asn Gly Tyr Thr Ile Lys Asp Ser Ile
225                 230                 235                 240

Ala Val Lys Trp Asn Asp Ser Phe Ala Glu Gln Gly Tyr Lys Lys Tyr
                245                 250                 255

Val Ser Ser Tyr Leu Glu Ser Asn Thr Ala Gly Asp Pro Tyr Thr Asp
            260                 265                 270

Tyr Gln Lys Ala Ser Gly Ser Ile Asp Lys Ala Ile Lys Leu Glu Ala
        275                 280                 285

Arg Asp Pro Leu Val Ala Ala Tyr Pro Val Val Gly Val Gly Met Glu
    290                 295                 300

Asn Leu Ile Ile Ser Thr Asn Glu His Ala Ser Ser Asp Gln Gly Lys
305                 310                 315                 320

Thr Val Ser Arg Ala Thr Thr Asn Ser Lys Thr Asp Ala Asn Thr Val
                325                 330                 335
```

```
Gly Val Ser Ile Ser Ala Gly Tyr Gln Asn Gly Phe Thr Gly Asn Ile
                340                 345                 350

Thr Thr Ser Tyr Ser His Thr Asp Asn Ser Thr Ala Val Gln Asp
            355                 360                 365

Ser Asn Gly Glu Ser Trp Asn Thr Gly Leu Ser Ile Asn Lys Gly Glu
        370                 375                 380

Ser Ala Tyr Ile Asn Ala Asn Val Arg Tyr Tyr Asn Thr Gly Thr Ala
385                 390                 395                 400

Pro Met Tyr Lys Val Thr Pro Thr Thr Asn Leu Val Leu Asp Gly Glu
                405                 410                 415

Thr Leu Ala Thr Ile Lys Ala Gln Asp Asn Gln Ile Gly Asn Asn Leu
                420                 425                 430

Ser Pro Asn Glu Thr Tyr Pro Lys Lys Gly Leu Ser Pro Leu Ala Leu
        435                 440                 445

Asn Thr Met Asp Gln Phe Asn Ala Arg Leu Ile Pro Ile Asn Tyr Asp
    450                 455                 460

Gln Leu Lys Lys Leu Asp Ser Gly Lys Gln Ile Lys Leu Glu Thr Thr
465                 470                 475                 480

Gln Val Ser Gly Asn Tyr Gly Thr Lys Asn Ser Gln Gly Gln Ile Ile
                485                 490                 495

Thr Glu Gly Asn Ser Trp Ser Asn Tyr Ile Ser Gln Ile Asp Ser Val
            500                 505                 510

Ser Ala Ser Ile Ile Leu Asp Thr Gly Ser Gln Thr Phe Glu Arg Arg
        515                 520                 525

Val Ala Ala Lys Glu Gln Gly Asn Pro Glu Asp Lys Thr Pro Glu Ile
    530                 535                 540

Thr Ile Gly Glu Ala Ile Lys Lys Ala Phe Ser Ala Thr Lys Asn Gly
545                 550                 555                 560

Glu Leu Leu Tyr Phe Asn Gly Ile Pro Ile Asp Glu Ser Cys Val Glu
                565                 570                 575

Leu Ile Phe Asp Asp Asn Thr Ser Glu Ile Ile Lys Glu Gln Leu Lys
            580                 585                 590

Tyr Leu Asp Asp Lys Lys Ile Tyr Asn Val Lys Leu Glu Arg Gly Met
        595                 600                 605

Asn Ile Leu Ile Lys Val Pro Ser Tyr Phe Thr Asn Phe Asp Glu Tyr
    610                 615                 620

Asn Asn Phe Pro Ala Ser Trp Ser Asn Ile Asp Thr Lys Asn Gln Asp
625                 630                 635                 640

Gly Leu Gln Ser Val Ala Asn Lys Leu Ser Gly Glu Thr Lys Ile Ile
                645                 650                 655

Ile Pro Met Ser Lys Leu Lys Pro Tyr Lys Arg Tyr Val Phe Ser Gly
            660                 665                 670

Tyr Ser Lys Asp Pro Ser Thr Ser Asn Ser Ile Thr Val Asn Ile Lys
        675                 680                 685

Ser Lys Glu Gln Lys Thr Asp Tyr Leu Val Pro Glu Lys Asp Tyr Thr
    690                 695                 700

Lys Phe Ser Tyr Glu Phe Glu Thr Thr Gly Lys Asp Ser Ser Asp Ile
705                 710                 715                 720

Glu Ile Thr Leu Thr Ser Ser Gly Val Ile Phe Leu Asp Asn Leu Ser
                725                 730                 735

Ile Thr Glu Leu Asn Ser Thr Pro Glu Ile Leu Lys Glu Pro Glu Ile
            740                 745                 750

Lys Val Pro Ser Asp Gln Glu Ile Leu Asp Ala His Asn Lys Tyr Tyr
```

-continued

```
        755                 760                 765

Ala Asp Ile Lys Leu Asp Thr Asn Thr Gly Asn Thr Tyr Ile Asp Gly
    770                 775                 780

Ile Tyr Phe Glu Pro Thr Gln Thr Asn Lys Glu Ala Leu Asp Tyr Ile
785                 790                 795                 800

Gln Lys Tyr Arg Val Glu Ala Thr Leu Gln Tyr Ser Gly Phe Lys Asp
                805                 810                 815

Ile Gly Thr Lys Asp Lys Glu Ile Arg Asn Tyr Leu Gly Asp Gln Asn
            820                 825                 830

Gln Pro Lys Thr Asn Tyr Ile Asn Phe Arg Ser Tyr Phe Thr Ser Gly
        835                 840                 845

Glu Asn Val Met Thr Tyr Lys Lys Leu Arg Ile Tyr Ala Val Thr Pro
    850                 855                 860

Asp Asn Arg Glu Leu Leu Val Leu Ser Val Asn
865                 870                 875

<210> SEQ ID NO 33
<211> LENGTH: 879
<212> TYPE: PRT
<213> ORGANISM: Clostridium spiroforme

<400> SEQUENCE: 33

Met Lys Asn Lys Lys Ile Leu Gly Leu Leu Thr Cys Thr Val Leu Val
 1               5                  10                  15

Gly Gln Met Met Thr Tyr Pro Val Tyr Ala Lys Thr Ile Thr Gln Asn
            20                  25                  30

Tyr Asp Asn Gln Glu Val Glu Thr Thr Asn Glu Lys Thr Val Ser Ser
        35                  40                  45

Asn Gly Leu Met Gly Tyr Tyr Phe Ala Asp Glu His Phe Lys Asp Leu
    50                  55                  60

Glu Leu Met Ala Pro Val Lys Asn Gly Glu Leu Lys Phe Glu Lys Asn
65                  70                  75                  80

Lys Val Glu Lys Leu Leu Thr Glu Glu Lys Thr Asn Ile Lys Ser Ile
                85                  90                  95

Arg Trp Thr Gly Arg Ile Ile Pro Ser Lys Asp Gly Glu Tyr Thr Leu
            100                 105                 110

Ser Thr Asp Lys Asp Asn Val Leu Met Gln Ile Asn Ala Glu Gly Glu
        115                 120                 125

Ile Ala Asn Thr Leu Lys Val Asn Met Ile Lys Gly Gln Glu Tyr Ser
    130                 135                 140

Ile Arg Ile Glu Ile Gln Asp Lys Asp Ile Gly Tyr Val Asp Asp Leu
145                 150                 155                 160

Ser Ser Pro Lys Leu Tyr Trp Glu Leu Asn Gly Asp Lys Thr Leu Ile
                165                 170                 175

Pro Glu Lys Asn Leu Phe Leu Arg Asp Tyr Ser Lys Ile Asp Glu Asn
            180                 185                 190

Asp Pro Phe Ile Pro Lys Asp Asn Phe Phe Asp Leu Lys Leu Lys Ser
        195                 200                 205

Arg Ser Ala Arg Leu Ala Ser Gly Trp Gly Asp Glu Asp Leu Asp Thr
    210                 215                 220

Asp Asn Asp Asn Ile Pro Asp Ala Tyr Glu Lys Asn Gly Tyr Thr Ile
225                 230                 235                 240

Lys Asp Ser Ile Ala Val Lys Trp Glu Asp Ser Phe Ala Gln Gln Gly
                245                 250                 255
```

-continued

```
Tyr Lys Lys Tyr Leu Ser Ser Tyr Leu Glu Ser Asn Thr Ala Gly Asp
            260                 265                 270
Pro Tyr Thr Asp Tyr Gln Lys Ala Ser Gly Ser Phe Asp Lys Ala Ile
        275                 280                 285
Lys Ala Glu Ala Arg Asp Pro Leu Val Ala Ala Tyr Pro Val Val Gly
290                 295                 300
Val Gly Met Glu Lys Leu Ile Ile Ser Thr Asn Glu His Ala Ser Thr
305                 310                 315                 320
Asp Gln Gly Lys Thr Val Ser Arg Asn Thr Thr Asn Ser Lys Thr Asp
            325                 330                 335
Ala Asn Thr Ala Gly Val Ala Ile Asn Ile Ala Tyr Gln Asn Gly Phe
            340                 345                 350
Thr Gly Ser Ile Thr Thr Asn Tyr Ser His Thr Thr Glu Asn Ser Thr
            355                 360                 365
Ala Val Gln Asn Ser Asn Gly Glu Ser Trp Asn Thr Ser Leu Ser Ile
        370                 375                 380
Asn Lys Gly Glu Ser Ala Tyr Ile Asn Ala Asn Val Arg Tyr Tyr Asn
385                 390                 395                 400
Thr Gly Thr Ala Pro Met Tyr Lys Val Thr Pro Thr Thr Asn Leu Val
            405                 410                 415
Leu Asp Gly Asp Thr Leu Thr Thr Ile Lys Ala Gln Asp Asn Gln Ile
            420                 425                 430
Gly Asn Asn Leu Ser Pro Asn Glu Thr Tyr Pro Lys Lys Gly Leu Ser
            435                 440                 445
Pro Leu Ala Leu Asn Thr Met Asp Gln Phe Ser Ser Arg Leu Ile Pro
        450                 455                 460
Ile Asn Tyr Asp Gln Leu Lys Lys Leu Asp Ala Gly Lys Gln Ile Lys
465                 470                 475                 480
Leu Glu Thr Thr Gln Val Ser Gly Asn Tyr Gly Ile Lys Asn Ser Gln
            485                 490                 495
Gly Gln Ile Ile Thr Glu Gly Asn Ser Trp Ser Asp Tyr Ile Ser Gln
            500                 505                 510
Ile Asp Ser Leu Ser Ala Ser Ile Ile Leu Asp Thr Gly Ser Asp Val
        515                 520                 525
Phe Glu Arg Arg Val Thr Ala Lys Asp Ser Ser Asn Pro Glu Asp Lys
530                 535                 540
Thr Pro Val Leu Thr Ile Gly Glu Ala Ile Glu Lys Ala Phe Gly Ala
545                 550                 555                 560
Thr Lys Asn Gly Glu Ile Leu Tyr Phe Asn Gly Met Pro Ile Asp Glu
            565                 570                 575
Ser Cys Val Glu Leu Ile Phe Asp Gly Asn Thr Ala Asn Leu Ile Lys
            580                 585                 590
Glu Arg Leu Asn Ala Leu Asn Asp Lys Lys Ile Tyr Asn Val Gln Leu
        595                 600                 605
Glu Arg Gly Met Lys Ile Leu Ile Lys Thr Ser Thr Tyr Phe Asn Asn
        610                 615                 620
Phe Asp Gly Tyr Asn Asn Phe Pro Ser Ser Trp Ser Asn Val Asp Ser
625                 630                 635                 640
Asn Asn Gln Asp Gly Leu Gln Asn Ala Ala Asn Lys Leu Ser Gly Glu
            645                 650                 655
Thr Lys Ile Val Ile Pro Met Ser Lys Leu Asn Pro Tyr Lys Arg Tyr
            660                 665                 670
Val Phe Ser Gly Tyr Leu Lys Asn Ser Ser Thr Ser Asn Pro Ile Thr
```

```
                675                 680                 685
Val Asn Ile Lys Ala Lys Glu Gln Lys Thr Tyr Asn Leu Val Ser Glu
    690                 695                 700

Asn Asp Tyr Lys Lys Phe Ser Tyr Glu Phe Glu Thr Ile Gly Arg Asp
705                 710                 715                 720

Ala Ser Asn Ile Glu Ile Thr Leu Thr Ser Ser Gly Thr Ile Phe Leu
                725                 730                 735

Asp Asn Leu Ser Ile Thr Glu Leu Asn Ser Thr Pro Glu Ile Leu Lys
                740                 745                 750

Glu Pro Asp Ile Lys Val Pro Ser Asp Gln Glu Ile Ile Asp Ala His
            755                 760                 765

Lys Lys Tyr Tyr Ala Asp Leu Ser Phe Asn Gln Ser Thr Ala Asn Tyr
    770                 775                 780

Tyr Leu Asp Gly Leu Tyr Phe Glu Pro Thr Gln Thr Asn Lys Glu Val
785                 790                 795                 800

Leu Asp Tyr Ile Gln Lys Tyr Lys Val Glu Ala Thr Leu Glu Tyr Ser
                805                 810                 815

Gly Phe Lys Asp Ile Gly Thr Lys Asp Lys Glu Leu Arg Asn Tyr Thr
            820                 825                 830

Gly Asp Ser Asn Gln Pro Lys Thr Asn Tyr Val Asn Phe Arg Ser Tyr
        835                 840                 845

Phe Thr Ser Gly Glu Asn Val Met Pro Tyr Lys Lys Leu Arg Ile Tyr
850                 855                 860

Ala Ile Thr Pro Glu Asn Lys Glu Leu Leu Val Leu Ser Ile Asn
865                 870                 875

<210> SEQ ID NO 34
<211> LENGTH: 721
<212> TYPE: PRT
<213> ORGANISM: Clostridium botulinum

<400> SEQUENCE: 34

Met Leu Val Ser Lys Phe Glu Asn Ser Val Lys Asn Ser Asn Lys Asn
1               5                   10                  15

Tyr Phe Thr Ile Asn Gly Leu Met Gly Tyr Tyr Phe Glu Asn Asp Phe
                20                  25                  30

Phe Asn Leu Asn Ile Ile Ser Pro Thr Leu Asp Gly Asn Leu Thr Phe
            35                  40                  45

Ser Lys Glu Asp Ile Asn Ser Ile Leu Gly Asn Lys Ile Ile Lys Ser
50                  55                  60

Ala Arg Trp Ile Gly Leu Ile Lys Pro Ser Ile Thr Gly Glu Tyr Ile
65                  70                  75                  80

Leu Ser Thr Asn Ser Pro Asn Cys Arg Val Glu Leu Asn Gly Glu Ile
                85                  90                  95

Phe Asn Leu Ser Leu Asn Thr Ser Asn Thr Val Asn Leu Ile Gln Gly
            100                 105                 110

Asn Val Tyr Asp Ile Arg Ile Glu Gln Leu Met Ser Glu Asn Gln Leu
        115                 120                 125

Leu Lys Asn Tyr Glu Gly Ile Lys Leu Tyr Trp Glu Thr Ser Asp Ile
    130                 135                 140

Ile Lys Glu Ile Ile Pro Ser Glu Val Leu Leu Lys Pro Asn Tyr Ser
145                 150                 155                 160

Asn Thr Asn Glu Lys Ser Lys Phe Ile Pro Asn Asn Thr Leu Phe Ser
                165                 170                 175
```

```
Asn Ala Lys Leu Lys Ala Asn Ala Asn Arg Asp Thr Asp Arg Asp Gly
            180                 185                 190
Ile Pro Asp Glu Trp Glu Ile Asn Gly Tyr Thr Val Met Asn Gln Lys
            195                 200                 205
Ala Val Ala Trp Asp Asp Lys Phe Ala Ala Asn Gly Tyr Lys Lys Tyr
            210                 215                 220
Val Ser Asn Pro Phe Lys Pro Cys Thr Ala Asn Asp Pro Tyr Thr Asp
225                 230                 235                 240
Phe Glu Lys Val Ser Gly Gln Ile Asp Pro Ser Val Ser Met Val Ala
                245                 250                 255
Arg Asp Pro Met Ile Ser Ala Tyr Pro Ile Val Gly Val Gln Met Glu
                260                 265                 270
Arg Leu Val Val Ser Lys Ser Glu Thr Ile Thr Gly Asp Ser Thr Lys
            275                 280                 285
Ser Met Ser Lys Ser Thr Ser His Ser Ser Thr Asn Ile Asn Thr Val
            290                 295                 300
Gly Ala Glu Val Ser Gly Ser Leu Gln Leu Ala Gly Gly Ile Phe Pro
305                 310                 315                 320
Val Phe Ser Met Ser Ala Ser Ala Asn Tyr Ser His Thr Trp Gln Asn
                325                 330                 335
Thr Ser Thr Val Asp Asp Thr Thr Gly Glu Ser Phe Ser Gln Gly Leu
            340                 345                 350
Ser Ile Asn Thr Gly Glu Ser Ala Tyr Ile Asn Pro Asn Ile Arg Tyr
            355                 360                 365
Tyr Asn Thr Gly Thr Ala Pro Val Tyr Asn Val Thr Pro Thr Thr Thr
            370                 375                 380
Ile Val Ile Asp Lys Gln Ser Val Ala Thr Ile Lys Gly Gln Glu Ser
385                 390                 395                 400
Leu Ile Gly Asp Tyr Leu Asn Pro Gly Gly Thr Tyr Pro Ile Ile Gly
                405                 410                 415
Glu Pro Pro Met Ala Leu Asn Thr Met Asp Gln Phe Ser Ser Arg Leu
                420                 425                 430
Ile Pro Ile Asn Tyr Asn Gln Leu Lys Ser Ile Asp Asn Gly Gly Thr
            435                 440                 445
Val Met Leu Ser Thr Ser Gln Phe Thr Gly Asn Phe Ala Lys Tyr Asn
450                 455                 460
Ser Asn Gly Asn Leu Val Thr Asp Gly Asn Asn Trp Gly Pro Tyr Leu
465                 470                 475                 480
Gly Thr Ile Lys Ser Thr Thr Ala Ser Leu Thr Leu Ser Phe Ser Gly
                485                 490                 495
Gln Thr Thr Gln Val Ala Val Val Ala Pro Asn Phe Ser Asp Pro Glu
                500                 505                 510
Asp Lys Thr Pro Lys Leu Thr Leu Glu Gln Ala Leu Val Lys Ala Phe
            515                 520                 525
Ala Leu Glu Lys Lys Asn Gly Lys Phe Tyr Phe His Gly Leu Glu Ile
            530                 535                 540
Ser Lys Asn Glu Lys Ile Gln Val Phe Leu Asp Ser Asn Thr Asn Asn
545                 550                 555                 560
Asp Phe Glu Asn Gln Leu Lys Asn Thr Ala Asp Lys Asp Ile Met His
                565                 570                 575
Cys Ile Ile Lys Arg Asn Met Asn Ile Leu Val Lys Val Ile Thr Phe
            580                 585                 590
Lys Glu Asn Ile Ser Ser Ile Asn Ile Ile Asn Asp Thr Asn Phe Gly
```

-continued

```
        595                 600                 605

Val Gln Ser Met Thr Gly Leu Ser Asn Arg Ser Lys Gly Gln Asp Gly
    610                 615                 620

Ile Tyr Arg Ala Ala Thr Thr Ala Phe Ser Phe Lys Ser Lys Glu Leu
625                 630                 635                 640

Lys Tyr Pro Glu Gly Arg Tyr Arg Met Arg Phe Val Ile Gln Ser Tyr
                645                 650                 655

Glu Pro Phe Thr Cys Asn Phe Lys Leu Phe Asn Asn Leu Ile Tyr Ser
            660                 665                 670

Ser Ser Phe Asp Lys Gly Tyr Tyr Asp Glu Phe Phe Tyr Phe Tyr Tyr
        675                 680                 685

Asn Gly Ser Lys Ser Phe Phe Asn Ile Ser Cys Asp Ile Ile Asn Ser
    690                 695                 700

Ile Asn Arg Leu Ser Gly Val Phe Leu Ile Glu Leu Asp Lys Leu Ile
705                 710                 715                 720

Ile

<210> SEQ ID NO 35
<211> LENGTH: 1338
<212> TYPE: PRT
<213> ORGANISM: Bacillus cereus

<400> SEQUENCE: 35

Met Lys Arg Met Glu Gly Lys Leu Phe Met Val Ser Lys Lys Leu Gln
 1               5                  10                  15

Val Val Thr Lys Thr Val Leu Leu Ser Thr Val Phe Ser Ile Ser Leu
            20                  25                  30

Leu Asn Asn Glu Val Ile Lys Ala Glu Gln Leu Asn Ile Asn Ser Gln
        35                  40                  45

Ser Lys Tyr Thr Asn Leu Gln Asn Leu Lys Ile Thr Asp Lys Val Glu
    50                  55                  60

Asp Phe Lys Glu Asp Lys Glu Lys Ala Lys Glu Trp Gly Lys Glu Lys
65                  70                  75                  80

Glu Lys Glu Trp Lys Leu Thr Ala Thr Glu Lys Gly Lys Met Asn Asn
                85                  90                  95

Phe Leu Asp Asn Lys Asn Asp Ile Lys Thr Asn Tyr Lys Glu Ile Thr
            100                 105                 110

Phe Ser Ile Ala Gly Ser Phe Glu Asp Glu Ile Lys Asp Leu Lys Glu
        115                 120                 125

Ile Asp Lys Met Phe Asp Lys Thr Asn Leu Ser Asn Ser Ile Ile Thr
    130                 135                 140

Tyr Lys Asn Val Glu Pro Thr Thr Ile Gly Phe Asn Lys Ser Leu Thr
145                 150                 155                 160

Glu Gly Asn Thr Ile Asn Ser Asp Ala Met Ala Gln Phe Lys Glu Gln
                165                 170                 175

Phe Leu Asp Arg Asp Ile Lys Phe Asp Ser Tyr Leu Asp Thr His Leu
            180                 185                 190

Thr Ala Gln Gln Val Ser Ser Lys Glu Arg Val Ile Leu Lys Val Thr
        195                 200                 205

Val Pro Ser Gly Lys Gly Ser Thr Thr Pro Thr Lys Ala Gly Val Ile
    210                 215                 220

Leu Asn Asn Ser Glu Tyr Lys Met Leu Ile Asp Asn Gly Tyr Met Val
225                 230                 235                 240

His Val Asp Lys Val Ser Lys Val Val Lys Lys Gly Val Glu Cys Leu
```

-continued

```
                245                 250                 255
Gln Ile Glu Gly Thr Leu Lys Lys Ser Leu Asp Phe Lys Asn Asp Ile
            260                 265                 270

Asn Ala Glu Ala His Ser Trp Gly Met Lys Asn Tyr Glu Glu Trp Ala
            275                 280                 285

Lys Asp Leu Thr Asp Ser Gln Arg Glu Ala Leu Asp Gly Tyr Ala Arg
            290                 295                 300

Gln Asp Tyr Lys Glu Ile Asn Asn Tyr Leu Arg Asn Gln Gly Gly Ser
305                 310                 315                 320

Gly Asn Glu Lys Leu Asp Ala Gln Ile Lys Asn Ile Ser Asp Ala Leu
                325                 330                 335

Gly Lys Lys Pro Ile Pro Glu Asn Ile Thr Val Tyr Arg Trp Cys Gly
                340                 345                 350

Met Pro Glu Phe Gly Tyr Gln Ile Ser Asp Pro Leu Pro Ser Leu Lys
            355                 360                 365

Asp Phe Glu Glu Gln Phe Leu Asn Thr Ile Lys Glu Asp Lys Gly Tyr
            370                 375                 380

Met Ser Thr Ser Leu Ser Ser Glu Arg Leu Ala Ala Phe Gly Ser Arg
385                 390                 395                 400

Lys Ile Ile Leu Arg Leu Gln Val Pro Lys Gly Ser Thr Gly Ala Tyr
                405                 410                 415

Leu Ser Ala Ile Gly Gly Phe Ala Ser Glu Lys Glu Ile Leu Leu Asp
                420                 425                 430

Lys Asp Ser Lys Tyr His Ile Asp Lys Val Thr Glu Val Ile Ile Lys
            435                 440                 445

Gly Val Lys Arg Tyr Val Val Asp Ala Thr Leu Leu Thr Asn Ser Arg
450                 455                 460

Gly Pro Ser Thr Pro Pro Thr Pro Ser Pro Ser Thr Pro Pro Thr Pro
465                 470                 475                 480

Ser Asp Ile Gly Ser Thr Met Lys Thr Asn Gln Ile Ser Thr Thr Gln
                485                 490                 495

Lys Asn Gln Gln Lys Glu Met Asp Arg Lys Gly Leu Leu Gly Tyr Tyr
            500                 505                 510

Phe Lys Gly Lys Asp Phe Ser Asn Leu Thr Met Phe Ala Pro Thr Arg
            515                 520                 525

Asp Ser Thr Leu Ile Tyr Asp Gln Gln Thr Ala Asn Lys Leu Leu Asp
            530                 535                 540

Lys Lys Gln Gln Glu Tyr Gln Ser Ile Arg Trp Ile Gly Leu Ile Gln
545                 550                 555                 560

Ser Lys Glu Thr Gly Asp Phe Thr Phe Asn Leu Ser Glu Asp Glu Gln
                565                 570                 575

Ala Ile Ile Glu Ile Asn Gly Lys Ile Ile Ser Asn Lys Gly Lys Glu
                580                 585                 590

Lys Gln Val Val His Leu Glu Lys Gly Lys Leu Val Pro Ile Lys Ile
            595                 600                 605

Glu Tyr Gln Ser Asp Thr Lys Phe Asn Ile Asp Ser Lys Thr Phe Lys
            610                 615                 620

Glu Leu Lys Leu Phe Lys Ile Asp Ser Gln Asn Gln Pro Gln Gln Val
625                 630                 635                 640

Gln Gln Asp Glu Leu Arg Asn Pro Glu Phe Asn Lys Lys Glu Ser Gln
                645                 650                 655

Glu Phe Leu Ala Lys Pro Ser Lys Ile Asn Leu Phe Thr Gln Gln Met
                660                 665                 670
```

```
Lys Arg Glu Ile Asp Glu Asp Thr Asp Thr Asp Gly Asp Ser Ile Pro
            675                 680                 685

Asp Leu Trp Glu Glu Asn Gly Tyr Thr Ile Gln Asn Arg Ile Ala Val
        690                 695                 700

Lys Trp Asp Asp Ser Leu Ala Ser Lys Gly Tyr Thr Lys Phe Val Ser
705                 710                 715                 720

Asn Pro Leu Glu Ser His Thr Val Gly Asp Pro Tyr Thr Asp Tyr Glu
                725                 730                 735

Lys Ala Ala Arg Asp Leu Asp Leu Ser Asn Ala Lys Glu Thr Phe Asn
            740                 745                 750

Pro Leu Val Ala Ala Phe Pro Ser Val Asn Val Ser Met Glu Lys Val
        755                 760                 765

Ile Leu Ser Pro Asn Glu Asn Leu Ser Asn Ser Val Glu Ser His Ser
    770                 775                 780

Ser Thr Asn Trp Ser Tyr Thr Asn Thr Glu Gly Ala Ser Val Glu Ala
785                 790                 795                 800

Gly Ile Gly Pro Lys Gly Ile Ser Phe Gly Val Ser Val Asn Tyr Gln
                805                 810                 815

His Ser Glu Thr Val Ala Gln Glu Trp Gly Thr Ser Thr Gly Asn Thr
            820                 825                 830

Ser Gln Phe Asn Thr Ala Ser Ala Gly Tyr Leu Asn Ala Asn Val Arg
        835                 840                 845

Tyr Asn Asn Val Gly Thr Gly Ala Ile Tyr Asp Val Lys Pro Thr Thr
    850                 855                 860

Ser Phe Val Leu Asn Asn Asp Thr Ile Ala Thr Ile Thr Ala Lys Ser
865                 870                 875                 880

Asn Ser Thr Ala Leu Asn Ile Ser Pro Gly Glu Ser Tyr Pro Lys Lys
                885                 890                 895

Gly Gln Asn Gly Ile Ala Ile Thr Ser Met Asp Asp Phe Asn Ser His
            900                 905                 910

Pro Ile Thr Leu Asn Lys Lys Gln Val Asp Asn Leu Leu Asn Asn Lys
        915                 920                 925

Pro Met Met Leu Glu Thr Asn Gln Thr Asp Gly Val Tyr Lys Ile Lys
    930                 935                 940

Asp Thr His Gly Asn Ile Val Thr Gly Gly Glu Trp Asn Gly Val Ile
945                 950                 955                 960

Gln Gln Ile Lys Ala Lys Thr Ala Ser Ile Ile Val Asp Asp Gly Glu
                965                 970                 975

Arg Val Ala Glu Lys Arg Val Ala Ala Lys Asp Tyr Glu Asn Pro Glu
            980                 985                 990

Asp Lys Thr Pro Ser Leu Thr Leu Lys Asp Ala Leu Lys Leu Ser Tyr
        995                 1000                1005

Pro Asp Glu Ile Lys Glu Ile Glu Gly Leu Leu Tyr Tyr Lys Asn Lys
    1010                1015                1020

Pro Ile Tyr Glu Ser Ser Val Met Thr Tyr Leu Asp Glu Asn Thr Ala
1025                1030                1035                1040

Lys Glu Val Thr Lys Gln Leu Asn Asp Thr Thr Gly Lys Phe Lys Asp
                1045                1050                1055

Val Ser His Leu Tyr Asp Val Lys Leu Thr Pro Lys Met Asn Val Thr
            1060                1065                1070

Ile Lys Leu Ser Ile Leu Tyr Asp Asn Ala Glu Ser Asn Asp Asn Ser
        1075                1080                1085
```

-continued

```
Ile Gly Lys Trp Thr Asn Thr Asn Ile Val Ser Gly Gly Asn Asn Gly
    1090                1095                1100

Lys Lys Gln Tyr Ser Ser Asn Asn Pro Asp Ala Asn Leu Thr Leu Asn
1105                1110                1115                1120

Thr Asp Ala Gln Glu Lys Leu Asn Lys Asn Arg Asp Tyr Tyr Ile Ser
                1125                1130                1135

Leu Tyr Met Lys Ser Glu Lys Asn Thr Gln Cys Glu Ile Thr Ile Asp
            1140                1145                1150

Gly Glu Ile Tyr Pro Ile Thr Thr Lys Thr Val Asn Val Asn Lys Asp
        1155                1160                1165

Asn Tyr Lys Arg Leu Asp Ile Ile Ala His Asn Ile Lys Ser Asn Pro
    1170                1175                1180

Ile Ser Ser Leu His Ile Lys Thr Asn Asp Glu Ile Thr Leu Phe Trp
1185                1190                1195                1200

Asp Asp Ile Ser Ile Thr Asp Val Ala Ser Ile Lys Pro Glu Asn Leu
                1205                1210                1215

Thr Asp Ser Glu Ile Lys Gln Ile Tyr Ser Arg Tyr Gly Ile Lys Leu
            1220                1225                1230

Glu Asp Gly Ile Leu Ile Asp Lys Lys Gly Gly Ile His Tyr Gly Glu
        1235                1240                1245

Phe Ile Asn Glu Ala Ser Phe Asn Ile Glu Pro Leu Gln Asn Tyr Val
    1250                1255                1260

Thr Lys Tyr Glu Val Thr Tyr Ser Ser Glu Leu Gly Pro Asn Val Ser
1265                1270                1275                1280

Asp Thr Leu Glu Ser Asp Lys Ile Tyr Lys Asp Gly Thr Ile Lys Phe
                1285                1290                1295

Asp Phe Thr Lys Tyr Ser Lys Asn Glu Gln Gly Leu Phe Tyr Asp Ser
            1300                1305                1310

Gly Leu Asn Trp Asp Phe Lys Ile Asn Ala Ile Thr Tyr Asp Gly Lys
        1315                1320                1325

Glu Met Asn Val Phe His Arg Tyr Asn Lys
    1330                1335
```